(12) United States Patent
Havlicek et al.

(10) Patent No.: US 11,186,583 B2
(45) Date of Patent: Nov. 30, 2021

(54) 5-ALKYLTHIO-7-[(4-ARYLBENZYL)AMINO]-1(2)H-PYRAZOLO[4,3-D]PYRIMIDINES FOR TREATMENT OF LYMPHOMA

(71) Applicants: UNIVERZITA PALACKEHO V OLOMOUCI, Olomouc (CZ); USTAV EXPERIMENTALNI BOTANIKY AV CR, V.V.I., Praha-Lysolaje (CZ)

(72) Inventors: Libor Havlicek, Krc (CZ); Antonin Sturc, Modrany (CZ); Eva Reznickova, Nova Ulice (CZ); Radek Jorda, Neredin (CZ); Vladimir Krystof, Olomouc (CZ); Miroslav Strnad, Neredin (CZ)

(73) Assignees: UNIVERZITA PALACKEHO V OLOMOUCI, Olomouc (CZ); USTAV EXPERIMENTALNI BOTANIKY AV CR, V.V.I., Praha-Lysolaje (CZ)

( * ) Notice: Subject to any disclaimer, the term of this patent is extended or adjusted under 35 U.S.C. 154(b) by 6 days.

(21) Appl. No.: 16/963,782

(22) PCT Filed: Feb. 1, 2019

(86) PCT No.: PCT/CZ2019/050002
§ 371 (c)(1),
(2) Date: Jul. 21, 2020

(87) PCT Pub. No.: WO2019/149295
PCT Pub. Date: Aug. 8, 2019

(65) Prior Publication Data
US 2020/0361943 A1    Nov. 19, 2020

(30) Foreign Application Priority Data

Feb. 5, 2018    (CZ) .................................. CZ2018-58

(51) Int. Cl.
*C07D 487/04*    (2006.01)
*A61P 35/00*    (2006.01)

(52) U.S. Cl.
CPC ............ *C07D 487/04* (2013.01); *A61P 35/00* (2018.01)

(58) Field of Classification Search
CPC .................................................... C07D 487/04
See application file for complete search history.

(56) References Cited

FOREIGN PATENT DOCUMENTS

WO    03082872 A1    10/2003

OTHER PUBLICATIONS

International Preliminary Report and Written Opinion for corresponding PCT application No. PCT/CZ2019/050002, dated Apr. 17, 2019.

*Primary Examiner* — Benjamin J Packard
(74) *Attorney, Agent, or Firm* — Notaro, Michalos & Zaccaria P.C.

(57) ABSTRACT

5-alkylthio-7-[(4-arylbenzyl)amino]-1(2)H-pyrazolo[4,3-d]pyrimidine derivatives of formula I that are effective inhibitors of kinases and exhibit strong antiproliferative and proapoptotic properties on lymphoma cells. Derivatives in the treatment of blood hyperproliferative diseases, such as Non-Hodgkin lymphomas are also disclosed.

13 Claims, 4 Drawing Sheets

5-ALKYLTHIO-7-[(4-ARYLBENZYL)AMINO]-1(2)H-PYRAZOLO[4,3-D]PYRIMIDINES FOR TREATMENT OF LYMPHOMA

FIELD OF ART

The present invention relates to 5-alkylthio-7-[(4-arylbenzyl)amino]-1(2)H-pyrazolo[4,3-d]pyrimidine derivatives, to processes for their preparation, to pharmaceutical compositions comprising these derivatives, and to their use in the treatment of lymphomas.

BACKGROUND ART

Non-Hodgkin lymphomas (NHL) are the most frequent hematologic malignancies in the Western hemisphere corresponding to approx. 30% of all hematologic cancers. Based on the biological aggressiveness, NHLs can be divided into indolent ("slowly" growing), aggressive and highly-aggressive (with extensive mitotic activity) lymphomas. Aggressive/highly aggressive NHLs include diffuse large B-cell lymphoma (DLBCL), Burkitt's lymphoma (BL), mantle cell lymphoma (MCL) and peripheral T-cell lymphoma (PTCL). Deregulation of cell cycle machinery together with disruption of programmed cell death (apoptosis) belong to hallmarks of aggressive NHLs. These include mutations of transcription factors MYC, TP53, TP63, BCL6, overexpression of cyclin D1, CDK4/6, or deletion of RB1, CDKN2A and ATM. CDK inhibitors interfere with both cell cycle and apoptosis, because they inhibit transcription of short-lived anti-apoptotic molecules (e.g. MCL1, XIAP, cyclin D1), and simultaneously block key positive regulators of cell cycle progression (i.e. CDKs). Double- and triple-hit lymphomas characterized by concurrent genetic aberrations of the MYC, BCL2 and/or BCL6 genes represent a subgroup of chemoresistant NHLs with extremely dismal prognosis (Rosenthal and Younes, Blood Rev. 2016, p. 6).

CDK inhibitors (e.g. flavopiridol, roscovitine, dinaciclib and palbociclib) have been increasingly tested in the setting of relapsed/refractory NHL. We and others have demonstrated that aggressive lymphomas can be divided into BCL2-dependent and MCL1-dependent subtypes, and that concurrent inhibition of BCL2 and MCL1 results in marked cytotoxic synergy (Klanova et al. Clin Cancer Res. 2016 Mar. 1; 22(5):1138-49; Wenzel et al. Leukemia. 2013 June; 27(6):1381-90).

Suppression of MCL1 by CDK9 inhibition by dinaciclib induced durable apoptotic responses in aggressive MYC-driven B-cell lymphoma in vivo (Gregory et al. Leukemia. 2015, (6):1437-41). It has been demonstrated that pharmacological loss of a short-lived MCL1 protein as a consequence of exposure of lymphoma cells to CDK inhibitor dinaciclib sensitized the MYC-BCL2 double-hit lymphomas to BCL2 inhibitor venetoclax (Choudhary et al. Oncotarget. 2015 Jul. 10; 6(19): 16912-16925). Recently it was proven that inhibition of CDK2 by dinaciclib induces cyclin E-dependent phosphorylation and loss of short-lived antiapoptotic MCL1 protein, which sensitizes the dinaciclib-exposed double-hit lymphoma cells to BCL2-specific agent venetoclax (Li et al. Leukemia. 2015 August; 29(8):1702-12).

Currently, CDK inhibitors are in advanced clinical trials for the therapy of various tumors. The CDK4/6 inhibitors palbociclib, ribociclib and abemaciclib have recently been approved by the US FDA for the first-line treatment of metastatic ER-positive and HER2-negative breast cancer. Experimental evidence suggests that inhibition of CDK may have a positive therapeutic effect in treating non-Hodgkin's lymphomas.

It is an object of this invention to provide new, very potent anticancer compounds which can be used in the treatment of lymphoma disorders, such as non-Hodgkin lymphomas.

DISCLOSURE OF THE INVENTION

Object of the present invention are 5-alkylthio-7-[(4-arylbenzyl)amino]-1(2)H-pyrazolo[4,3-d]pyrimidines of the general formula I

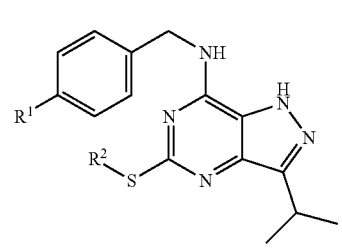

wherein,

R1 is phenyl or heteroaryl having five to six ring atoms, wherein the ring atoms include at least one heteroatom selected from O, S, N and the other ring atoms are carbon atoms; wherein the phenyl or heteroaryl can be optionally substituted with one or more substituents independently selected from Cl, F, $CF_3$, $NH_2$, OH, $NO_2$, $OCH_3$, $OCF_3$;

R2 is selected from the group consisting of
- $C_2$-$C_6$ linear or branched alkyl, optionally substituted by one or more substituents selected from the group containing hydroxy, amino, carbamoyl, =O, guanidino, ureido, trifluoromethyl, sulphanyl, methylsulphanyl, dimethylamino, diethylamino, methylamino, ethylamino, C1-C2-acylamino;
- $C_2$-$C_6$ linear or branched alkenyl, optionally substituted by one or more substituents selected from the group containing hydroxy, amino, carbamoyl, =O, guanidino, ureido, trifluoromethyl, sulphanyl, methylsulphanyl, dimethylamino, diethylamino, methylamino, ethylamino, C1-C2-acylamino;
- $C_3$-$C_6$ cycloalkyl, wherein the cycloalkyl contains 3 to 6 carbon atoms and is substituted by one or more substituents selected from the group containing hydroxy, amino, carbamoyl, =O, guanidino, ureido, trifluoromethyl, sulphanyl, methylsulphanyl, dimethylamino, diethylamino, methylamino, ethylamino, C1-C2-acylamino;
- linear or branched heteroalkyl containing 2 to 6 atoms of which at least one is a heteroatom selected from O, S, N and the other are carbon atoms; wherein the heteroalkyl group can be optionally substituted by one or more substituents independently selected from the group containing hydroxy, amino, carbamoyl, =O, guanidino, ureido, trifluoromethyl, sulphanyl, methylsulphanyl, dimethylamino, diethylamino, methylamino, ethylamino, C1-C2-acylamino;
- cycloheteroalkyl containing 3 to 6 atoms of which at least one is a heteroatom selected from O, S, N and the other are carbon atoms; wherein the cycloheteroalkyl group can be optionally substituted by one or more substituents independently selected from the group containing hydroxy, amino, carbamoyl, =O, guanidino, ureido, trifluoromethyl, sulphanyl, methylsulphanyl, dimethylamino, diethylamino, methylamino, ethylamino, C1-C2-acylamino, C1-C4 alkyl;

cycloheteroalkyl-methyl, cycloheteroalkyl-ethyl or cycloheteroalkyl-propyl, wherein the cycloheteroalkyl group is as described above;

and pharmaceutically acceptable salts thereof, in particular salts with alkali metals, ammonium or amines, or addition salts with acids.

$R^1$ is preferably selected from the group consisting of phenyl, pyridin-2-yl, pyridin-3-yl, pyridin-4-yl, pyrimidin-2-yl, pyrimidin-4-yl, pyrimidin-5-yl, pyrazin-2-yl, pyridazin-3-yl, pyridazin-4-yl, pyrrol-1-yl, pyrrol-2-yl, pyrrol-3-yl, pyrazol-1-yl, pyrazol-3-yl, pyrazol-4-yl, imidazol-1-yl, imidazol-2-yl, imidazol-4-yl, furan-2-yl, furan-3-yl, thien-2-yl, thien-3-yl, oxazol-2-yl, thiazol-2-yl, tetrazol-5-yl; these groups may be unsubstituted or substituted with one or more substituents independently selected from the group consisting of Cl, F, $CF_3$, $NH_2$, OH, $NO_2$, $OCH_3$, $OCF_3$.

Preferably, $R^2$ is a $C_2$-$C_6$ linear or $C_2$-$C_5$ branched alkyl substituted with one or two hydroxy groups. More preferably, $R^2$ is selected from the group consisting of: 2-hydroxyethyl, 2-(RS, R or S)-hydroxypropyl, 3-hydroxypropyl, 2-hydroxybutyl, 1-hydroxybut-2-yl, 2-hydroxybut-2-yl, 1-hydroxy-3-methylbut-2-yl, 4-hydroxybut-2-(RS, R, or S)-yl, 2-hydroxy-2-methylpropyl, 3-hydroxy-3-methylbut-2-yl, (RS, R or S)-2,3-dihydroxypropyl, 1-hydroxy-3-methylbut-2-yl, and (3RS)-2-hydroxypent-3-yl.

In another preferred embodiment, the $C_2$-$C_6$ linear or branched alkyl is substituted with one or two amino groups, optionally the amino group is further substituted. Preferably, the $C_2$-$C_6$ linear or branched alkyl is selected from the group consisting of: 2-aminoethyl, 3-aminopropyl, 4-aminobutyl, 5-aminopentyl, 6-aminohexyl, 2,3-diaminopropyl, (R)-2,3-diaminopropyl, (S)-2,3-diaminopropyl, 2-guanidinoethyl, and 2-ureidoethyl, 2-(acetylamino)ethyl, (dimethylamino)methyl, 2-(dimethylamino)ethyl, 3-(dimethylamino)propyl, 4-(dimethylamino)butyl, (diethylamino)methyl, 2-(diethylamino)ethyl, 3-(diethylamino)propyl and 4-(diethylamino)butyl.

In another preferred embodiment, the $C_2$-$C_6$ linear or branched alkyl is substituted with a carbamoyl group. Preferably, the $C_2$-$C_6$ linear or branched alkyl is selected from (carbamoyl)methyl, 2-(carbamoyl)ethyl and 3-(carbamoyl)propyl.

In another preferred embodiment, the linear or branched heteroalkyl contains O or S heteroatom (i.e. forms an ether or thioether structure). Preferably, the linear or branched heteroalkyl is selected from methoxymethyl, ethoxymethyl and 2-(methylthio)ethyl.

In another preferred embodiment, $C_2$-$C_6$ linear or branched alkyl is simultaneously substituted by amino and hydroxy. Preferably, the $C_2$-$C_6$ linear or branched alkyl is selected from the group consisting of 3-amino-2-hydroxypropyl, (R)-3-amino-2-hydroxypropyl, (S)-3-amino-2-hydroxypropyl, 2-amino-3-hydroxypropyl, (R)-2-amino-3-hydroxypropyl, and (S)-3-amino-2-hydroxypropyl.

Preferably $R^2$ is $C_2$-$C_3$ linear alkyl substituted with one or two sulfanyl groups, or with a combination of sulfanyl and hydroxy groups. Preferably, $C_2$-$C_3$ linear alkyl is selected from the group consisting of 2-sulfanylethyl, 3-hydroxy-2-sulfanylpropyl, and 2-hydroxy-3-sulfanylpropyl.

In another preferred embodiment, the $C_3$-$C_6$ cycloalkyl is selected from the group containing cyclopropyl, cyclobutyl, cyclopentyl and cyclohexyl.

In another preferred embodiment, $C_3$-$C_6$ cycloalkyl is substituted with amino or hydroxy. Preferably, the $C_3$-$C_6$ cycloalkyl is selected from the group consisting of: trans-4-aminocyclohexyl, cis-4-aminocyclohexyl, cis,trans-4-aminocyclohexyl, cis-2-aminocyclohexyl, trans-2-aminocyclohexyl, cis,trans-2-aminocyclohexyl, 3-aminocyclohexyl, trans-4-hydroxycyclohexyl, cis-4-hydroxycyclohexyl, cis,trans-4-hydroxycyclohexyl, cis-2-hydroxycyclohexyl, trans-2-hydroxycyclohexyl, cis,trans-2-hydroxycyclohexyl, 3-hydroxycyclohexyl.

In another preferred embodiment, $R^2$ is cycloheteroalkyl, cycloheteroalkyl-methyl, cycloheteroalkyl-ethyl or cycloheteroalkyl-propyl containing at least one nitrogen atom or at least one oxygen atom or both nitrogen and oxygen heteroatoms. Preferably, $R^2$ is selected from the group consisting of: N-morpholinyl, N-pyrrolidinyl, N-pyrazolidinyl, N-imidazolidinyl, N-piperazinyl, N-piperidinyl, N-thiomorpholinyl, 4-methylpiperazin-1-yl, 4-(2-hydroxyethyl)piperazin-1-yl, (aziridin-1-yl)ethyl, (azetidin-1-yl)ethyl, (azolidin-1-yl)ethyl, (piperidin-1-yl)ethyl, (aziridin-1-yl)propyl, (azetidin-1-yl)propyl, (azolidin-1-yl)propyl, (piperidin-1-yl)propyl and 2-oxazolidon-5-yl.

When chiral centers are present in the molecule, the present invention encompasses all optically active isomers, their mixtures and racemates. In particular, the compounds of general formula I, having independently at each occurrence (R) or (S) configuration, are encompassed by this invention.

The 5-alkylthio-7-[(4-arylbenzyl)amino]-1(2)H-pyrazolo[4,3-d]pyrimidines of the general formula I are useful as medicaments. It was found within the framework of the present invention that these compounds combine antiproliferative and proapoptotic activities which is particularly beneficial for treatment of non-Hodgkin lymphomas.

In one embodiment, the 5-alkylthio-7-[(4-arylbenzyl)amino]-1(2)H-pyrazolo[4,3-d]pyrimidines of the general formula I are for use in the treatment of blood hyperproliferative diseases. In particular, they are for use in the treatment of non-Hodgkin lymphomas.

In one embodiment, the 5-alkylthio-7-[(4-arylbenzyl)amino]-1(2)H-pyrazolo[4,3-d]pyrimidines of the general formula I are for use for therapeutic inhibition of CDK1/2/5/7/9 kinases which are the key components involved in regulation of cell division and differentiation of blood progenitors, and in the development of lymphomas.

In one aspect of this invention, the 5-alkylthio-7-[(4-arylbenzyl)amino]-1(2)H-pyrazolo[4,3-d]pyrimidines of the general formula I are for use in the treatment of blood disorders involving aberrant cell proliferation and/or apoptosis. In an aspect of the invention, a method of treatment of lymphomas is provided, in a mammal in need of such treatment, by administering a therapeutically effective amount of at least one compound of formula I to the said mammal.

The invention also encompasses a pharmaceutical composition, which comprises at least one 5-alkylthio-7-[(4-arylbenzyl)amino]-1(2)H-pyrazolo[4,3-d]pyrimidine of the general formula I, and at least one pharmaceutically acceptable carrier.

Particularly preferred compounds of the present invention are derivatives of the formula I which carry the substituent $R^2$ selected from the group consisting of: 2-hydroxyethyl, 3-hydroxypropyl, 2(R)-hydroxypropyl, 2(S)-hydroxypropyl, 4-hydroxybut-2(R)-yl, 4-hydroxybut-2(S)-yl, 4-hydroxybut-2(R,S)-yl, 2-hydroxy-2-methylpropyl, 2,3-dihydroxypropyl, 3-hydroxy-3-methylbutyl, 2-hydroxypent-3-yl, (R)-1-isopropyl-2-hydroxyethyl, (S)-1-isopropyl-2- hydroxyethyl, (R,S)-1-isopropyl-2-hydroxyethyl, 2-aminoethyl, 3-aminopropyl, 4-aminobutyl, 5-aminopentyl, 6-aminohexyl, 3-amino-2-hydroxypropyl, 2,3-diaminopropyl, 1-(dimethylamino)methyl, 2-(dimethylamino)ethyl, 3-(dimethylamino)propyl, 4-(dimethylamino)butyl, 2-(diethylamino)ethyl, 3-(diethylamino)propyl, cis-2-aminocyclohexyl, trans-2-aminocyclohexyl, cis,trans-2-aminocyclohexyl, cis,trans-3-aminocyclohexyl, trans-4-aminocyclohexyl, cis-4-aminocyclohexyl, cis,trans-4-aminocyclohexyl, cis-2-hydroxycyclohexyl, trans-2-hydroxycyclohexyl, cis,trans-2-hydroxycyclohexyl, cis,trans-3-hydroxycyclohexyl, trans-4-hydroxycyclohexyl, cis-4-hydroxycyclohexyl, cis,trans-4-hydroxycyclohexyl.

Processes of Preparation of Compounds of General Formula I

In this new generation of 5,7-disubstituted 3-isopropylpyrazolo-1(2)H-[4,3-d]pyrimidines, the substituent (alkylamino) at the position 5 of the central heterocycle is replaced by an alkylthio group. This substitution of the heterocycle is synthetically more feasible (the alkylation is carried out under mild conditions). Compared to the known 5-alkylamino substitution, which is carried out by nucleophilic aromatic substitution, typically requiring activation at 150° C., undesirable reactions are limited. The latter substituent introduced by the reaction sequence into the 5-position of the heterocycle is bound to the heterocycle by reacting with a reactive sulfanyl group, which also allows for a great versatility in substitution (reaction with alkyl halides, epoxides, aziridines etc.).

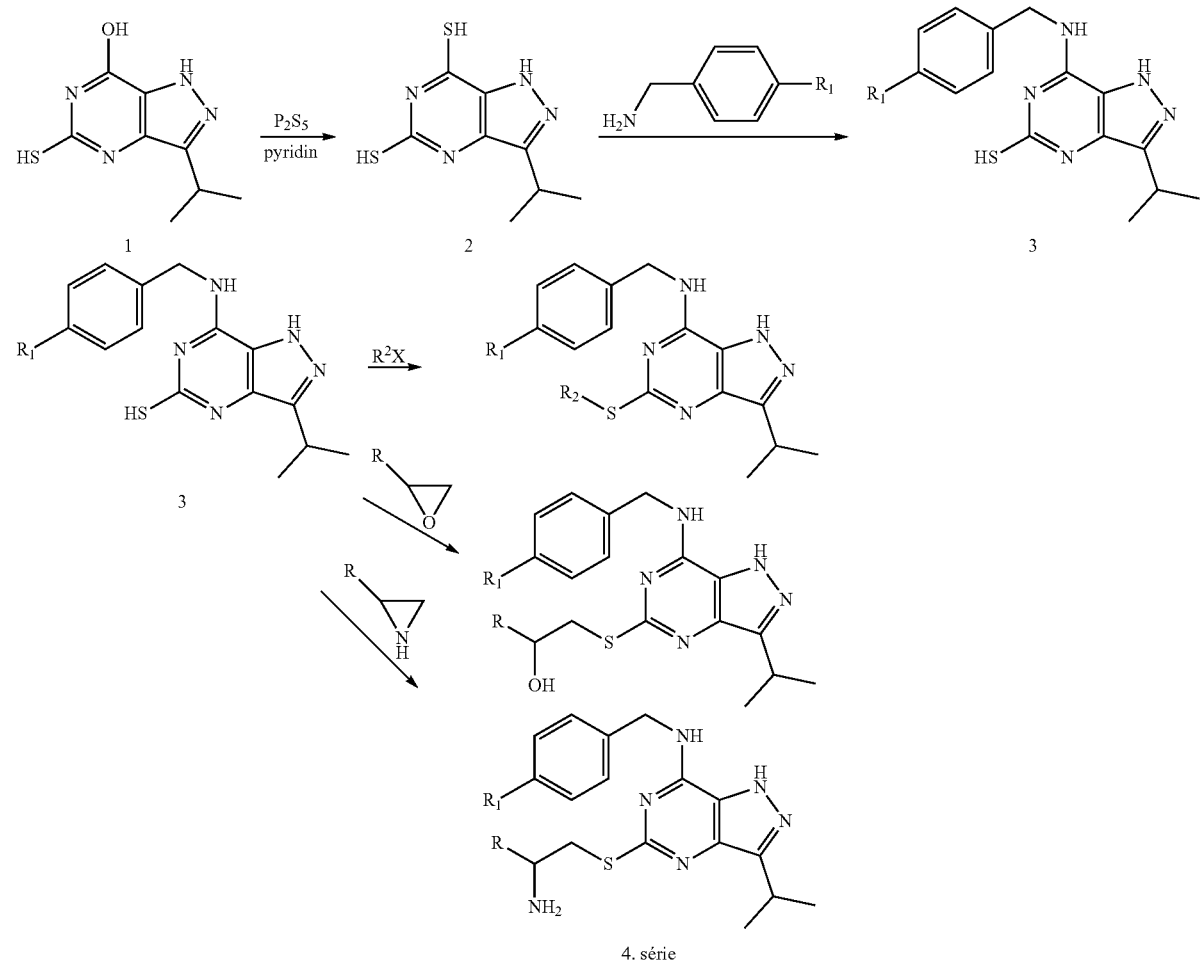

4. série

Scheme 1 herein above shows the versatility of syntheses of 5-alkylthio-7-(4-arylbenzyl)amino-1(2H)-pyrazolo[4,3-d]pyrimidines: 3-Isopropyl-5-sulfanyl-1(2)H-pyrazolo[4,3-d]pyrimidin-7-ol (1) is converted by phosphorus pentasulfide to a 5,7-disulfanyl derivative (2). Nucleophilic aromatic substitution of the sulfanyl group in the position 7 of the heterocycle under mild conditions yields a 7-[(4-arylbenzyl)amino]-5-sulfanyl-1(2H)-pyrazolo[4,3-d]pyrimidine (3). By alkylation of the thiol (3) with an organic halogenide, oxirane or aziridine, the target structure (4) is prepared.

Pharmaceutical Compositions

Suitable routes for administration include oral, rectal, topical (including dermal, ocular, buccal and sublingual), vaginal and parenteral (including subcutaneous, intramuscular, intravitreous, intravenous, intradermal, intrathecal and epidural). The preferred route of administration will depend upon the condition of the patient, the toxicity of the compound and the site of infection, among other considerations known to the clinician.

The therapeutical composition comprises about 1% to about 95% of the active ingredient, single-dose forms of administration preferably comprise about 20% to about 90% of the active ingredient and administration forms which are not single-dose preferably comprise about 5% to about 20% of the active ingredient. Unit dose forms are, for example, coated tablets, tablets, ampoules, vials, suppositories or capsules. Other forms of administration are, for example, ointments, creams, pastes, foams, tinctures, lipsticks, drops, sprays, dispersions and the like. Examples are capsules containing from about 0.05 g to about 1.0 g of the active ingredient.

The pharmaceutical compositions of the present invention are prepared in a manner known per se, for example by means of convectional mixing, granulating, coating, dissolving or lyophilising processes. Preferably, solutions of the active ingredient, and in addition also suspensions or dispersions, especially isotonic aqueous solutions, dispersions or suspensions, are used, it being possible for these to be prepared before use, for example in the case of lyophilised compositions which comprise the active substance by itself or together with a carrier, for example mannitol. The pharmaceutical compositions can be sterilised and/or comprise excipients, for example preservatives, stabilisers, wetting agents and/or emulsifiers, solubilizing agents, salts for regulating the osmotic pressure and/or buffers, and they are prepared in a manner known per se, for example by means of convectional dissolving or lyophilising processes. The solutions or suspensions mentioned can comprise viscosity-increasing substances, such as sodium carboxymethylcellulose, carboxymethylcellulose, dextran, polyvinylpyrrolidone or gelatin.

Suspensions in oil comprise, as the oily component, the vegetable, synthetic or semi-synthetic oils customary for injection purposes. Oils which may be mentioned are, in particular, liquid fatty acid esters which contain, as the acid component, a long-chain fatty acid having 8-22, in particular 12-22, carbon atoms, for example lauric acid, tridecylic acid, myristic acid, pentadecylic acid, palmitic acid, margaric acid, stearic acid, acid, arachidonic acid, behenic acid or corresponding unsaturated acids, for example oleic acid, elaidic acid, euric acid, brasidic acid or linoleic acid, if appropriate with the addition of antioxidants, for example vitamin E, β-carotene or 3,5-di-tert-butyl-4-hydroxytoluene. The alcohol component of these fatty acid esters has not more than 6 carbon atoms and is mono- or polyhydric, for example mono-, di- or trihydric alcohol, for example methanol, ethanol, propanol, butanol, or pentanol, or isomers thereof, but in particular glycol and glycerol. Fatty acid esters are therefore, for example: ethyl oleate, isopropyl myristate, isopropyl palmitate, "Labrafil M 2375" (polyoxyethylene glycerol trioleate from Gattefoseé, Paris), "Labrafil M 1944 CS" (unsaturated polyglycolated glycerides prepared by an alcoholysis of apricot kernel oil and made up of glycerides and polyethylene glycol esters; from Gattefoseé, Paris), "Labrasol" (saturated polyglycolated glycerides prepared by an alcoholysis of TCM and made up of glycerides and polyethylene glycol esters; from Gattefoseé, Paris) and/or "Miglyol 812" (triglyceride of saturated fatty acids of chain length $C_8$ to $C_{12}$ from Hüls AG, Germany), and in particular vegetable oils, such as cottonseed oil, almond oil, olive oil, castor oil, sesame oil, soybean oil and, in particular, groundnut oil.

The preparation of the injection compositions is carried out in the customary manner under sterile conditions, as are bottling, for example in ampoules or vials, and closing of the containers.

For example, pharmaceutical compositions for oral use can be obtained by combining the active ingredient with one or more solid carriers, if appropriate granulating the resulting mixture, and, if desired, processing the mixture or granules to tablets or coated tablet cores, if appropriate by addition of additional excipients. Suitable carriers are, in particular, fillers, such as sugars, for example lactose, sucrose, mannitol or sorbitol, cellulose preparations and/or calcium phosphates, for example tricalcium diphosphate, or calcium hydrogen phosphate, and furthermore binders, such as starches, for example maize, wheat, rice or potato starch, methylcellulose, hydroxypropylmethylcellulose, sodium carboxymethylcellulose and/or polyvinylpyrrolidine, and/or, if desired, desintegrators, such as the above mentioned starches, and furthermore carboxymethyl-starch, cross-linked polyvinylpyrrolidone, alginic acid or a salt thereof, such as sodium alginate. Additional excipients are, in particular, flow regulators and lubricants, for example salicylic acid, talc, stearic acid or salts thereof, such as magnesium stearate or calcium stearate, and/or polyethylene glycol, or derivatives thereof.

Coated tablet cores can be provided with suitable coatings which, if appropriate, are resistant to gastric juice, the coatings used being, inter alia, concentrated sugar solutions, which, if appropriate, comprise gum arabic, talc, polyvinylpyrrolidine, polyethylene glycol and/or titanium dioxide, coating solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate. Dyes or pigments can be admixed to the tablets or coated tablet coatings, for example for identification or characterisation of different doses of active ingredient.

Pharmaceutical compositions, which can be used orally, are also hard capsules of gelatin and soft, closed capsules of gelatin and a plasticiser, such as glycerol or sorbitol. The hard capsules can contain the active ingredient in the form of granules, mixed for example with fillers, such as maize starch, binders and/or lubricants, such as talc or magnesium stearate, and stabilisers if appropriate. In soft capsules, the active ingredient is preferably dissolved or suspended in suitable liquid excipients, such as greasy oils, paraffin oil or liquid polyethylene glycols or fatty acid esters of ethylene glycol or propylene glycol, it being likewise possible to add stabilisers and detergents, for example of the polyethylene sorbitan fatty acid ester type.

Other oral forms of administration are, for example, syrups prepared in the customary manner, which comprise the active ingredient, for example, in suspended form and in a concentration of about 5% to 20%, preferably about 10% or in a similar concentration which results in a suitable individual dose, for example, when 5 or 10 ml are measured out. Other forms are, for example, also pulverulent or liquid concentrates for preparing of shakes, for example in milk. Such concentrates can also be packed in unit dose quantities.

Pharmaceutical compositions, which can be used rectally, are, for example, suppositories that comprise a combination of the active ingredient with a suppository base. Suitable suppository bases are, for example, naturally occurring or synthetic triglycerides, paraffin hydrocarbons, polyethylene glycols or higher alkanols.

Compositions which are suitable for parental administration are aqueous solutions of an active ingredient in water-soluble form, for example of water-soluble salt, or aqueous injection suspensions, which comprise viscosity-increasing substances, for example sodium carboxymethylcellulose, sorbitol and/or dextran, and if appropriate stabilisers. The active ingredient can also be present here in the form of a lyophilisate, if appropriate together with excipients, and be dissolved before parenteral administration by addition of suitable solvents. Solutions such as are used, for example, for parental administration can also be used as infusion solutions. Preferred preservatives are, for example antioxidants, such as ascorbic acid, or microbicides, such as sorbic or benzoic acid.

Ointments are oil-in-water emulsions, which comprise not more than 70%, but preferably 20-50% of water or aqueous phase. The fatty phase consists of, in particular, hydrocarbons, for example vaseline, paraffin oil or hard paraffins, which preferably comprise suitable hydroxy compounds, such as fatty alcohols or esters thereof, for example cetyl alcohol or wool wax alcohols, such as wool wax, to improve the water-binding capacity. Emulsifiers are lipophilic substances, such as sorbitan fatty acid esters (Spans), preferably sorbitan oleate or sorbitan isostearate. Additives to the aqueous phase are, for example, humectants, such as polyalcohols, for example glycerol, propylene glycol, sorbitol and polyethylene glycol, or preservatives and odoriferous substances.

Fatty ointments are anhydrous and comprise, as the base, in particular, hydrocarbons, for example paraffin, vaseline or paraffin oil, and furthermore naturally occurring or semi-synthetic fats, for example hydrogenated coconut-fatty acid triglycerides, or hydrogenated oils, for example hydrogenated groundnut or castor oil, and furthermore fatty acid partial esters of glycerol, for example glycerol mono- and distearate. They also contain e.g. fatty alcohols, emulsifiers and additives mentioned in connection with ointments which increase the uptake of water.

Creams are oil-in-water emulsions, which comprise more than 50% of water. Oily bases used are, in particular, fatty alcohols, for example isopropyl myristate, wool wax, beeswax, or hydrocarbons, for example vaseline (petrolatum) or paraffin oil. Emulsifiers are surface-active substances with predominantly hydrophilic properties, such as corresponding non-ionic emulsifiers, for example fatty acid esters of polyalcohols or ethyleneoxy adducts thereof, such as polyglyceric fatty acid esters or polyethylene sorbitan fatty acid esters or acidic polyglyceric fatty acid esters (Tween), and furthermore polyoxyethylene fatty alcohol ethers or polyoxyethylene fatty acid esters, or ionic emulsifiers, such as alkali metal salts of fatty alcohol sulphates, preferably sodium lauryl sulphate, sodium cetyl sulphate or sodium stearyl sulphate, which are usually used in the presence of fatty alcohols, for example cetyl stearyl alcohol or stearyl alcohol. Additives to the aqueous phase are, inter alia, agents which prevent the creams from drying out, for example polyalcohols, such as glycerol, sorbitol, propylene glycol and polyethylene glycols, and furthermore preservatives and odoriferous substances.

Pastes are creams or ointments containing secretion-absorbing powder constituents, such as metal oxides, for example titanium oxide or zinc oxide, and in addition talc or aluminium silicates, which have the task of binding the moisture or secretions present.

Foams are administered from pressurised containers and they are liquid oil-in-water emulsions present in aerosol foam. As the propellant gases halogenated hydrocarbons, such as polyhalogenated alkanes, for example dichlorofluoromethane and dichlorotetrafluoroethane, or, preferably, non-halogenated gaseous hydrocarbons, air, $N_2O$, or carbon dioxide are used. The oily phases used are, inter alia, those mentioned above for ointments, and the additives mentioned there are likewise used.

Tinctures and solutions usually comprise an aqueous-ethanolic base to which, humectants for reducing evaporation, such as polyalcohols, for example glycerol, glycols and polyethylene glycol, and re-oiling substances, such as fatty acid esters with lower polyethylene glycols, i.e. lipophilic substances soluble in the aqueous mixture to substitute the fatty substances removed from the skin with the ethanol, and, if necessary, other excipients and additives are admixed.

This invention further provides veterinary preparations containing at least one active ingredient together with a veterinary carrier. Veterinary carriers are materials for the application of a composition and include solid, liquid or gaseous substances, which are inert or acceptable in veterinary medicine and are compatible with the active ingredient. These veterinary preparations can be administered orally, parenterally or by any other desired way.

The invention also relates to a process or method for treatment of the disease states mentioned above.

The compounds can be administered prophylactically or therapeutically as such or in the form of pharmaceutical compositions, preferably in an amount, which is effective against the diseases mentioned. With a warm-blooded animal, for example a human, requiring such treatment, the compounds are used, in particular, in the form of pharmaceutical composition. A daily dose of about 0.1 to about 5 g, preferably 0.5 g to about 2 g, of a compound of the present invention is administered here for a body weight of about 70 kg.

EXAMPLES OF CARRYING OUT THE INVENTION

Figure 1:
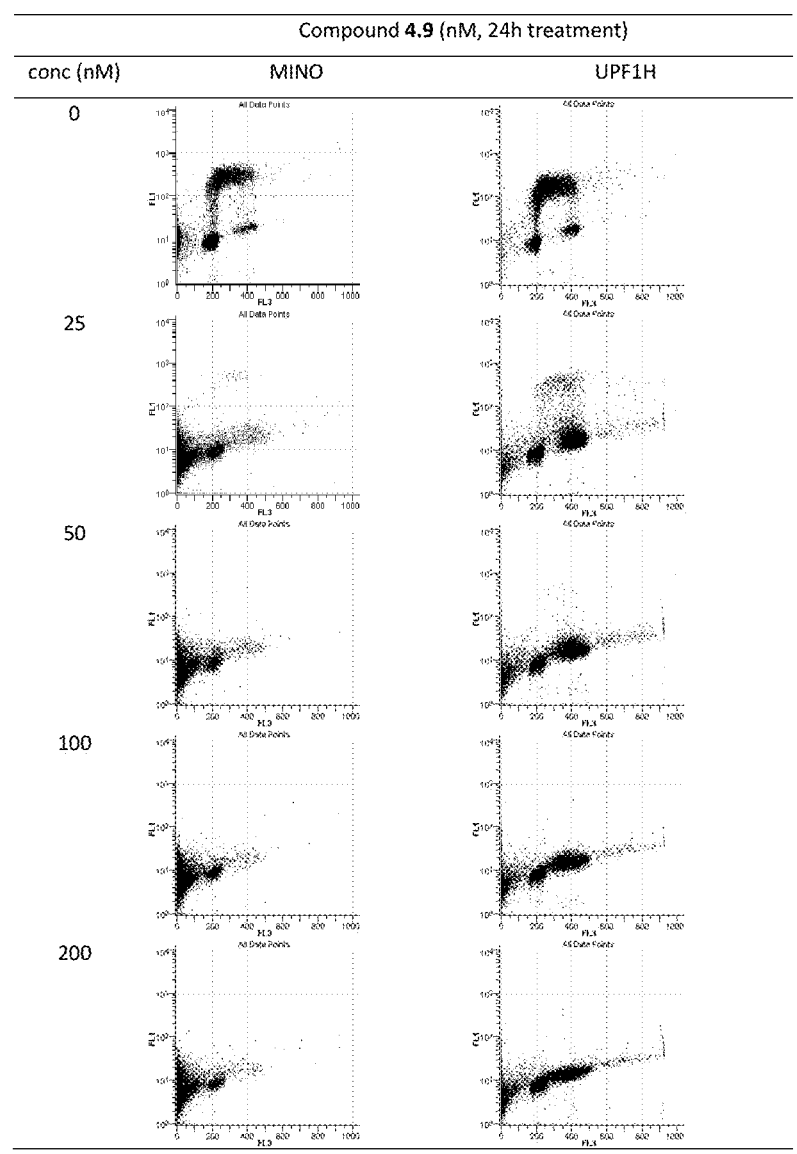
FIG. 1 shows the antiproliferative activity of candidate compound 4.9 in an asynchronously growing lymphoma cell line MINO and UPF1H after 24-hour treatment.
Figure 2:
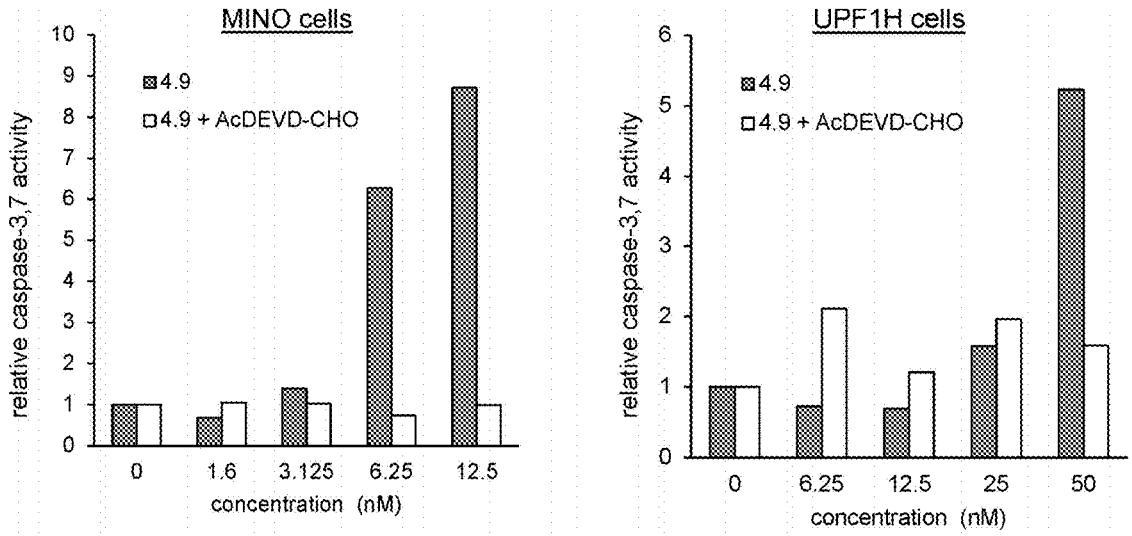
FIG. 2 displays the effect of pyrazolo[4,3-d]pyrimidine 4.9 on apoptosis in treated MINO and UPF1H lymphoma cells. The activities of caspases 3 and 7 were measured in cell lysate in the presence of fluorogenic substrate Ac-DEVD-AMC (grey columns) or fluorogenic caspase inhibitor Ac-DEVD-CHO (white columns) as a control.
Figure 3:
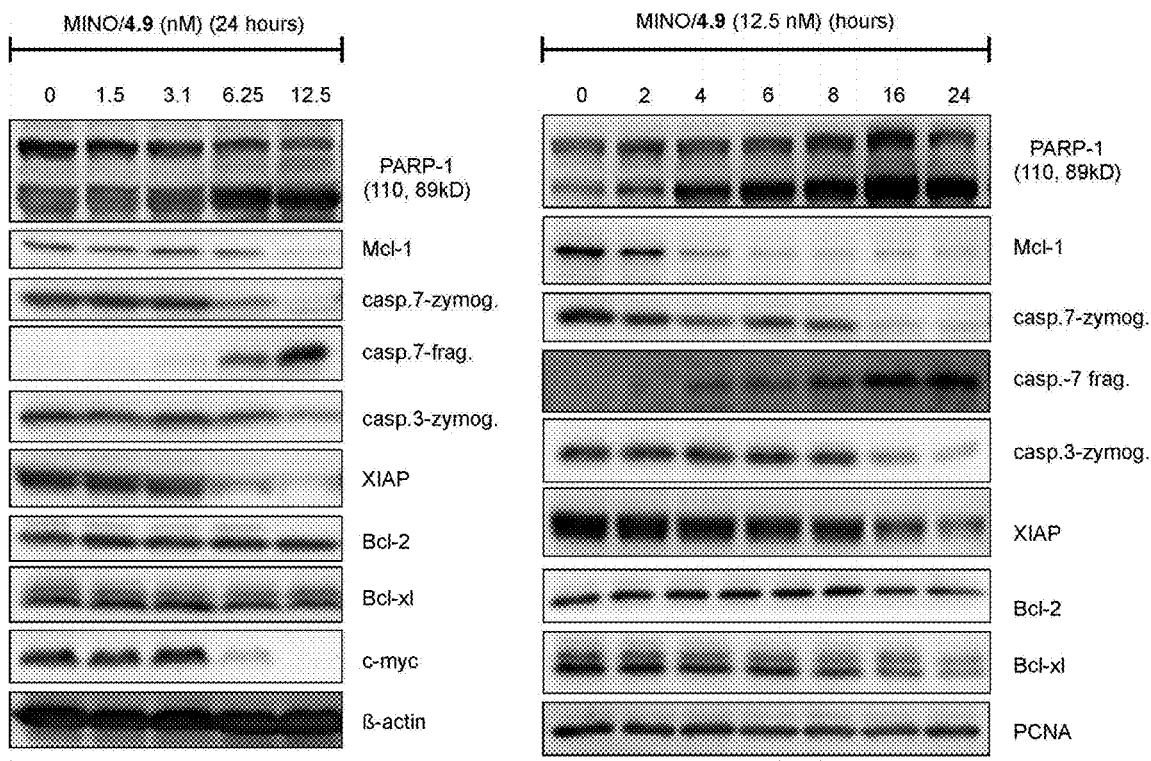
FIG. 3 shows the immunoblotting analysis of apoptosis-related proteins in MINO cells treated by various concentrations of compound 4.9 for 24 h (left panel) or by 12.5 nM 4.9 in different time points (right panel). Actin level is included as a control for equal loading.

The following examples serve to illustrate the invention without limiting the scope thereof.

Methods:

NMR spectra were recorded on a JEOL ECA-500 spectrometer operating at frequencies of 500.16 MHz (H) and 125.76 MHz ($^{13}$C). $^1$H NMR and $^{13}$C NMR chemical shifts were referenced to the solvent signals; $^1$H: δ (residual $CHCl_3$)=7.25 ppm, δ (residual DMSO-$d_5$)=2.50 ppm, δ (residual $CD_3OD$)=3.31 ppm; $^{13}$C: δ ($CDCl_3$)=77.23 ppm, δ (DMSO-$d_6$)=39.52 ppm, δ (CD3OD)=49.15 ppm. Chemical shifts are given in δ scale [ppm] and coupling constants in Hz. Melting points were determined on a Kofler block and are uncorrected. Reagents were of analytical grade from standard commercial sources or were sythesized according to the referenced procedure. Thin layer chromatography (TLC) was carried out using aluminium sheets with silica gel F254 from Merck. Spots were visualized under UV light (254 nm). ESI or APCI mass spectra were determined using a Waters Micromass ZMD mass spectrometer (solution of sample in MeOH, direct inlet, coin voltage was in range 10-30 V, trace of HCOOH or $NH_4OH$ was used for influenzing of ionization). Column chromatography was performed using Merck silica gel Kieselgel 60 (230-400 mesh). The purity of all synthesized compounds was determined by HPLC-PDA (200-500 nm). Specific optical rotation was measured on polarimeter polAAr 3001 (wave length: 589.0 nm, tube length: 50 mm, at 23° C.). All compounds gave satisfactory elemental analyses (0.4%).

Example 1. Preparation of 5-alkylthio-7-[(4-arylbenzyl)amino]-3-isopropyl-1(2)H-pyrazolo[4,3-d]pyrimidies 3-Isopropyl-5-sulfanyl-1(2)H-pyrazolo[4,3-d]pyrimidine-7-ol (1) was prepared according to literature (J. Med. Chem. 2011, 54, 2980-2993).

3-Isopropyl-1(2)H-pyrazolo[4,3-d]pyrimidin-5,7-dithiol (2)

3-Isopropyl-5-sulfanyl-1(2)H-pyrazolo [4,3-d]pyrimidin-7-ol (1) (74 g, 0.35 mol) was added to a solution of phosphorus pentasulfide (93 g, 0.42 mol) in pyridine (550 mL) at 75° C. The reaction mixture was refluxed under nitrogen for 3 h. Then the mixture was concentrated by distillation of pyridine at atmospheric pressure to a syrupy consistency. Water (demineralized, approx. 400 mL) was slowly added at the temperature 65-75° C. The resulting foamy suspension was heated at 95° C. for 1.5 h, After cooling to room temperature, the product was crystallized, filtered off, washed with water and finally ethanol (ca. 200 mL). Drying in vacuo at 75° C. gave 61.7 g [titration of SH, NaOH gave 99.1%], yield 76%. Analytical sample was crystallized from THF, mp 283-293° C., UV (nm): 274 $\lambda_{max}$, 320 $\lambda_{max}$, 372 sh. MS APCI+m/z 227.1 (M+H)$^+$, APCI and ES− m/z 225.1 (M−H)$^−$. $^1$H (500 MHz; DMSO-$d_6$): 1.19 (d, J=7.03 Hz, —CH($CH_3$)$_2$); 13.21 (bs, 1H); 13.30 (bs, 1H); 13.78 (bs, 1H). $^{13}$C (125 MHz; DMSO-$d_6$): 21.9; 24.8; 121.5; 133.0; 143.4; 170.1; 175.1. Anal. ($C_8H_{10}N_4S_2$) C, H, N, S.

3-isopropyl-7-[4-(2-pyridyl)benzyl]amino-1(2)H-pyrazolo[4,3-d]pyrimidin-5-thiol (3.1.): 4-(2-pyridyl)benzylamine (26.2 g; 0.14 mol) was dissolved in 2-ethoxyethanol (150 mL) at 50° C. and 3-isopropyl-1(2)H-pyrazolo[4,3-d]pyrimidin-5,7-dithio (2) (23 g, 0.10 mol) was added under nitrogen gas. The reaction mixture was then refluxed for 8 h. The product crystallized after slow cooling at rt. and then at 5-10° C. The product was filtered off, washed with 2-methoxyethanol and finally with THF, and dried in vacuo at 75° C., 30 g, yield 78%. Titration of basic NH in AcOH with 0.1 N $HClO_4$ gave 100% of product. Analytical sample was crystallized from DMSO/$H_2O$, dried in vacuo at 75° C., mp 263-272° C., UV (nm): 255 $\lambda_{max}$, 289 $\lambda_{max}$, 336 $\lambda_{max}$. MS ESI+ 377.1 (M+H)$^+$, ESI− 375.1 (M−H)$^−$. $^1$H (500 MHz; DMSO-$d_6$): 1.24 (d, J=7.03 Hz, 6H); 3.32 (bs, 1H); 3.45 (bs, 1H); 4.80 (bs, 2H); 7.31-7.33 (m, 1H); 7.46 (bd, J=6.42 Hz, 2H); 7.83-7.86 (m, 1H); 7.91-7.93 (m, 1H); 8.04 (bd, J=7.34 Hz, 2H); 8.64 (bd, J=3.97 Hz, 1H). $^{13}$C (125 MHz; DMSO-$d_6$): 21.7; 42.5; 54.8; 120.0; 122.4; 126.1; 127.7; 137.0; 149.4; 155.7. Anal. ($C_{20}H_{20}N_6S$) C, H, N, S.

3-isopropyl-7-[4-(pyrazol-1-yl)benzyl]amino-1(2)H-pyrazolo[4,3-d]pyrimidin-5-thiol (3.2.)

4-(Pyrazol-1-yl)benzylamine (12.2 g, 0.07 mol) was dissolved in 50 mL of 2-methoxyethanol (75 mL) and 3-isopropyl-pyrimidine-5,7-dithiol (2) (13.3 g, 0.059 mol) was added under an atmosphere of nitrogen. The reaction mixture was heated at 120° C. for 12 hours. The reaction product crystallized upon cooling to 10-15° C. and was filtered off. After washing with 2-methoxyethanol, then THF, and drying in vacuo at 75° C., 13.7 g of product are obtained in 62% yield. The analytical sample was recrystallized from DMSO/$H_2O$, dried at 75° C. under vacuum; m.p. 268-270° C. (decomposition), UV (nm): 268 $\lambda_{max}$, 288 $\lambda_{max}$, 300 $\lambda_{sh}$, 336 $\lambda_{max}$. MS ESI+ 366.1 (M+H)$^+$, ESI− 364.1 (M−H)$^−$. NMR $^1$H (500 MHz; DMSO-$d_6$): 1.23 (d, J=7.03 Hz, 6H, —CH($CH_3$)$_2$); 3.44 (bs, 1H, —CH($CH_3$)$_2$); 4.75 (d, J=6.11 Hz, 2H, —NH—$CH_2$—); 6.50-6.51 (m, 1H, $H_{Ar}$); 7.46 (d, J=7.95 Hz, 2H, $H_{Ar}$); 7.71 (d, J=1.53 Hz, 1H, $H_{Ar}$); 7.79 (d, J=8.25 Hz, 2H, $H_{Ar}$); 8.45 (d, J=2.45 Hz, 1H, $H_{Ar}$); 9.17 (bs, 1H, —NH—); 12.23 (bs, 1H, —NH); 13.74 (bs, 1H, —SH). $^{13}$C (125 MHz; DMSO-$d_6$): 21.8; 42.4; 107.7; 118.3; 127.6; 128.7; 138.7; 140.8. Anal. ($C_{18}H_{19}N_7S$) C, H, N, S.

3-isopropyl-7-[4(imidazol-1-yl)benzyl]amino-1(2)H-pyrazolo[4,3-d]pyrimidin-5-thiol (3.3.)

4-(Imidazol-1-yl)benzylamine (2.4 g, 0.014 mol) was dissolved in 50 mL of 2-methoxyethanol (15 mL) and 3-isopropyl-pyrimidine-5,7-dithiol (2) (1.9 g, 0.008 mol) was added under an atmosphere of nitrogen. The reaction mixture was refluxed for 15 hours. The reaction product crystallized after evaporation of the solvent and after standing several times in THF. The product was filtered off, washed with a minimum amount of cold 2-methoxyethanol, then with THF. After drying in vacuo at 75° C., 2 g of the product was obtained in a yield of 66%; m.p. 210-215° C., UV (nm): 252 $\lambda_{max}$, 270 $\lambda_{max}$, 289 $\lambda_{max}$, 297 $\lambda_{sh}$, 337 $\lambda_{max}$. MS ESI+ 366.1 (M+H)$^+$, ESI− 364.1 (M−H)$^−$. NMR: $^1$H (500 MHz, DMSO-$d_6$) δ 1.23 (d, J=6.7 Hz, 6H, —CH—(C$\underline{H}_3$)$_2$); 3.44 (m, 1H, —C$\underline{H}$($CH_3$)$_2$); 4.75 (d, J=5.5 Hz, 2H, NH—C$\underline{H}_2$—); 7.08 (s, 1H, $H_{Ar}$); 7.48 (d, J=7.64 Hz, 2H, $H_{Ar}$); 7.60 (d, J=7.95 Hz, 2H, $H_{Ar}$); 7.70 (s, 1H, $H_{Ar}$); 8.22 (s, 1H, $H_{Ar}$); 9.21 (bs, 1H, —NH), 12.20 (bs, 1H, —NH), 13.75 (s, 1H, —SH). $^{13}$C (125 MHz, DMSO-$d_6$) δ 15.1, 21.8, 42.3, 64.9, 118.0, 120.3, 128.3, 129.0, 129.8, 135.5, 135.8. Anal. ($C_{18}H_{19}N_7S$) C, H, N, S.

3-isopropyl-7-[-4(pyrazin-2-yl)benzyl]amino-1(2)H-pyrazolo[4,3-d]pyrimidin-5-thiol (3.4.)

4-(Pyrazine-2-yl)benzylamine (0.93 g, 2.5 mmol) was dissolved in 50 mL of 2-methoxyethanol (6 mL) and 3-isopropyl-1(2)H-pyrazolo[4,3-d]pyrimidine-5,7-dithiol (2) (1.13 g, 5 mmol) was added under an atmosphere of nitrogen. The reaction mixture was refluxed for 9 hours. After cooling to about 10-15° C., the crystalline product was filtered off and washed with THF. After drying in vacuo at 75° C., 1.29 g of the product was obtained in 68% yield; m.p. 265-267° C., UV (nm): 256 $\lambda_{max}$, 292 $\lambda_{max}$, 301 $\lambda_{sh}$. MS ESI+ 378.2 (M+H)$^+$, ESI– 376.2 (M–H)$^-$. NMR: $^1$H (500 MHz, DMSO-$d_6$) δ 1.23 (d, J=6.4 Hz, 6H, —CH—(C$\underline{H}_3$)$_2$); 3.45 (bs, 1H, —C$\underline{H}$(CH$_3$)$_2$); 4.80 (d, J=4.3 Hz, 2H, NH—C$\underline{H}_2$—); 7.49 (bd, J=5.81 Hz, 2H, H$_{Ar}$); 8.10 (d, J=7.64 Hz, 2H, H$_{Ar}$); 8.58 (s, 1H, H$_{Ar}$); 8.69 (s, 1H, H$_{Ar}$); 9.23 (bs, 2H, H$_{Ar}$+—NH); 12.20 (bs, 1H, —NH), 13.75 (s, 1H, —SH). $^{13}$C (125 MHz, DMSO-$d_6$) δ 21.8, 42.6, 126.7, 128.0, 128.3, 134.5, 141.9, 143.3, 144.3, 151.2. Anal. ($C_{19}H_{19}N_7S$) C, H, N, S.

3-isopropyl-7-[-4(1H-imidazol-4-yl)benzyl]amino-1(2)H-pyrazolo[4,3-d]pyrimidin-5-thiol (3.5.)

4-(1H-imidazol-4-yl)benzylamine (1.03 g, 6 mmol) was dissolved in 2-methoxyethanol (7 mL), and 3-isopropyl-1(2)H-pyrazolo[4,3-D]pyrimidine-5,7-dithiol (2) (1.01 g, 4.5 mmol) was added under a nitrogen atmosphere. The reaction mixture was refluxed for 10 hours. After cooling to about 10-15° C., the crystalline product was filtered off and washed with THF. After drying in vacuo at 75° C., 1.29 g of the product was obtained in 68% yield; m.p. 285-290° C. (decomposition), UV (nm): 270 $\lambda_{max}$, 289 $\lambda_{max}$, 299 $\lambda_{ash}$, 336 $\lambda_{max}$. MS ESI+ 366.1 (M+H)$^+$, ESI– 364.1 (M–H)$^-$. NMR: $^1$H (500 MHz, DMSO-$d_6$) δ 1.23 (d, J=6.4 Hz, 6H, —CH—(C$\underline{H}_3$)$_2$); 3.12 (s, 1H, —CH—); 3.45 (bs, 1H, —C$\underline{H}$(CH$_3$)$_2$); 4.70 (d, J=4.3 Hz, 2H, NH—C$\underline{H}_2$—); 7.34 (bs, 2H, H$_{Ar}$); 7.67-7.71 (m, 3H, H$_{Ar}$); 8.09 (s, 1H, H$_{Ar}$). $^{13}$C (125 MHz, DMSO-$d_6$) δ 21.9; 42.6; 48.6; 64.9; 115.0; 124.5; 127.9; 136.6; 136.3. Anal. ($C_{18}H_{19}N_7S$) C, H, N, S.

5-(2-Hydroxy-1-ethyl)thio-3-isopropyl-7-[4-(2-pyridyl)benzyl]amino-1(2)H-pyrazolo[4,3-d]pyrimidine (4.1 a) To a solution of 3-isopropyl-7-[4-(2-pyridyl)benzyl]amino-1(2)H-pyrazolo[4,3-d]pyrimidine-5-thiol 3 (200 mg, 0.54 mmol) in DMF (6 mL) was added K$_2$CO$_3$ (0.2 g) and 2-bromoethanol (45 µL, 0.6 mmol) and the mixture was stirred at room temperature for 1 h. The reaction mixture was evaporated at temperature below 50° C. and the residue was partitioned between CHCl$_3$ and H$_2$O. The combined organic phase was dried (Na$_2$SO$_4$) and evaporated in vacuo. The product was crystallized from CHCl$_3$/Et$_2$O, 0.18 g, yield 80%.

b) To a stirred mixture of 3-isopropyl-7-[4-(2-pyridyl)benzyl]amino-1(2)H-pyrazolo[4,3-d]pyrimidine-5-thiol 3 (0.38 g, 1 mmol) and tetramethylammonium hydroxide (catalytic amount, 40 mg) in MeOH (6 mL), oxirane (80 mg, 1.8 mmol) in 2 mL MeOH was added and the mixture was stirred 16 h at room temperature. The product was isolated as precipitated after addition of water. The product was crystallized from CHCl$_3$/Et$_2$O, 0.36 g, yield 86%.

Analytical sample was recrystallized by the same procedure, m.p. 145-150° C., UV (nm): 246 $\lambda_{max}$, 275 sh 316 sh. MS ESI+ 443.2 (M+Na)$^+$, ESI– 419.3 (M–H)$^-$. $^1$H (500 MHz; CDCl$_3$): 1.21 (d, J=7.03 Hz, 6H, —CH(C$\underline{H}_3$)$_2$); 3.12-3.14 (m, 2H, —CH$_2$—); 3.17 (sept., J=7.03 Hz, 1H, —C$\underline{H}$(CH$_3$)$_2$); 3.78-3.80 (m, 2H, —CH$_2$—); 4.82 (bs, 2H, NH—C$\underline{H}_2$—); 7.04-7.07 (m, 1H, H$_{Ar}$); 7.30 (d, J=8.25 Hz, 2H, H$_{Ar}$); 7.45 (bs, 1H, —NH—); 7.53-7.59 (m, 2H, H$_{Ar}$); 7.80 (d, J=8.25 Hz, 2H, H$_{Ar}$); 8.47-8.48 (m, 1H, H$_{Ar}$); 11.73 (bs, 1H, —NH—). $^{13}$C (125 MHz; CDCl$_3$): 21.3; 26.0; 33.9; 43.8; 63.5; 119.9; 121.9; 126.6; 128.2; 136.5; 138.3; 138.6; 149.2; 156.1; 162.1. Anal. ($C_{22}H_{24}N_6OS$) C, H, N.

5-(Prop-2-en-1-yl)thio-3-isopropyl-7-[4-(2-pyridyl)benzyl]amino-1(2)H-pyrazolo[4,3-d]pyrimidine (4.2

To a suspension of 3-isopropyl-7-[4-(2-pyridyl)benzyl]amino-1(2)H-pyrazolo[4,3-d]pyrimidine-5-thiol 3 (0.38 g, 1.00 mmol) in H$_2$O (20 mL), 1N solution NaOH (1.4 mL) and allylbromide (0.13 mL, 1.1 mmol) were added and the mixture was stirred at room temperature for 6 h. The product was filtered off and recrystallized from CHCl$_3$/Et$_2$O, 0.28 g, yield 67%, mp 148-150° C. MS ESI+ 417.2 (M+H)$^+$, ESI– 415.3 (M–H)$^-$. $^1$H (500 MHz; DMSO-$d_6$): 1.36 (d, J=6.72 Hz, 6H, —CH(C$\underline{H}_3$)$_2$); 3.27 (sept., J=7.03 Hz, 1H, —C$\underline{H}$(CH$_3$)$_2$); 3.73 (d, J=7.03 Hz, 2H, —S—C$\underline{H}_2$—CH); 4.75 (bs, 2H, NH—C$\underline{H}_2$—); 5.01 (dd, J=9.78 Hz, J=0.92 Hz, 1H, C$\underline{H}_α$H$_β$=CH—); 5.22 (dd, J=16.96 Hz, J=1.53 Hz, 1H, CH$_α$$\underline{H}_β$=CH—); 5.94 (ddt, J=16.81 Hz, J=9.93 Hz, J=7.03 Hz, 1H, CH$_2$=C$\underline{H}$—CH$_2$—); 7.31 (qd, J=7.39 Hz, J=4.89 Hz, J=1.22 Hz, 1H, H$_{Ar}$); 7.47 (d, J=8.56 Hz, 2H, H$_{Ar}$); 7.84 (td, J=7.64 Hz, J=1.83 Hz, 1H, H$_{Ar}$); 7.91 (d, J=7.95 Hz, 1H, H$_{Ar}$); 8.05 (d, J=8.25 Hz, 2H, H$_{Ar}$); 8.26 (bs, 1H, —NH—CH$_2$—); 8.64 (qd, J=4.86 Hz, J=1.83 Hz, J=0.92 Hz, 1H, H$_{Ar}$); 12.56 (bs, 1H, —NH—). $^{13}$C (125 MHz; DMSO-$d_6$): 21.6; 25.8; 33.0; 42.9; 116.7; 120.0; 122.4; 126.5; 127.8; 134.9; 137.0; 137.5; 139.8; 149.4; 155.7; 160.1. Anal. ($C_{23}H_{24}N_6S$) C, H, N.

5-(2-Hydroxy-1-propyl)thio-3-isopropyl-7-[4-(2-pyridyl)benzyl]amino-1(2)H-pyrazolo[4,3-d]pyrimidine (4.3

To a stirred mixture of 3-isopropyl-7-[4-(2-pyridyl)benzyl]amino-1(2)H-pyrazolo[4,3-d]pyrimidine-5-thiol 3 (0.38 g, 1 mmol) and tetramethylammonium hydroxide (catalytic amount, 40 mg) in MeOH (6 mL), 2,2-dimethyloxirane (80 mg, 1.8 mmol) in MeOH (2 mL) was added and the mixture was stirred at room temperature for 6 h. The product was precipitated after adding of water, and it was finally purified by column chromatography, stepwise 1%, 2%, and 3% MeOH in CHCl$_3$. The product was crystallized from DCM/Et$_2$O, 0.30 g, yield 69%, m.p. 144-146° C. MS ESI+ 435.2 (M+H)$^+$, ESI– 433.3 (M–H)$^-$. $^1$H (500 MHz; CDCl$_3$): 1.21 (d, J=6.11 Hz, 6H, —CH(CH$_3$)$_2$); 1.25 (d, J=6.42 Hz, 3H); 3.05 (dd, J=14.98 Hz, J=6.72 Hz); 3.18 (sept., J=7.03 Hz, 1H, —CH(CH$_3$)$_2$); 3.25 (d, J=14.37 Hz, 1H); 4.18-4.21 (m, 1H); 4.66 (bs, 2H, —NH—CH$_2$—); 7.17-7.22 (m, 3H, H$_{Ar}$); 7.58 (d, J=7.95 Hz, 1H, H$_{Ar}$); 7.68-7.72 (m, 3H, H$_{Ar}$); 8.59 (d, J=4.89 Hz, 1H, H$_{Ar}$). $^{13}$C (125 MHz; CDCl$_3$): 21.5; 21.6; 22.7; 26.1; 39.8; 44.0; 69.0; 120.9; 122.3; 127.0; 128.0; 137.1; 138.1; 138.5; 149.2; 156.9; 163.4. Anal. ($C_{23}H_{26}N_6OS$) C, H, N.

5-(3-Hydroxy-2-butyl)thio-3-isopropyl-7-[4-(2-pyridyl)benzyl]amino-1(2)H-pyrazolo[4,3-d]pyrimidine (4.4

To a stirred mixture of 3-isopropyl-7-[4-(2-pyridyl)benzyl]amino-1(2)H-pyrazolo[4,3-d]pyrimidine-5-thiol 3 (0.38 g, 1 mmol) and tetramethylammonium hydroxide (catalytic amount, 40 mg) in MeOH (6 mL), E/Z-2,3-dimethyloxirane (130 mg, 1.8 mmol) in MeOH (2 mL) was added and the mixture was stirred at room temperature for 16 h. The product was precipitated after adding of water and it was finally purified by column chromatography, stepwise 1%, 2%, and 3% MeOH in CHCl$_3$. The product was crystallized from DCM/Et$_2$O, 0.25 g, yield 54%, m.p. 168-172° C. MS ESI+ 449.2 (M+H)$^+$, ESI– 447.3 (M–H)$^-$. $^1$H (500 MHz; CDCl$_3$): δ 1.29-1.26 (m, 6H, —CH—(CH$_3$)$_2$); 1.33 (d, J=6.4 Hz, 3H, —CH—CH$_3$); 1.43 (d, J=7.0 Hz, 3H, —CH—CH$_3$); 3.21-3.26 (m, 1H, —CH—(CH$_3$)$_2$); 3.52-3.55 (m, 1H, —CH—CH$_3$); 3.89-3.92 (m, 1H, —CH—CH$_3$); 4.73 (bs, 2H, NH—CH$_2$—); 7.23-7.21 (m, 1H, H$_{Ar}$); 7.26-7.28 (m, 2H, H$_{Ar}$); 7.64 (d, J=7.9 Hz, 1H, H$_{Ar}$); 7.73 (td, J=7.7, 1.7 Hz, 1H, H$_{Ar}$); 7.76-7.78 (m, 3H, H$_{Ar}$+NH—CH$_2$—); 8.64 (d, J=4.9 Hz, 1H, H$_{Ar}$). $^{13}$C (125 MHz, CDCl$_3$+DMSO-d$_6$) δ 17.5, 21.43, 21.46, 21.7, 26.1, 44.0, 48.3, 71.9, 120.1, 122.0, 126.8, 128.3, 136.6, 138.3, 138.6, 149.3, 156.3, 161.8.

5-(1-Hydroxy-2-butyl)thio-3-isopropyl-7-[4-(2-pyridyl)benzyl]amino-1(2)H-pyrazolo[4,3-d]pyrimidin (4.5

The precursor synthesis of 2-bromo-1-butanol was prepared from 2-bromobutanoic acid which was reduced by introducing gaseous B$_2$H$_6$ into THF solution at −10° C. for 5 h and then at 0° C. for 5 h and finally at room temperature for 2 h. The reaction was quenched by dropwise addition of an aqueous 50% HCOOH solution with stirring. The mixture was concentrated by evaporation at room temperature and 15 torr pressure. The residue was neutralized with an aqueous solution of NaHCO$_3$ until the evolution of CO$_2$. The product was extracted with EtOAc (ethyl acetate) and dried with MgSO$_4$. The volatiles were removed from the extract at three laboratory temperatures and a pressure of 15 torr. This crude product (=1.38 g/mL) was used for subsequent alkylation.

To a solution of 3-isopropyl-7-[4-(2-pyridyl)benzyl]amino-1(2)H-pyrazolo[4,3-d]pyrimidine-5-thiol 3 (0.225 g, 0.66 mmol) in DMF (5 mL), K$_2$CO$_3$ (0.2 g) and 2-bromo-1-butanol (120 mL, 1.0 mmol) were added. The reaction mixture was stirred at 50° C. for 8 h. The reaction mixture was evaporated at temperature below 50° C. and the residue was partitioned between EtOAc and H$_2$O. DMSO was evaporated to dryness and the residue was partitioned between CHCl$_3$ and H$_2$O. The combined organic phase was dried with magnesium sulfate and evaporated under vacuum. The product was purified by column chromatography, stepwise 2%, 3% and 4% MeOH in CHCl$_3$. Product was crystallized from the combined organic phase was dried (MgSO$_4$) and the product was crystallized from abs. EtOH, 0.07 g, yield 22%, m.p 126-129° C. MS ESI+ 449.1 (M+H)$^+$, ESI– 447.1 (M–H)$^-$. $^1$H (500 MHz, CDCl$_3$): δ 0.95 (t, J=7.4 Hz, 3H, —CH$_3$); 1.34-1.38 (m, 6H, —CH(CH$_3$)$_2$); 1.54-1.62 (m, 1H, —CH$_\alpha$H$_\beta$—CH$_3$); 1.80-1.87 (m, 1H, —CH$_\alpha$H$_\beta$—CH$_3$); 3.23 (m, J=6.9 Hz, 1H, —CH(CH$_3$)$_2$); 3.50-3.52 (m, 1H, —S—CH—); 3.70-3.74 (m, 2H, —CH$_2$—OH); 4.76 (t, J=4.9 Hz, 2H, NH—CH$_2$—); 4.86 (bs, 1H, —OH), 7.32-7.34 (m, 1H, H$_{Ar}$); 7.44-7.51 (m, 2H, H$_{Ar}$); 7.84-7.94 (m, 2H, H$_{Ar}$); 8.00-8.08 (m, 3H, H$_{Ar}$+—NH); 8.64-8.65 (m, 1H, H$_{Ar}$); 12.16 (s, 1H, —NH). $^{13}$C (125 MHz, DMSO-d$_6$) δ 11.3, 21.5, 21.6, 21.7, 23.5, 24.9, 26.3, 40.4, 43.1, 48.4, 63.0, 120.0, 120.3, 122.3, 122.5, 126.3, 126.6, 127.6, 128.0, 130.4, 137.1, 137.6, 138.6, 139.5, 139.9, 140.5, 148.5, 148.7, 149.4, 153.7, 155.6, 155.8, 161.0. Anal. (C$_{24}$H$_{28}$N$_6$OS) C, H, N.

5-(2-Carbamoyl-1-ethyl)thio-3-isopropyl-7-[4-(2-pyridyl)benzyl]amino-1(2)H-pyrazolo[4,3-d]pyrimidine (4.6

To a solution of 3-isopropyl-7-[4-(2-pyridyl)benzyl]amino-1(2)H-pyrazolo[4,3-d]pyrimidine-5-thiol 3.1. (200 mg, 0.54 mmol) in DMF (6 mL), K$_2$CO$_3$ (0.2 g) and 3-chloropropionamide (65 mg, 0.6 mmol) were added. The reaction mixture was stirred at 50° C. for 8 h. The reaction mixture was evaporated at temperature below 50° C. and the residue was partitioned between EtOAc and H$_2$O. The combined organic phase was dried (Na$_2$SO$_4$) and the product was crystallized from EtOAc, 0.11 g, yield 46%, m.p. 137-140° C.: MS ESI+ 448.2 (M+H)$^+$ 100%, 470.2 (M+Na)$^+$ 30%, ESI– 446.3 (M–H)$^-$ 100%, 893.3 (2M–H)$^-$ 30%. $^1$H (500 MHz; DMSO-d$_6$): 1.36 (d, J=7.03 Hz, 6H, —CH(CH$_3$)$_2$); 2.50 (t, J=7.03 Hz, 2H, O═C—CH$_2$—); 3.20 (t, J=7.03 Hz, 2H, —S—CH$_2$—); 3.26 (sept., J=6.72 Hz, 1H, —CH(CH$_3$)$_2$); 4.75 (bs, 2H, —NH—CH$_2$—); 6.78 (bs, 1H, —C(O)—NH$_\alpha$H$_\beta$); 7.26 (bs, 1H, —C(O)—NH$_\alpha$H$_\beta$); 7.31 (qd, J=7.41 Hz, J=4.74 Hz, J=1.22 Hz, 1H, H$_{Ar}$); 7.48 (d, J=8.25 Hz, 2H, H$_{Ar}$); 7.84 (td, J=7.64 Hz, J=1.83 Hz, 1H, H$_{Ar}$); 7.91 (d, J=7.95 Hz, 1H, H$_{Ar}$); 8.04 (d, J=8.25 Hz, 2H, H$_{Ar}$); 8.46 (bs, 1H, —NH—); 8.63 (bd, J=4.89 Hz, 1H, H$_{Ar}$). $^{13}$C (125 MHz; DMSO-d$_6$): 21.6; 26.0; 35.2; 42.9; 120.0; 122.4; 125.3; 126.5; 127.8; 131.9; 137.1; 137.4; 139.9; 149.4; 155.7; 160.4; 172.7. Anal. (C$_{23}$H$_{25}$N$_7$OS) C, H, N.

5-(Carbamoylmethyl)thio-3-isopropyl-7-[4-(2-pyridyl)benzyl]amino-1(2)H-pyrazolo[4,3-d]pyrimidine (4.7

To a solution of 3-isopropyl-7-[4-(2-pyridyl)benzyl]amino-1(2)H-pyrazolo[4,3-d]pyrimidine-5-thiol 3.1. (200 mg, 0.54 mmol) in DMF (6 mL) K$_2$CO$_3$ (0.09 g) and 2-chloroacetamide (51 mg, 0.54 mmol) were added. The reaction mixture was stirred at room temperature for 2 h. The reaction mixture was evaporated at temperature below 50° C. and the residue was triturated with water and crystallized from water, 0.13 g, yield 56%, m.p. 220-235° C. MS ESI+ 434.2 (M+H)$^+$. ESI– 432.3 (M–H)$^-$. $^1$H (500 MHz; DMSO-d$_6$): 1.35 (d, J=7.03 Hz, 6H, —CH(CH$_3$)$_2$); 3.26 (sept., J=7.03 Hz, 1H, —CH(CH$_3$)$_2$); 3.72 (s, 2H, —S—CH$_2$—); 4.76 (bs, 2H, —NH—CH$_2$—); 7.02 (bs, 1H, —C(O)—NH$_\alpha$H$_\beta$); 7.31 (qd, J=6.42 Hz, J=4.89 Hz, J=0.92 Hz, 1H, H$_{Ar}$); 7.42 (bs, 1H, —C(O)—NH$_\alpha$H$_\beta$); 7.50 (d, J=7.95 Hz, 2H, H$_{Ar}$); 7.85 (td, J=7.64 Hz, J=1.53 Hz, 1H, H$_{Ar}$); 7.92 (d, J=7.95 Hz, 1H, H$_{Ar}$); 8.05 (d, J=7.95 Hz, 2H, H$_{Ar}$); 8.34 (bs, 1H, —NH—); 8.64 (bd, J=4.28 Hz, 1H, H$_{Ar}$). $^{13}$C (125 MHz; DMSO-d$_6$): 21.6; 25.8; 34.4; 42.9; 120.0; 122.4; 126.5; 128.0; 137.0; 137.5; 139.8; 149.4; 155.7; 160.1; 170.3. Anal. (C$_{22}$H$_{23}$N$_7$OS) C, H, N.

5-(3-Hydroxy-1-propyl)thio-3-isopropyl-7-[4-(2-pyridyl)benzyl]amino-1(2)H-pyrazolo[4,3-d]pyrimidine (4.8

To a solution of 3-isopropyl-7-[4-(2-pyridyl)benzyl]amino-1(2)H-pyrazolo[4,3-d]pyrimidine-5-thiol 3 (200 mg, 0.54 mmol) in DMF (6 mL), K$_2$CO$_3$ (0.1 g) and 3-bromopropanol (54 L, 0.6 mmol) was added and the mixture was stirred at room temperature for 3 h. The reaction mixture was evaporated at temperature below 50° C. and the residue was partitioned between CHCl$_3$ and H$_2$O. The combined organic phase was dried (Na$_2$SO$_4$) and evaporated in vacuo. The product was purified by column chromatography, stepwise 2%, 3% and 4% MeOH in CHCl$_3$. The product was crystallized from CHCl$_3$/Et$_2$O, 0.15 g, yield 66%, mp 150-152° C.: MS ESI+ 435.2 (M+H)$^+$, ESI− 433.3 (M−H)$^-$. $^1$H (500 MHz; CDCl$_3$+DMSO-d$_6$): 1.20 (d, J=7.03 Hz, 6H, —CH(CH$_3$)$_2$); 1.72-1.74 (m, 2H, —CH$_2$—CH$_2$—CH$_2$—); 3.13 (t, J=5.50 Hz, 2H, —S—CH$_2$—); 3.18 (sept., J=7.03 Hz, 1H, —CH(CH$_3$)$_2$); 3.49-3.50 (m, 2H, —CH$_2$—OH); 4.61 (bs, 2H, —NH—CH$_2$—); 4.75 (bs, 1H, —OH); 7.03-7.06 (m, 1H, H$_{Ar}$); 7.30 (d, J=7.95 Hz, 2H, H$_{Ar}$); 7.50-7.58 (m, 3H, H$_{Ar}$+—NH—CH$_2$—); 7.79 (d, J=7.03 Hz, 2H, H$_{Ar}$); 8.46 (d, J=4.58 Hz, 1H, H$_{Ar}$); 11.64 (bs, 1H, —NH—). $^{13}$C (125 MHz; CDCl$_3$+DMSO-d$_6$): 21.3; 25.7; 26.4; 32.6; 43.7; 58.5; 119.9; 121.8; 126.6; 128.2; 136.4; 138.2; 138.6; 149.1; 156.1; 162.5. Anal. (C$_{23}$H$_{26}$N$_6$OS) C, H, N.

5-(2-Amino-1-ethyl)thio-3-isopropyl-7-[4-(2-pyridyl)benzyl]amino-1(2)H-pyrazolo[4,3-d]pyrimidine (4.9 a) To a stirred mixture of 3-isopropyl-7-[4-(2-pyridyl)benzyl]amino-1(2)H-pyrazolo[4,3-d]pyrimidine-5-thiol 3.1. (1.0 g, 2.66 mmol), 3.1 mL of aq. 48% solution HBr in DMF (20 mL) and aziridine (0.42 mL, 8 mmol) were added dropwise. The mixture was stirred at room temperature for 24 h. The reaction mixture was neutralized by aq. solution of Na$_2$CO$_3$ and the crude product was isolated as a precipitate.

b) To a solution of 3-isopropyl-7-[4-(2-pyridyl)benzyl]amino-1(2)H-pyrazolo[4,3-d]pyrimidine-5-thiol 3.1. (1 g, 2.66 mmol) in DMF (30 mL), K$_2$CO$_3$ (0.5 g) and 2-(Boc-amino)ethylbromide (0.61 g, 2.71 mmol) was added. The reaction mixture was stirred at room temperature for 16 h. The product was isolated as a precipitate after addition of water. The precipitate was dissolved in 25 ml of 2N aq. HCl and de-bocylation reaction was carried out overnight at room temperature. The reaction mixture was neutralized by aq. solution of Na$_2$CO$_3$ and the crude product was isolated as a precipitate.

The product was purified by column chromatography, stepwise 3%, 5%, 7% and 10% MeOH in CHCl$_3$ with trace of aq. NH$_4$OH. Chromatography provided (after evaporation in vacuo) amorphous colorless glass foam, 0.72 g, yield 65% for process a), 0.75 g, yield 67% for process b). MS ESI+420.2 (M+H)$^+$ 100%, 839.3 (2M+H)$^+$ 15%, ESI− 418.2 (M−H)$^-$. $^1$H (500 MHz; DMSO-d$_6$): 1.36 (d, J=7.03 Hz, 6H, —CH(CH$_3$)$_2$); 2.89 (t, J=6.72 Hz, 2H, NH$_2$—CH$_2$—); 3.12 (t, J=6.72 Hz, 2H, —CH$_2$—S—); 3.27 (sept., J=7.03 Hz, 1H, —CH(CH$_3$)$_2$); 4.76 (bs, 2H, NH—CH$_2$—); 7.31 (qd, J=7.34 Hz, J=4.89 Hz, J=0.92 Hz, 1H, H$_{Ar}$); 7.48 (d, J=8.25 Hz, 2H, H$_{Ar}$); 7.84 (td, J=7.95 Hz, J=1.83 Hz, 1H, H$_{Ar}$); 7.91 (d, J=8.25 Hz, 1H, H$_{Ar}$); 8.05 (d, J=8.25 Hz, 2H, H$_{Ar}$); 8.45 (bt, J=5.81 Hz, 1H, —NH—CH$_2$—); 8.63 (qd, J=4.74 Hz, J=1.53 Hz, J=0.92 Hz, 1H, H$_{Ar}$). $^{13}$C (125 MHz; DMSO-d$_6$): 21.6; 25.8; 32.7; 40.8; 42.9; 120.0; 122.4; 126.5; 127.8; 137.0; 137.4; 138.5; 139.9; 149.4; 155.7; 160.3. Anal. (C$_{22}$H$_{25}$N$_7$S) C, H, N.

5-(2-Guanidino-1-ethyl)thio-3-isopropyl-7-[4-(2-pyridyl)benzyl]amino-1(2)H-pyrazolo[4,3-d]pyrimidine (4.10

To a solution of 5-(2-amino-1-ethyl)thio-3-isopropyl-7-[4-(2-pyridyl)benzyl]amino-1(2)H-pyrazolo[4,3-d]pyrimidine 4.9. (0.35 g, 0.84 mmol) in DMF (2 mL) and DIEA (0.30 mL, 1.7 mmol), 1H-pyrazole-1-carboxamidine hydrochloride (0.143 g, 0.95 mmol) was added and the reaction mixture was stirred at room temperature for 2 h. The reaction mixture was evaporated at temperature below 50° C. and the residue was partitioned between CHCl$_3$ and H$_2$O. The combined organic phase was dried with sodium sulfate and evaporated in vacuo. The product was purified by column chromatography, stepwise 10%, 12% and 14% MeOH in CHCl$_3$ with trace of aq. NH$_4$OH. Chromatography provided (after evaporation in vacuo) amorphous colorless glass foam, 0.225 g, yield 58%. MS ESI+ 231.7 (M+2H)$^{2+}$ 100%, 462.1 (M+H)$^+$ 30%, ESI− 460.1 (M−H)$^-$. NMR: mixture of tautomers: $^1$H (500 MHz, DMSO-d$_6$) δ 1.34 (d, J=7.0 Hz, 6H, —CH(CH$_3$)$_2$), 3.15 (d, J=4.6 Hz, 1H), 3.19 (t, J=6.3 Hz, 2H, —CH$_2$—CH$_2$—), 3.24 (sept., J=6.9 Hz, 1H, —CH(CH$_3$)$_2$), 3.36 (s, 2H), 3.42-3.46 (m, 2H, —CH$_2$—CH$_2$—), 4.76 (d, J=5.2 Hz, 2H, NH—CH$_2$—), 7.32 (dd, J=7.0, 5.2 Hz, 1H, H$_{Ar}$), 7.45 (s, 1H, H$_{Ar}$), 7.50 (d, J=7.9 Hz, 2H, H$_{Ar}$), 7.83-7.87 (m, 2H, H), 7.93 (d, J=7.9 Hz, 1H, H$_{Ar}$), 8.05 (d, J=7.9 Hz, 2H, H$_{Ar}$), 8.64 (d, J=4.3 Hz, 1H), 8.93 (s, 1H, —NH), 13.05 (s, 1H, —NH). $^{13}$C (125 MHz, DMSO-d$_6$) δ 21.76, 26.30, 29.43, 40.56, 42.96, 48.59, 120.13, 120.77, 122.52, 126.58, 127.66, 127.82, 137.22, 137.51, 139.70, 139.83, 148.46, 148.94, 149.51, 155.77, 156.95, 159.73. Anal. (C$_{23}$H$_{27}$N$_9$S) C, H, N.

5-(2-Ureido-1-ethyl)thio-3-isopropyl-7-[4-(2-pyridyl)benzyl]amino-1(2)H-pyrazolo[4,3-d]pyrimidine (4.11

To a solution of 5-(2-amino-1-ethyl)thio-3-isopropyl-7-[4-(2-pyridyl)benzyl]amino-1(2)H-pyrazolo[4,3-d]pyrimidine 4.9. (0.35 g, 0.84 mmol) in AcOH (6 mL) solution of potassium cyanate (0.13 g, 1.6 mmol) in 1 mL of water was added dropwise and the reaction mixture was stirred at room temperature for 4 h. The reaction mixture was evaporated at temperature below 50° C. and the residue was partitioned between CHCl$_3$ and H$_2$O. The combined organic phase was dried with sodium sulfate and evaporated in vacuo. The product was purified by column chromatography, stepwise 3%, 5%, 7% and 10% MeOH in CHCl$_3$. Chromatography provided (after evaporation under vacuum) amorphous colorless glass foam, 0.12 g, yield 31%. MS ESI+ 232.5 (M+2H)$^{2+}$ 100%, 463.1 (M+H)$^+$ 60%, ESI− 461.1 (M−H)$^-$. $^1$H (500 MHz, DMSO-d$_6$) δ 1.35 (d, J=6.7 Hz, 6H, —CH(CH$_3$)$_2$), 3.03-3.08 (m, 2H, —CH$_2$—CH$_2$—), 3.22-3.29 (m, 3H, —CH(CH$_3$)$_2$+—CH$_2$—CH$_2$—), 4.77 (s, 2H, NH—CH$_2$—), 5.48 (s, 2H, —NH2), 6.15 (s, 1H, —NH), 7.31-7.32 (m, 1H, H$_{Ar}$), 7.50 (d, J=7.3 Hz, 2H, H$_{Ar}$), 7.86 (t, J=7.0 Hz, 1H, H$_{Ar}$), 7.92-7.94 (m, 1H, H$_{Ar}$), 8.08 (d, J=6.7 Hz, 2H, H$_{Ar}$), 8.64 (s, 1H, H$_{Ar}$), 12.20 (s, 1H, —NH). $^{13}$C-NMR (125 MHz, DMSO-d$_6$) δ 21.70, 26.35, 31.07, 35.78, 43.19, 62.79, 79.18, 120.14, 122.57, 126.67, 128.10, 137.23, 139.67, 148.83, 149.52, 155.73, 158.54, 160.43. Anal. (C$_{23}$H$_{26}$N$_8$OS) C, H, N.

5-(2-Acetylamino-1-ethyl)thio-3-isopropyl-7-[4-(2-pyridyl)benzyl]amino-1(2)H-pyrazolo[4,3-d]pyrimidine (4.12

The title compound was isolated by column chromatography as a byproduct of synthesis of 5-(2-ureido-1-ethyl)thio-3-isopropyl-7-[4-(2-pyridyl)benzyl]amino-1(2)H-pyrazolo[4,3-d]pyrimidine 4.11., amorphous colorless glass foam, 0.08 g, yield 20%. MS ESI+ 232.5 (M+2H)$^{2+}$ 100%, 463.1 (M+H)$^+$60%, ESI− 461.1 (M−H)$^-$. NMR: mixture of tautomers: $^1$H (500 MHz, CDCl$_3$) δ 1.37 (d, J=7.0 Hz, 6H, —CH(C$\underline{H}_3$)$_2$), 1.79-1.78 (m, 3H, —CH$_3$), 3.19 (t, J=5.8 Hz, 2H, —C$\underline{H}_2$—CH$_2$—), 3.32 (sept, J=7.0 Hz, 1H, —C$\underline{H}$(CH$_3$)$_2$), 3.49 (d, J=5.5 Hz, 2H, —CH$_2$—C$\underline{H}_2$—), 4.73 (d, J=3.7 Hz, 2H, NH—C$\underline{H}_2$—), 7.10 (bs, 1H, —NH), 7.22-7.19 (m, 1H, H$_{Ar}$), 7.36 (d, J=8.3 Hz, 2H, H$_{Ar}$), 7.63 (d, J=7.9 Hz, 1H, H$_{Ar}$), 7.74-7.71 (m, 1H, H$_{Ar}$), 7.83 (d, J=8.3 Hz, 2H, H$_{Ar}$), 8.62 (d, J=4.9 Hz, 1H, H$_{Ar}$). $^{13}$C (125 MHz, CDCl$_3$) δ 21.83, 23.13, 26.35, 30.31, 40.56, 44.29, 120.74, 122.33, 127.13, 128.17, 137.18, 138.25, 138.86, 147.35, 149.33, 150.18, 156.76, 161.81, 171.31.

5-(2-Amino-2-methyl-1-propyl)thio-3-isopropyl-7-[4-(2-pyridyl)benzyl]amino-1(2)H-pyrazolo[4,3-d]pyrimidin (4.13

To a stirred mixture of 3-isopropyl-7-[4-(2-pyridyl)benzyl]amino-1(2H)-pyrazolo[4,3-d]pyrimidine-5-thiol 3.1. (3 mL), 3 mL of 48% HBr, DMF (3 mL) and H$_2$O (10 mL) was added dropwise at room temperature and then 2,2-dimethylaziridine (1.5 mL, 20 mmol, synthesized according Org Synth. Vol. 3, p. 148.). The reaction mixture was stirred at room temperature for 24 h, then neutralized with aqueous saturated Na$_2$CO$_3$, and the crude product was isolated as a precipitate. The product was purified by column chromatography successively with 3%, 5%, 7% and 10% MeOH in CHCl$_3$ with a small amount of aq. NH$_4$OH. Concentration in vacuo gave 1.6 g of amorphous, colorless, solid foam product in 36% yield. MS ESI+ 448.2 (M+H)$^+$, ESI– 446.2 (M–H)$^-$. NMR: $^1$H (500 MHz; DMSO-d$_6$): 1.24 (s, 6H, 2×—CH$_3$); 1.29 (d, J=7.03 Hz, 6H, —CH—(CH$_3$)$_2$); 3.43 (t, J=6.11 Hz, 1H, —CH—(CH$_3$)$_2$); 3.60 (s, 2H, —CH$_2$—); 4.97 (d, J=5.20 Hz, 2H, —NH—CH$_2$—); 7.62 (d, J=8.56 Hz, 2H, ArH); 7.76 (t, J=6.42 Hz, 1H, ArH); 8.05 (d, J=8.56 Hz, 2H, ArH); 8.24 (d, J=7.95 Hz, 1H, ArH); 8.36 (t, J=7.49 Hz, 1H, ArH); 8.49 (bs, 2H, —NH$_2$); 8.76 (d, J=5.2 Hz, 1H, ArH). $^{13}$C (125 MHz; DMSO-d$_6$): 22.3; 25.0; 25.7; 31.2; 34.5; 39.2; 44.0; 49.2; 54.4; 124.3; 125.1; 128.5; 128.7; 132.5; 141.9; 144.1; 144.9; 152.9; 160.2. Anal. (C$_{24}$H$_{29}$N$_7$S) C, H, N.

5-(2-Hydroxycyclohexyl1-yl)thio-3-isopropyl-7-[4-(2-pyridyl)benzyl]amino-1(2)H-pyrazolo[4,3-d]pyrimidine (4.14

To a stirred mixture of 3-isopropyl-7-[4-(2-pyridyl)benzyl]amino-1(2)H-pyrazolo[4,3-d]pyrimidine-5-thiol 3.1. (0.38 g, 1 mmol) and tetramethylammonium hydroxide (catalytic amount, 80 mg) in MeOH (6 mL) 1,2-epoxycyclohexane (0.12 mL, 1.15 mmol) in MeOH (2 mL) was added and the mixture was stirred at 40° C. for 7 h. The reaction mixture was evaporated at temperature below 50° C. and the residue was partitioned between 2-methyltetrahydrofuran and H$_2$O. The combined organic phase was dried with magnesium sulfate and evaporated under vacuum. The product was purified by column chromatography, stepwise 2%, 3% and 4% MeOH in CHCl$_3$. Chromatography provided (after evaporation under vacuum) amorphous colorless glass foam, 0.22 g, yield 46%. MS ESI+ 475.1 (M+H)$^+$, ESI– 473.1 (M–H)$^-$. $^1$H (500 MHz; CDCl$_3$): 1.17 (d, J=7.03 Hz, 3H, —C$\underline{H}_3$); 1.19-1.20 (m, 2H, —C$\underline{H}_\alpha$$\underline{H}_\beta$—CH$_2$—CH—S—+—C$\underline{H}_\alpha$$\underline{H}_\beta$—CH$_2$—CH—OH); 1.23 (d, J=7.03 Hz, 3H, —C$\underline{H}_3$); 1.31-1.39 (m, 2H, —C$\underline{H}_\alpha$$\underline{H}_\beta$—CH—S—+—C$\underline{H}_\alpha$$\underline{H}_\beta$—CH—OH); 1.67-1.69 (m, 2H, —CH$_\alpha$$\underline{H}_\beta$—CH$_2$—CH—S—+—CH$_\alpha$$\underline{H}_\beta$—CH$_2$—CH—OH); 2.06-2.16 (m, 2H, —CH$_\alpha$$\underline{H}_\beta$—CH—S—+—CH$_\alpha$$\underline{H}_\beta$—CH—OH); 3.17 (sept., 1H, —C$\underline{H}$(CH$_3$)$_2$); 3.40-3.46 (m, 1H, —S—C$\underline{H}$—); 3.54 (td, J=10.70 Hz, J=4.26 Hz, 1H, —C$\underline{H}$—OH); 4.64 (bs, 2H, —NH—C$\underline{H}_2$—); 7.15-7.19 (m, 3H, H$_{Ar}$); 7.31 (bs, 1H, —N$\underline{H}$—CH$_2$—); 7.57 (d, J=7.95 Hz, 1H, H$_{Ar}$); 7.66-7.70 (m, 3H, H$_{Ar}$); 8.57 (d, J=4.89 Hz, 1H, H). $^{13}$C (125 MHz; CDCl$_3$): 21.3; 21.7; 24.0; 26.0; 26.2; 30.2; 31.5; 36.5; 44.0; 51.2; 77.4; 120.8; 121.1; 127.0; 127.9; 136.9; 138.2; 138.6; 149.3; 157.0; 163.6. Anal. (C$_{26}$H$_{30}$N$_6$OS) C, H, N.

5-(2-Hydroxy-1-butyl)thio-3-isopropyl-7-[4-(2-pyridyl)benzyl]amino-1(2)H-pyrazolo[4,3-d]pyrimidine (4.15

To a stirred mixture of 3-isopropyl-7-[4-(2-pyridyl)benzyl]amino-1(2)H-pyrazolo[4,3-d]pyrimidine-5-thiol 3.1. (0.38 g, 1 mmol) and tetramethylammonium hydroxide (catalytic amount, 60 mg) in MeOH (6 mL), 1,2-epoxybutane (0.1 mL, 1.15 mmol) in MeOH (2 mL) was added and the mixture was stirred at room temperature for 10 h. The product was precipitated after addition of water and then was purified by column chromatography, stepwise 1%, 2%, and 3% MeOH in CHCl$_3$. Chromatography provided (after evaporation under vacuum) amorphous colorless glass foam, 0.28 g, yield 62%. MS ESI+ 449.2 (M+H)$^+$ 20%, 471.3 (M+Na)$^+$ 100%, ESI– 447.2 (M–H)$^-$. $^1$H (500 MHz; CDCl$_3$): 0.88 (t, J=7.34 Hz, 3H, —CH$_3$); 1.18 (d, J=5.83 Hz, 6H, —CH(CH$_3$)$_2$); 1.51-1.63 (m, 2H, —CH—CH$_2$—CH$_3$); 3.07 (dd, J=14.98 Hz, J=7.03, 1H, —S—CH$_\alpha$H$_\beta$CH—); 3.16 (sept., J=6.72 Hz, 1H, —CH(CH$_3$)$_2$); 3.25 (d, J=14.67 Hz, 1H, —S—CH$_\alpha$H$_\beta$CH—); 3.86-3.91 (m, 1H, —CH—OH); 4.63 (bs, 2H, —NH—CH$_2$—); 7.14-7.18 (m, 3H, H$_{Ar}$); 7.56 (d, J=7.95 Hz, 1H, H$_{Ar}$); 7.65-7.69 (m, 3H, H$_{Ar}$); 8.55 (d, J=3.67 Hz, 1H, H$_{Ar}$). $^{13}$C (125 MHz; CDCl$_3$): 9.8; 21.4; 21.5; 26.1; 29.4; 37.6; 44.0; 74.3; 120.9; 122.2; 127.0; 127.9; 137.0; 138.1; 138.5; 149.2; 156.9; 163.5. Anal. (C$_{24}$H$_{28}$N$_6$OS) C, H, N.

5-(2-Hydroxycyclopentyl)thio-3-isopropyl-7-[4-(2-pyridyl)benzyl]amino-1(2)H-pyrazolo[4,3-d]pyrimidine (4.16

To a stirred mixture of 3-isopropyl-7-[4-(2-pyridyl)benzyl]amino-1(2)H-pyrazolo[4,3-d]pyrimidine-5-thiol 3.1. (0.38 g, 1 mmol) and tetramethylammonium hydroxide (catalytic amount, 80 mg) in MeOH (6 mL), 1,2-epoxycyclopentane (0.10 mL, 1.15 mmol) in MeOH (2 mL) was added and the mixture was stirred at 40° C. for 7 h. The reaction mixture was evaporated at temperature below 50° C. and the residue was partitioned between 2-methyltetrahydrofuran and H$_2$O. The combined organic phase was dried with magnesium sulfate and evaporated under vacuum. The product was purified by column chromatography, stepwise 2%, 3% and 4% MeOH in CHCl$_3$. Product was crystallized from CHCl$_3$, 0.25 g, yield 54%, mp 148-150° C. MS ESI+ 461.1 (M+H)$^+$, ESI– 459.1 (M–H)$^-$. $^1$H (500 MHz; CDCl$_3$): 1.42 (d, J=6.42 Hz, 3H, —C$\underline{H}_3$); 1.19 (d, J=6.72 Hz, 3H, —CH$_3$); 1.44-1.51 (m, 1H, —S—CH—C$\underline{H}_\alpha$H$_\beta$—); 1.62-1.75 (m, 3H, —CH$_2$—CH$_2$—CH$_2$—+HO—CH—CH$_\alpha$H$_\beta$—); 2.01-2.10 (m, 2H, —S—CH—CH$_\alpha$H$_\beta$—+HO—CH—CH$_\alpha$$\underline{H}_\beta$—); 3.15 (sept., J=7.03 Hz, 1H, —C$\underline{H}$(CH$_3$)$_2$); 3.58-3.63 (m, 1H, —S—C$\underline{H}$—CH$_2$); 4.18-4.22 (m, 1H, HO—C$\underline{H}$—CH$_2$—); 4.65 (bs, 2H, NH—C$\underline{H}_2$—); 5.01 (dd, J=9.78 Hz, J=0.92 Hz, 1H, CH$_\alpha$$\underline{H}_\beta$=CH—); 5.22 (dd, J=16.96 Hz, J=1.53 Hz, 1H, C$\underline{H}_\beta$=CH—); 7.16-7.24 (m, 3H, H$_{Ar}$); 7.58-7.59 (m, 1H, H$_{Ar}$); 7.67-7.72 (m, 3H, H$_{Ar}$); 8.56 (bs, 1H, H$_{Ar}$). $^{13}$C (125 MHz; CDCl$_3$): 21.3; 21.8; 22.7; 25.8; 29.7; 34.4; 44.2; 50.6;

82.7; 120.8; 122.3; 127.1; 128.2; 137.1; 138.3; 138.4; 149.3; 156.8; 164.4. Anal. ($C_{25}H_{28}N_6OS$) C, H, N.

5-(2-Hydroxy-2-methyl-1-propyl)thio-3-isopropyl-7-[4-(2-pyridyl)benzyl]amino-1(2)H-pyrazolo[4,3-d]pyrimidine (4.17 a) To a solution of 3-isopropyl-7-[4-(2-pyridyl)benzyl]amino-1(2)H-pyrazolo[4,3-d]pyrimidine-5-thiol 3.1. (0.38 g, 1 mmol) in DMSO (10 mL), $K_2CO_3$ (0.6 g) and 2-bromo-3-methyl-1-butanol (0.25 g, 1.5 mmol) were added and the mixture was stirred at room temperature for 48 h. The reaction mixture was evaporated at temperature below 50° C. and the residue was partitioned between $CHCl_3$ and $H_2O$. The crude product was obtained after evaporating the combined organic phase.

b) To a stirred mixture of 3-isopropyl-7-[4-(2-pyridyl)benzyl]amino-1(2)H-pyrazolo[4,3-d]pyrimidine-5-thiol 3.1. (0.38 g, 1 mmol), and tetramethylammonium hydroxide (catalytic amount, 40 mg) in MeOH (6 mL), 1,2-epoxy-2-methylpropane (0.12 mL, 1.3 mmol) in MeOH (2 mL) was added and the mixture was stirred at room temperature for 7 h. The crude product was isolated as a precipitate after adding water.

The product was purified by column chromatography, stepwise 2%, 3% and 4% MeOH in $CHCl_3$. Chromatography provided (after evaporation under vacuum) amorphous colorless glass foam, 0.24 g, yield 54%, in the case of synthesis a) and 0.28 g, yield 62%, in the case of synthesis b). MS ESI+449.1 (M+H)+, ESI– 447.1 (M–H)–. $^1$H (500 MHz; DMSO-$d_6$): 1.35-1.38 (m, 6H, —CH(C$\underline{H}_3$)$_2$); 3.21-3.27 (m, 4H, —C$\underline{H}$(CH$_3$)$_2$, —CH$_3$); 4.69-4.80 (m, 2H, NH—C$\underline{H}_2$—); 5.29-5.34 (m, 2H, —S—CH$_2$—); 7.31-7.33 (m, 1H, H$_{Ar}$); 7.45-7.52 (m, 2H, H$_{Ar}$); 7.83-7.86 (m, 1H, H$_{Ar}$); 7.88-7.93 (m, 1H, H$_{Ar}$); 8.00-8.08 (m, 2H, H$_{Ar}$); 8.63-8.64 (m, 1H, H$_{Ar}$); 12.21 (bs, —NH—, form I); 13.79 (bs, —NH—, form II). $^{13}$C (125 MHz; DMSO-$d_6$): mixture of two tautomeric forms 21.5; 21.7; 24.8; 26.2; 42.5; 43.2; 55.9; 73.3; 120.0 120.6; 122.3; 122.4; 126.3; 126.6; 127.6; 128.0; 137.1; 137.7; 139.4; 139.8; 148.7; 148.9; 149.4; 153.9; 155.6; 155.8; 159.2. Anal. ($C_{24}H_{28}N_6OS$) C, H, N.

5-(2,3-Dihydroxy-1-propyl)thio-3-isopropyl-7-[4-(2-pyridyl)benzyl]amino-1(2)H-pyrazolo[4,3-d]pyrimidine (4.18

To a solution of 3-isopropyl-7-[4-(2-pyridyl)benzyl]amino-1(2)H-pyrazolo[4,3-d]pyrimidine-5-thiol 3.1. (0.38 g, 1 mmol) and tetramethylammonium hydroxide (0.11 g) in DMF (3 mL), 3-chloro-1,2-propanediol (127 L, 1.5 mmol) was added and the mixture was stirred at room temperature for 24 h. The crude product was precipitated after adding water and then was purified by column chromatography, stepwise 2%, 3%, 4% and 5% MeOH in $CHCl_3$. Chromatography provided (after evaporation under vacuum) amorphous colorless glass foam, 0.24 g, yield 54%. MS ESI+ 451.1 (M+H)+ 100%, 473.2 (M+Na)+ 30%, ESI– 449.2 (M–H)–. $^1$H (500 MHz; CDCl$_3$): 1.30 (d, J=7.03 Hz, 6H, —CH(C$\underline{H}_3$)$_2$); 3.22-3.30 (m, 3H, —C$\underline{H}$(CH$_3$)$_2$, —CH$_2$—); 3.57 (dd, 1H, J=11.62 Hz, J=4.89 Hz, —C$\underline{H}_\alpha$H$_\beta$—); 3.63 (dd, 1H, J=11.62 Hz, J=4.89 Hz, —CH$_\alpha$$\underline{H}_\beta$—); 3.95 (pent., J=5.20 Hz, 1H, —CH—); 4.69 (bs, 2H, NH—C$\underline{H}_2$—); 7.21 (dd, J=7.03 Hz, J=5.20 Hz, 1H, H$_{Ar}$); 7.33 (d, J=7.95 Hz, 2H, H$_{Ar}$); 7.61 (d, J=7.03 Hz, 1H, H$_{Ar}$); 7.72 (d, J=7.34 Hz, 1H, H$_{Ar}$); 7.75 (d, J=8.25 Hz, 2H, H$_{Ar}$); 8.56 (d, J=4.58 Hz, 1H, H$_{Ar}$). $^{13}$C (125 MHz; CDCl$_3$): 21.4; 21.5; 25.9; 34.1; 44.1; 64.4; 72.5; 121.1; 122.3; 127.2; 128.3; 137.3; 138.3; 138.6; 149.2; 157.0; 163.4. Anal. ($C_{23}H_{26}N_6O_2S$) C, H, N.

5-[2-(Dimethylamino)-1-ethyl]thio-3-isopropyl-7-[4-(2-pyridyl)benzyl]amino-1(2)H-pyrazolo[4,3-d]pyrimidine (4.19

To a solution of 3-isopropyl-7-[4-(2-pyridyl)benzyl]amino-1(2)H-pyrazolo[4,3-d]pyrimidin-5-thiol 3.1. (0.38 g, 1 mmol) in DMSO (10 mL), $K_2CO_3$ (0.6 g) and 2-chloro-N,N-dimethylethyl-amine hydrochloride (166 mg, 1.15 mmol) was added and the mixture was stirred at 60° C. for 24 h. The reaction mixture was evaporated at temperature below 50° C. and the residue was partitioned between $CHCl_3$ and $H_2O$. The product was purified by column chromatography, stepwise 5%, 8% and 10% MeOH in $CHCl_3$. Chromatography provided (after evaporation under vacuum) amorphous colorless glass foam, 0.30 g, yield 67%. MS ESI+ 224.5 (M+2H)$^{2+}$ 70%, 448.1 (M+H)+ 100%, ESI– 446.1 (M–H)–. $^1$H (500 MHz; CDCl$_3$): 1.31 (d, J=7.03 Hz, 6H, —CH—(CH$_3$)$_2$); 2.23 (s, 6H, 2×—CH$_3$); 2.65 (t, J=7.64 Hz, 2H, —CH$_2$—); 3.20 (t, J=7.34 Hz, 2H, —CH$_2$—); 3.27 (kvint.; J=7.03 Hz, 1H, —CH—(CH$_3$)$_2$); 4.61 (bs, 2H, —NH—CH$_2$—); 6.97 (bs, 1H, —NH—CH—); 7.14-7.18 (m, 3H, ArH); 7.55 (d, J=8.25 Hz, 1H, ArH); 7.66 (dd, J=7.64 Hz, J=1.83 Hz, 1H, ArH); 7.69 (d, J=7.95 Hz, 2H, ArH); 8.55 (d, J=3.97 Hz, 1H, ArH). $^{13}$C (125 MHz; CDCl$_3$): 21.8; 26.4; 28.1; 44.0; 45.1; 59.1; 120.9; 122.3; 127.1; 128.0; 137.2; 138.2; 139.1; 149.4; 150.7; 157.0; 161.7. Anal. ($C_{24}H_{29}N_7S$) C, H, N.

5[3-(Dimethylamino)-1-propyl]thio-3-isopropyl-7-[4-(2-pyridyl)benzyl]amino-1(2)H-pyrazolo[4,3-d]pyrimidine (4.20

To a solution of 3-isopropyl-7-[4-(2-pyridyl)benzyl]amino-1(2)H-pyrazolo[4,3-d]pyrimidine-5-thiol 3.1. (0.38 g, 1 mmol) in DMSO (10 mL), $K_2CO_3$ (0.6 g) and 3-chloro-N,N-dimethylpropyl-amine hydrochloride (182 mg, 1.15 mmol) were added and the mixture was stirred at 60° C. for 24 h. The reaction mixture was evaporated at temperature below 50° C. and the residue was partitioned between $CHCl_3$ and $H_2O$. The product was purified by column chromatography, stepwise 5%, 8% and 10% MeOH in $CHCl_3$. Chromatography provided (after evaporation under vacuum) amorphous colorless glass foam, 0.33 g, yield 72%. MS ESI+ 231.6 (M+2H)$^{2+}$ 50%, 462.1 (M+H)+ 100%, ESI– 460.1 (M–H)–. $^1$H (500 MHz; CDCl$_3$): 1.32 (d, J=6.72 Hz, 6H, —CH(C$\underline{H}_3$)$_2$); 1.90 (pent., J=7.03 Hz, 2H, —CH$_2$—CH$_2$—CH$_2$—); 2.20 (s, 6H, —N(CH$_3$)$_2$); 2.43 (t, J=7.34 Hz, 2H, —CH$_2$—); 3.07 (t, J=7.03 Hz, 2H, —CH$_2$—); 3.28 (sept., J=6.72 Hz, 1H, —C$\underline{H}$(CH$_3$)$_2$); 4.66 (bs, 2H, NH—C$\underline{H}_2$—); 6.86 (bs, 1H, —NH—); 7.16-7.19 (m, 1H, H$_{Ar}$); 7.25 (d, J=7.64 Hz, 2H, H$_{Ar}$); 7.59 (d, J=7.95 Hz, 1H, H$_{Ar}$); 7.67-7.70 (m, 1H, H$_{Ar}$); 7.75 (d, J=7.64 Hz, 2H, H$_{Ar}$); 8.59 (d, J=3.97 Hz, 1H, H$_{Ar}$). $^{13}$C (125 MHz; CDCl$_3$): 21.7; 26.2; 27.4; 28.9; 29.6; 43.9; 45.1; 58.5; 120.8; 122.2; 127.0; 127.9; 137.0; 138.0; 139.0; 149.3; 150.6; 156.9; 162.0. Anal. ($C_{25}H_{31}N_7S$) C, H, N.

5-(1-Hydroxy-3-methyl-2-butyl)thio-3-isopropyl-7-[4-(2-pyridyl)benzyl]amino-1(2)H-pyrazolo[4,3-d]pyrimidine (4.21

Precursor 2-bromo-3-methyl-1-butanol was prepared from 3-methylbutenol which was brominated with bromine-dioxane complex (1:1) according to lit. (J. Label. Comp.

Radiopharm. 2007, 50, 225). The obtained 2-bromo-3-methylbutanal was than reduced to desired 2-bromo-3-methyl-1-butanol in a usual manner using NaBH$_4$ and was used for alkylation without purification.

To a solution of 3-isopropyl-7-[4-(2-pyridyl)benzyl]amino-1(2)H-pyrazolo[4,3-d]pyrimidine-5-thiol 3.1. (0.38 g, 1 mmol) in DMF (10 mL), K$_2$CO$_3$ (0.6 g) and 2-bromo-3-methyl-1-butanol (0.25 g, 1.5 mmol) was added. The reaction mixture was stirred at room temperature for 24 h and then was evaporated at temperature below 50° C. The residue was partitioned between CHCl$_3$ and H$_2$O and the product was purified by column chromatography, stepwise 2%, 3% and 4% MeOH in CHCl$_3$. Chromatography provided (after evaporation under vacuum) amorphous colorless glass foam, 0.31 g, yield 67%. MS ESI+ 463.1 (M+H)$^+$, ESI− 461.1 (M−H)$^−$. $^1$H (500 MHz; CDCl$_3$): 0.90 (d, J=6.72 Hz, 3H, —CH$_3$); 0.96 (d, J=6.72 Hz, 3H, —CH$_3$); 1.21 (d, J=6.72 Hz, 3H, —CH$_3$); 1.23 (d, J=7.03 Hz, 3H, —CH$_3$); 1.82 (sex., J=6.72 Hz, 1H, —CH—CH—(CH$_3$)$_2$); 3.13-3.26 (m, 3H, —CH(CH$_3$)$_2$, —CH$_2$—); 3.66-3.69 (m, 1H, —CH—); 4.67 (bs, 2H, NH—CH$_2$—); 7.03 (bs, 1H, —NH—CH$_2$—); 7.13-7.21 (m, 3H, H$_{Ar}$); 7.60 (d, J=7.95 Hz, 1H, H$_{Ar}$); 7.69 (dd, J=7.64 Hz, J=1.83 Hz, 1H, H$_{Ar}$); 7.72 (d, J=7.95 Hz, 2H, H$_{Ar}$); 8.58 (d, J=4.89 Hz, 1H, H$_{Ar}$), 11.9 (bs, 1H, —NH—). $^{13}$C (125 MHz; CDCl$_3$): 18.0; 18.3; 21.4; 21.6; 26.1; 33.5; 35.7; 44.1; 78.4; 120.9; 122.2; 127.1; 128.0; 137.0; 138.3; 138.6; 149.3; 157.0; 163.7. Anal. (C$_{25}$H$_{30}$N$_6$S) C, H, N.

5-β-D-Thioglucosid-3-isopropyl-7-[4-(2-pyridyl)benzyl]amino-1(2)H-pyrazolo[4,3-d]pyrimidine (4.22

To a suspension of 3-isopropyl-7-[4-(2-pyridyl)benzyl]amino-1(2)H-pyrazolo[4,3-d]pyrimidine-5-thiol 3.1. (0.38 g, 1 mmol) in MeOH (20 mL), CH$_3$ONa (60 mg, 1.1 mmol)) and 1-bromo-α-D-glucose tetraacetate (0.42 g, 1.0 mmol) were added. The reaction mixture was stirred at room temperature for 9 days and then the water (1 mL) was added and stirred for 1 h. The crude product crystallized after concentration of the reaction mixture in vacuo. The product was purified by column chromatography, stepwise 8%, 10% and 13% MeOH in CHCl$_3$. Chromatography provided crystallized product (from MeOH), 0.48 g, yield 88%, m.p. 225-227° C., α$_D$=−29.6°, (c=1.37 g/100 mL DMSO, 22° C.). MS ESI+ 561.2 (M+Na)$^+$, ESI− 537.2 (M−H)$^−$. $^1$H (500 MHz; DMSO-d$_6$): 1.35-1.39 (m, 6H, —CH(CH$_3$)$_2$); 3.15-3.26 (m, 5H, —CH(CH$_3$)$_2$, 4×—CH—); 3.42-3.46 (m, 1H, —CH—CH$_α$H$_β$—OH); 3.54-3.57 (m, 1H, —CH—CH$_α$H$_β$—OH); 4.35-4.39 (m, 1H, —OH); 4.72-4.80 (m, 2H, NH—CH$_2$—); 4.88-4.89 (m, 1H, —OH); 5.01-5.03 (m, 1H, —OH); 5.21-5.24 (m, 1H, —OH); 5.39-5.43 (m, 1H, —CH—); 7.31-7.33 (m, 1H, H$_{Ar}$); 7.44-7.51 (m, 2H, H$_{Ar}$); 7.83-7.93 (m, 2H, H$_{Ar}$); 8.00-8.08 (m, 3H, H$_{Ar}$+NH—CH$_2$— form I); 8.64-8.65 (m, 1H, H$_{Ar}$); 8.70 (bs, 1H, NH—CH$_2$— form II); 12.17 (bs, 1H, —NH—, form I); 13.75 (bs, —NH—, form II). $^{13}$C (125 MHz; DMSO-d$_6$): mixture of two forms 21.4; 21.6; 21.7; 25.0; 26.4; 42.5; 43.1; 60.4; 69.5; 71.8; 78.7; 81.1; 81.2; 85.0; 120.0; 120.1; 120.5; 122.3; 122.4; 126.3; 126.6; 127.6; 128.0; 130.6; 135.2; 137.1; 137.2; 137.7; 138.8; 139.5; 140.0; 140.5; 148.6; 148.9; 149.4; 153.9; 155.7; 155.8; 159.5; 159.6. Anal. (C$_{26}$H$_{30}$N$_6$O$_5$S) C, H, N.

5-(R/S)-(3-Amino-2-hydroxy-1-propyl)thio-3-isopropyl-7-[4-(2-pyridyl)benzyl]amino-1(2)H-pyrazolo[4,3-d]pyrimidine (4) and mixture (R/S) (4.23

To a solution of 3-isopropyl-7-[4-(2-pyridyl)benzyl]amino-1(2)H-pyrazolo[4,3-d]pyrimidine-5-thiol 3.1. (0.38 g, 1 mmol) in MeOH (10 mL), K$_2$CO$_3$ (0.17 g) and 3-benzylidenamino-1-chloropropan-2-ol (0.55 g, 3 mmol; R or R/S prepared from R or R/S—epichlorhydrine according to lit.: Org. Proc. Res. Develop., 2003, 539) were added and the mixture was stirred at 40° C. for 24 h. Reaction mixture was acidified by adding of conc. aq. HCl and stirred at 45° C. for 5 h. The crude product was concentrated at vacuum and alkalized by 1 g Na$_2$CO$_3$ in 10 ml water and crystallized from water solution at fridge. The product was then purified by column chromatography, stepwise 5%, 8% and 10% MeOH in CHCl$_3$ with trace of aq. NH$_4$OH. Crystallization from MeOH afforded 0.30 g, yield 67%, m.p. 120-125° C., (R)-antipode/124-128° C., (R/S)-antipode. MS ESI+ 450.1 (M+H)$^+$ 100%, 472.1 (M+Na)+20%, ESI− 448.1 (M−H)$^−$, 484.1 (M+Cl)$^−$ 40%, α$_D$=−4.8°, (c=1.37 g/100 mL, DMSO, 22° C.). $^1$H (500 MHz; DMSO-d$_6$): 1.38 (d, J=7.03 Hz, 6H, —CH(CH$_3$)$_2$); 2.67 (dd, J=13.14 Hz, J=7.64 Hz, 1H, NH$_2$—CH$_α$H$_β$—CH); 2.81 (dd, J=13.14 Hz, J=3.67 Hz, 1H, NH$_2$—CH$_α$H$_β$—CH); 3.21 (dd, J=14.37 Hz, J=6.42 Hz, 1H, —S—CH$_α$H$_β$—CH); 3.29 (dd, J=14.37 Hz, J=5.50 Hz, 1H, —S—CH$_α$H$_β$—CH); 3.36 (sept., J=7.03 Hz, 1H, —CH(CH$_3$)$_2$); 3.85-3.90 (m, 1H, —CH$_2$—CH—CH$_2$—); 4.82 (bs, 2H, NH—CH$_2$—); 7.28- 7.31 (qd, J=7.34 Hz, J=5.04 Hz, J=0.92 Hz, 1H, H$_{Ar}$); 7.48 (d, J=8.25 Hz, 2H, H$_{Ar}$); 7.76 (d, J=8.25 Hz, 1H, H$_{Ar}$); 7.82 (td, J=7.49 Hz, J=1.83 Hz, 1H, H$_{Ar}$); 7.86 (d, J=8.25 Hz, 2H, H$_{Ar}$); 8.55 (d, J=4.58 Hz, 1H, H$_{Ar}$). $^{13}$C (125 MHz; DMSO-d$_6$): 22.2; 27.0; 36.1; 44.8; 46.7; 72.7; 122.5; 123.7; 128.3; 128.4; 129.1; 138.9; 139.1; 139.4; 141.0; 150.2; 158.5; 163.9. Anal. (C$_{23}$H$_{27}$N$_7$OS) C, H, N.

5[(3-(4-Morpholinyl)-2-hydroxy-1-propyl]thio-3-isopropyl-7-[4-(2-pyridyl)benzyl]amino-1(2)H-pyrazolo[4,3-d]pyrimidin (4.24

To a solution of 3-isopropyl-7-[4-(2-pyridyl)benzyl]amino-1(2)H-pyrazolo[4,3-d]pyrimidine-5-thiol 3.1. (0.38 g, 1 mmol) in MeOH (10 mL), K$_2$CO$_3$ (0.17 g) and 1-chloro-3-morpholinopropan-2-ol (0.20 g, 1.2 mmol; prepared according to lit.: Russ. J. Org. Chem. 2006, 42, 1845) were added and the mixture was stirred at 45° C. for 24 h. The crude product was precipitated by adding of water and then it was purified by column chromatography, stepwise 3%, 4% and 5% MeOH in CHCl$_3$. Chromatography provided (after evaporation under vacuum) amorphous colorless glass foam, 0.31 g, yield 60%. MS ESI+ 520.1 (M+H)$^+$ 15%, 542.1 (M+Na)$^+$ 100%, ESI− 518.1 (M−H)$^−$ 30%, 554.2 (M+Cl)$^−$ 100%. $^1$H (500 MHz; CDCl$_3$): 1.17-1.22 (m, 6H, —CH(CH$_3$)$_2$); 2.30-2.33 (m, 3H, —CH—CH$_α$H$_β$—N—+—N—(CH$_α$H$_β$)$_2$—); 2.41-2.43 (m, 2H, —N—(CH$_α$H$_β$)$_2$—); 2.52 (dd, J=12.53 Hz, J=8.56 Hz, 1H, —CH—CH$_α$H$_β$—N); 3.09-3.18 (m, 2H, —CH(CH$_3$)$_2$+S-CH$_α$H$_β$—CH—); 3.27 (d, J=12.53 Hz, 1H, S—CH$_α$H$_β$—CH—); 3.49 (bs, 4H, O—(CH$_2$)$_2$—); 4.07-4.09 (m, 1H, —CH$_2$—CH—CH$_2$—); 4.64 (bs, 2H, —NH—CH$_2$—); 7.16 (dd, J=7.18 Hz, J=5.20 Hz, 1H, H$_{Ar}$); 7.21 (d, J=7.95 Hz, 2H, H$_{Ar}$); 7.40 (bs, 1H, —NH—); 7.58 (d, J=7.95 Hz, 1H, H$_{Ar}$); 7.67 (td, J=7.79 Hz, J=1.83 Hz, 1H, H$_{Ar}$); 7.72 (d, J=7.95 Hz, 2H, H$_{Ar}$); 8.57 (d, J=4.58 Hz, 1H, H$_{Ar}$). $^{13}$C (125 MHz; CDCl$_3$): 21.5; 21.6; 26.1; 36.3; 44.2; 53.8; 63.8; 66.5; 68.5; 120.7; 122.2; 127.0; 128.1; 137.0; 138.3; 138.5; 149.4; 156.8; 162.9. Anal. (C$_{27}$H$_{33}$N$_7$O$_2$S) C, H, N.

5-[3-(1-Piperazinyl)-2-hydroxy-1-propyl]thio-3-isopropyl-7-[4-(2-pyridyl)benzyl]amino-1(2)H-pyrazolo[4,3-d]pyrimidine (4.25

3-(4-Boc-piperazin-1-yl)-1,2-epoxypropane was prepared by equimolar reaction of epichlorohydrine with N-Bocpiperazine in acetonitrile in the presence of $K_2CO_3$ (2 mmol); reaction mixture was stirred at 10° C. for 2 days. The crude product was isolated after filtration by evaporation at vacuum at 45° C. The mixture of 3-isopropyl-7-[4-(2-pyridyl)benzyl]amino-1(2)H-pyrazolo[4,3-d]pyrimidine-5-thiol 3.1. (380 mg, 1 mmol), tetramethylammonium hydroxide (0.2 mL 25% solution in MeOH), triethylamine (0.2 mL, 2.2 mmol) and 3-(4-Boc-piperazin-1-yl)-1,2-epoxypropane (0.45 g, 1.8 mmol) in MeOH (5 mL) was stirred at room temperature for 2 days. The crude Boc-product was isolated by precipitation after adding water. The precipitate was dissolved in 3 mL TFA and was left 2 hours at room temperature. The solution was evaporated at vacuum and product was purified by column chromatography, stepwise 5%, 8% and 10% MeOH in $CHCl_3$ with trace of aq. $NH_4OH$. Chromatography provided (after evaporation under vacuum) amorphous colorless glass foam, 0.25 g, yield 48%. ESI+ 519.1 $(M+H)^+$, ESI− 517.1 $(M−H)^−$. $^1H$ (500 MHz; DMSO-$d_6$): 1.35 (d, J=7.03 Hz, 6H, —CH—C$\underline{H}_3$); 1.36 (d, J=7.03 Hz, 6H, —CH—C$\underline{H}_3$); 2.31-2.40 (m, 6H, N—C$\underline{H}_2$—CH—OH+2×—C$\underline{H}_2$—); 2.76-2.77 (m, 4H, 2×—C$\underline{H}_2$—); 3.00 (dd, J=13.45 Hz, J=7.03 Hz, 1H, —S—C$\underline{H}_\alpha H_\beta$—); 3.25 (sept., J=7.03 Hz, 1H, —C$\underline{H}(CH_3)_2$); 3.34 (dd, J=13.60 Hz, J=4.58 Hz, 1H, —S—CH$_\alpha\underline{H}_\beta$—); 3.88 (m, 1H, —CH$_2$—C$\underline{H}$—OH); 4.76 (bs, 2H, —N$\underline{H}$—CH$_2$—); 7.32 (qd, J=7.41 Hz, J=4.89 Hz, J=1.22 Hz, 1H, $H_{Ar}$); 7.48 (d, J=8.25 Hz, 2H, $H_{Ar}$); 7.80 (td, J=7.95 Hz, J=1.83 Hz, 1H, $H_{Ar}$); 7.92 (d, J=8.25 Hz, 1H, $H_{Ar}$); 8.05 (d, J=8.25 Hz, 2H, $H_{Ar}$); 8.32 (bs, 1H, —N$\underline{H}$—CH$_2$—); 8.64 (qd, J=4.86 Hz, J=1.83 Hz, J=0.92 Hz, 1H, $H_{Ar}$); 12.77 (bs, 1H, —NH—). $^{13}C$ (125 MHz; DMSO-$d_6$): 21.6; 21.7; 25.7; 36.0; 42.9; 44.6; 53.1; 63.8; 67.2; 120.0; 122.4; 126.5; 127.8; 137.4; 138.2; 139.8; 149.4; 150.2; 155.7; 157.9; 161.2. Anal. ($C_{27}H_{34}N_8OS$) C, H, N.

5-[2-(1-Imidazolyl)-1-ethyl]thio-3-isopropyl-7-[4-(2-pyridyl)benzyl]amino-1(2)H-pyrazolo[4,3-d]pyrimidine (4.26

N-(2-Chloroethyl)imidazole was prepared by stirring 20 g sodium imidazolide in 1,2-dichloroethane (80 mL) at room temperature for 3 days. After adding water, the final product was extracted in 1,2-dichloroethane phase and then obtained by evaporation of organic phase in vacuum. To a solution of 3-isopropyl-7-[4-(2-pyridyl)benzyl]amino-1(2)H-pyrazolo[4,3-d]pyrimidine-5-thiol 3.1. (0.38 mg, 1 mmol) in DMF (8 mL) $K_2CO_3$ (0.2 g) and N-(2-chlorethyl)imidazole (143 mg, 1.1 mmol) were added. The reaction mixture was stirred at room temperature for 24 h. The crude product was precipitated by adding water and was purified by column chromatography, stepwise 3%, 4% and 5% MeOH in $CHCl_3$. Crystallization from $CHCl_3$ provided colorless product, 0.21 g, yield 45%, m.p. 208-211° C., MS ESI+ 471.1 $(M+H)^+$, ESI− 469.1 $(M−H)^−$. NMR: mixture of tautomers, $^1H$ (500 MHz, DMSO-$d_6$): δ 1.38 (d, J=6.7 Hz, 6H, —CH(C$\underline{H}_3)_2$), 3.28-3.40 (m, 3H, —C$\underline{H}(CH_3)_2$+—C$\underline{H}_2$—CH$_2$—), 4.25 (bs, 2H, —CH$_2$—C$\underline{H}_2$—), 4.73-4.76 (m, 2H, NH—C$\underline{H}_2$—), 6.87 (s, 1H, $H_{Ar}$), 7.15-7.57 (m, 5H, $H_{Ar}$), 8.12-7.83 (m, 5H, $H_{Ar}$+—NH—), 8.63 (s, 1H, $H_{Ar}$), 12.25 (s, 1H, —NH—). $^{13}C$ (125 MHz, DMSO-$d_6$): δ 21.70, 26.39, 31.16, 42.6, 43.23, 45.74, 119.18, 120.12, 122.55, 126.47, 126.69, 127.55, 128.02, 128.42, 137.19, 137.73, 139.45, 148.87, 149.51, 155.71, 159.76. Anal. ($C_2H_{28}N_8S$) C, H, N.

5-(3-Amino-1-propyl)thio-3-isopropyl-7-[4-(2-pyridyl)benzyl]amino-1(2)H-pyrazolo[4,3-d]pyrimidine (4.27

To a solution of 3-isopropyl-7-[4-(2-pyridyl)benzyl]amino-1(2)H-pyrazolo[4,3-d]pyrimidine-5-thiol 3.1. (0.38 mg, 1 mmol) in DMF (10 mL), $K_2CO_3$ (0.35 g) and 3-bromopropylamine hydrochloride (0.40 g, 1.8 mmol) were added. The reaction mixture was stirred at 45° C. for 24 h. DMF was evaporated in vacuo and the product was purified by column chromatography, stepwise 5%, and 10% MeOH in $CHCl_3$ with trace of aq. $NH_4OH$. Chromatography provided (after evaporation under vacuum) amorphous colorless glass foam, 0.30 g, yield 69%. ESI+ 434.1 $(M+H)^+$, ESI− 432.1 $(M−H)^−$. $^1H$ (500 MHz; DMSO-$d_6$): 1.32 (d, J=7.03 Hz, 6H, —CH—$(CH_3)_2$); 1.75 (pent., J=7.03 Hz, 2H, —CH$_2$—C$\underline{H}_2$—CH$_2$—); 2.66 (t, J=7.03 Hz, 2H, —CH$_2$—); 3.05 (t, J=7.03 Hz, 2H, —CH$_2$—); 3.22 (sept., J=7.03 Hz, 1H, —CH—$(CH_3)_2$); 4.72 (bs, 2H, —NH—CH$_2$—); 7.27-7.29 (m, 1H, ArH); 7.44 (d, J=8.56 Hz, 2H, ArH); 7.79-7.83 (m, 1H, ArH); 7.87-7.89 (m, 1H, ArH); 8.01 (d, J=8.25 Hz, 2H, ArH); 8.42 (appt. bt, 1H, —NH—); 8.59-8.61 (m, 1H, ArH). $^{13}C$ (125 MHz; DMSO-$d_6$): 22.2, 26.4, 28.0, 31.8, 40.3, 43.5, 120.6, 123.0, 123.9, 127.1, 128.3, 137.7, 138.0, 139.1, 140.5, 146.3, 150.0, 150.7, 156.3, 161.2. Anal. ($C_{23}H_{27}N_7S$) C, H, N.

5-[(Oxazolidin-2-on-5-yl)methyl]thio-3-isopropyl-7-[4-(2-pyridyl)benzyl]amino-1(2)H-pyrazolo[4,3-d]pyrimidine (4.28

To a solution of 3-isopropyl-7-[4-(2-pyridyl)benzyl]amino-1(2)H-pyrazolo[4,3-d]pyrimidine-5-thiol 3.1. (0.38 mg, 1 mmol) in DMF (5 mL) $K_2CO_3$ (0.15 g) and 5-chloromethyl-2-oxazolidinone (0.15 g, 1.1 mmol) were added. The reaction mixture was stirred at 45° C. for 24 h. The crude product was precipitated by adding water and was purified by column chromatography, stepwise 4%, 5% and 6% MeOH in $CHCl_3$. Chromatography provided (after evaporation under vacuum) amorphous colorless glass foam, 0.35 g, yield 74%. ESI+ 476.2 $(M+H)^+$, ESI− 474.2 $(M−H)^−$. $^1H$ (500 MHz; $CD_3OD$): 1.38 (d, J=7.03 Hz, 6H, —CH(C$\underline{H}_3)_2$); 3.26 (dd, J=14.21 Hz, J=7.34 Hz, 1H, —NH—C$\underline{H}_\alpha H_\beta$—CH—); 3.33-3.37 (m, 2H, —C$\underline{H}(CH_3)_2$+—S—C$\underline{H}_\alpha H_\beta$—CH—); 3.52 (bt, J=8.80 Hz, 1H, —S—CH$_\alpha$$\underline{H}_\beta$—CH—); 3.63 (dd, J=14.06 Hz, J=4.89 Hz, 1H, —NH—CH$_\alpha\underline{H}_\beta$—CH—); 4.82 (bs, 2H, NH—C$\underline{H}_2$—); 4.84-4.86 (m, 1H, —CH$_2$—C$\underline{H}$—CH$_2$—); 7.30 (qd, J=7.47 Hz, J=4.89 Hz, J=1.22 Hz, 1H, $H_{Ar}$); 7.47 (d, J=8.25 Hz, 2H, $H_{Ar}$); 7.77 (d, J=7.79 Hz, 1H, $H_{Ar}$); 7.82 (td, J=7.34 Hz, J=1.83 Hz, 1H, $H_{Ar}$); 8.25 (d, J=8.25 Hz, 2H, $H_{Ar}$); 8.55 (d, J=4.89, 1H, $H_{Ar}$). $^{13}C$ (125 MHz; $CD_3OD$): 22.2; 27.1; 35.1; 44.8; 45.7; 77.0; 122.5; 123.6; 128.3; 128.8; 138.8; 139.4; 141.1; 150.2; 158.5; 162.0; 162.4. Anal. ($C_{25}H_{27}N_7O_2S$) C, H, N.

5-(2,3-Diamino-1-propyl)thio-3-isopropyl-7-[4-(2-pyridyl)benzyl]amino-1(2)H-pyrazolo[4,3-d]pyrimidine (4.29

To a solution of 3-isopropyl-7-[4-(2-pyridyl)benzyl]amino-1(2)H-pyrazolo[4,3-d]pyrimidine-5-thiol 3.1. (0.38 mg, 1 mmol) in DMF (5 mL), $K_2CO_3$ (0.15 g) and 2,3-di(benzyloxycarbonylamino)-1-chloropropane (0.41 g, 1.1 mmol; prepared according to lit.: J. Org. Chem. 1975, 40, 1653) were added. The crude di-Z-protected product was isolated as a precipitate after adding water and then was triturated with 33% HBr in AcOH (1 mL) at room temperature for 1 h. After evaporation in vacuo the product was purified by column chromatography, stepwise 10%, 12% and 15% MeOH in $CHCl_3$ with trace of aq. $NH_4OH$. Chromatography provided (after evaporation under vacuum) amorphous colorless glass foam, 0.31 g, yield 69%. MS ESI+ 449.1 $(M+H)^+$, ESI− 447.1 $(M−H)^−$. $^1H$ (500 MHz;

CDCl$_3$): 1.29 (d, J=6.72 Hz, 6H, —CH(C$\underline{H}_3$)$_2$); 2.50 (dd, J=12.69 Hz, J=7.03 Hz; 1H, NH$_2$—C$\underline{H}_\alpha$H$_\beta$—CH—); 2.73 (dd, J=12.69 Hz, J=3.67 Hz; 1H, NH$_2$—CH$_\alpha\underline{H}_\beta$—CH—); 2.92-3.00 (m, 2H, —S—C$\underline{H}_\alpha$H$_\beta$—CH—+—S—CH$_2$—C$\underline{H}$—CH$_2$—); 3.20-3.27 (m, 2H, —C$\underline{H}$(CH$_3$)$_2$+—S—C$\underline{H}_\alpha$H$_\beta$—CH—); 3.79 (bs, 4H, 2×—NH$_2$); 4.60 (bs, 2H, —NH—C$\underline{H}_2$—); 7.15 (qd, J=7.34 Hz, J=4.89 Hz, J=0.92 Hz, 1H, H$_{Ar}$); 7.21 (d, J=8.25 Hz, 2H, H$_{Ar}$); 7.25 (bs, 1H, —N$\underline{H}$—CH$_2$—); 7.56 (d, J=7.95 Hz, 1H, H$_{Ar}$); 7.66 (td, J=7.95 Hz, J=1.83 Hz, 1H, H$_{Ar}$); 7.74 (d, J=8.25 Hz, 2H, H$_{Ar}$); 8.57 (d, J=4.89 Hz, 1H, H$_{Ar}$). $^{13}$C (125 MHz; CDCl$_3$): 21.7; 21.8; 26.2; 36.6; 43.9; 46.6; 53.2; 120.7; 122.2; 124.8, 127.1; 127.8; 137.0; 138.2; 138.9; 139.0; 146.6; 149.4; 150.8; 156.8; 161.4. Anal. (C$_{23}$H$_{28}$N$_8$S) C, H, N.

5-(2-Methylthio-1-ethyl)thio-3-isopropyl-7-[4-(2-pyridyl)benzyl]amino-1(2)H-pyrazolo[4,3-d]pyrimidine (4.30

To a solution of 3-isopropyl-7-[4-(2-pyridyl)benzyl] amino-1(2)H-pyrazolo[4,3-d]pyrimidin-5-thiol 3.1. (0.38 g, 1.0 mmol) in DMF (6 mL), K$_2$CO$_3$ (0.2 g) and 2-chloroethyl methyl sulfide (101 L, 1 mmol) were added and the mixture was stirred at room temperature for 16 h. The reaction mixture was evaporated at temperature below 50° C. and the residue was partitioned between CHCl$_3$ and H$_2$O. The combined organic phase was dried with sodium sulfate and evaporated under vacuum. The product was purified by column chromatography, stepwise 2%, 3% and 4% MeOH in CHCl$_3$ and the product was crystallized from abs. Et$_2$O, 0.35 g, yield 74%, m.p. 140-141° C. APCI+474.3 (M+H)$^+$, ESI− 472.2 (M−H)$^-$. $^1$H (500 MHz; CDCl$_3$): 1.32 (d, J=7.03 Hz, 6H, —CH(C$\underline{H}_3$)$_2$); 2.11 (s, 3H, —S—C$\underline{H}_3$); 2.79-2.82 (m, 2H, H$_3$C—S—C$\underline{H}_2$—); 3.25-3.28 (m, 3H, —S—C$\underline{H}_2$—+—C$\underline{H}$(CH$_3$)$_2$); 4.61 (bs, 2H, —NH—C$\underline{H}_2$—); 6.65 (bs, 1H, —N$\underline{H}$—CH$_2$—); 7.13-7.19 (m, 3H, H$_{Ar}$); 7.59 (d, J=8.25 Hz, 1H, H$_{Ar}$); 7.69-7.73 (m, 3H, H$_{Ar}$); 7.58 (d, J=4.89 Hz, 1H, H$_{Ar}$); 12.09 (bs, 1H, —NH—). $^{13}$C (125 MHz; CDCl$_3$): 15.2; 21.6; 26.2; 30.6; 34.0; 44.0; 121.0; 122.3; 127.0; 127.9; 137.2; 138.1; 138.7; 149.3; 156.9; 161.7. Anal. (C$_{23}$H$_{26}$N$_6$S$_2$) C, H, N.

5-(2-Aminocyclohexyl)thio-3-isopropyl-7-[4-(2-pyridyl)benzyl]amino-1(2)H-pyrazolo[4,3-d]pyrimidine (4.31

To a stirred mixture of 3-isopropyl-7-[4-(2-pyridyl)benzyl]amino-1(2)H-pyrazolo[4,3-d]pyrimidine-5-thiol 3.1. (0.38 g, 1.0 mmol) and DMF (10 mL) in 1 mL of aq. 48% solution HBr, 1,2-cyclohexenimine (0.60 mL, 5 mmol; prepared according to lit.: Org. Synth., 87, 2010, 161-169) was dropwise added. The mixture was stirred at room temperature for 24 h. The reaction mixture was neutralized by aq. solution of Na$_2$CO$_3$ and the crude product was isolated as a precipitate. The product was purified by column chromatography, stepwise 5%, 8% and 11% MeOH in CHCl$_3$ with trace of aq.

NH$_4$OH. Chromatography provided product crystallized from CHCl$_3$, 0.06 g, yield 13%, m.p. 165-185° C. MS APCI+474.4 (M+H)$^+$, APCI—442.2 (M−H)$^-$. $^1$H (500 MHz; DMSO-d$_6$): 1.07-1.30 (m, 3H, H-cyclohexyl); 1.36 (d, J=7.03 Hz, 6H, —CH(C$\underline{H}_3$)$_2$); 1.40-1.47 (m, 1H, H-cyclohexyl); 1.57-1.65 (m, 1H, H-cyclohexyl); 1.88-1.91 (m, 1H, H-cyclohexyl); 2.19-2.22 (m, 1H, H-cyclohexyl); 2.61-2.65 (m, 1H, H-cyclohexyl); 3.22-3.26 (m, 3H, —C$\underline{H}$(CH$_3$)$_2$, —CH$_2$—); 3.35-3.47 (m, 1H, H-cyclohexyl); 4.72-4.81 (m, 2H, NH—C$\underline{H}_2$—); 7.32 (qd, J=7.34 Hz, J=4.86 Hz, J=1.22, 1H, H$_{Ar}$); 7.47 (d, J=8.25 Hz, 2H, H$_{Ar}$); 7.85 (td, J=7.34 Hz, J=1.83 Hz, 1H, H$_{Ar}$); 7.91 (d, J=7.95 Hz, 1H, H$_{Ar}$); 8.05 (d, J=8.25 Hz, 2H, H$_{Ar}$); 8.27 (bs, 1H, —NH—); 8.64 (d, J=4.89 Hz, 1H, H$_{Ar}$). $^{13}$C (125 MHz; DMSO-d$_6$): 21.5; 21.6; 24.2; 25.7; 30.5; 32.8; 34.9; 42.9; 52.2; 52.6; 79.0; 120.0; 122.4; 126.4; 127.7; 137.1; 137.4; 139.8; 149.4; 155.7; 160.8. Anal. (C$_{25}$H$_{29}$N$_7$S) C, H, N.

5-(3,3,3-Trifluoro-2-hydroxy-1-propyl)thio-3-isopropyl-7-[4-(2-pyridyl)benzyl]amino-1(2)H-pyrazolo[4,3-d]pyrimidine (4.32

2-Bromo-1,1,1-trifluoro-2-propanol (0.11 mL, 1.05 mmol) was dropwise added to a mixture of 3-isopropyl-7-[4-(2-pyridyl)benzyl]amino-1(2)H-pyrazolo[4,3-d]pyrimidine-5-thiol 3.1. (0.38 mg, 1.0 mmol) in DMF (6 mL) and K$_2$CO$_3$ (0.12 g). The reaction mixture was stirred at room temperature for 4 h. The reaction mixture was evaporated at temperature below 50° C. and the residue was partitioned between CHCl$_3$ and H$_2$O. The product was purified by column chromatography, stepwise 2%, 3% and 4% MeOH in CHCl$_3$. Chromatography provided a product which was crystallized from DCM, 0.15 g, yield 31%, m.p. 174-177° C. MS ESI+ 489.1 (M+H)$^+$, ESI− 487.1 (M−H)$^-$. NMR: Two tautomers: 2:1 (integration showed in relative values)$^1$H (500 MHz; DMSO-d$_6$): 1.34 (d, J=7.03 Hz, 6H, —CH(C$\underline{H}_3$)$_2$ form I); 1.37 (d, J=7.03 Hz, 6H, —CH(C$\underline{H}_3$)$_2$ form II); 2.84-2.91 (m, 1H, —S—C$\underline{H}_\alpha$H$_\beta$-form I and II); 3.20-3.28 (m, H, —C$\underline{H}$(CH$_3$)$_2$, form I and II); 3.61 (d, J=13.75 Hz, 1H, —S—CH$_\alpha\underline{H}_\beta$, form II); 3.67 (dd, J=13.75 Hz, J=2.14 Hz, 1H, —S—CH$_\alpha\underline{H}_\beta$, form I); 4.23 (bs, 1H, S—CH$_2$—C$\underline{H}$-form I and II); 4.72 (d, J=5.81 Hz, 2H, NH—C$\underline{H}_2$—, form II); 4.77 (d, J=5.50 Hz, 2H, NH—C$\underline{H}_2$—, form I); 6.59 (d, J=6.72 Hz, 1H, CH—O$\underline{H}$, form I and II); 7.29-7.33 (m, 1H, H$_{Ar}$, form I and II); 7.43 (d, J=7.95 Hz, 2H, H$_{Ar}$, form II); 7.49 (d, J=8.25 Hz, 2H, H$_{Ar}$, form I); 7.82-7.87 (m, 1H, H$_{Ar}$, form I and II); 7.89-7.94 (m, 1H, H$_{Ar}$, form I and II); 8.01 (d, J=7.95 Hz, 2H, H$_{Ar}$, form II); 8.09 (m, 3H, H$_{Ar}$+—N$\underline{H}$—CH$_2$—, form I); 8.62-8.65 (m, 1H, H$_{Ar}$, form I and II); 8.77 (bt, J=5.81 Hz, 1H, —N$\underline{H}$—CH$_2$—, form II); 12.21 (bs, 1H, —NH—, form I); 13.78 (bs, 1H, —NH—, form 1). $^{13}$C (125 MHz; DMSO-d$_6$): mixture of two forms 21.3; 21.4; 21.5; 24.9; 26.2; 26.4; 31.1; 42.4; 43.0; 67.8 (q, —CF$_3$, form I); 67.9 (q, —CF$_3$, form II); 119.9; 120.0 120.5; 122.3; 122.4; 124.2; 126.3; 126.5; 126.6; 127.6; 127.9; 130.5; 134.8; 137.0; 137.1; 137.7; 138.9; 139.3; 139.8; 140.3; 148.8; 149.4; 154.0; 155.6; 155.8; 160.0. Anal. (C$_{23}$H$_{23}$F$_3$N$_6$OS) C, H, N.

5-(Methoxymethyl)thio-3-isopropyl-7-[4-(2-pyridyl)benzyl]amino-1(2)H-pyrazolo[4,3-d]pyrimidine (4.33

Chloromethyl methyl ether (31 L, 0.41 mmol) and K$_2$CO$_3$ (0.10 g) was added to a mixture of 3-isopropyl-7-[4-(2-pyridyl)benzyl]amino-1(2)H-pyrazolo[4,3-d]pyrimidin-5-thiol 3.1. (0.14 mg, 0.37 mmol) in DMF (3 mL). The reaction mixture was stirred at room temperature for 4 h. The reaction mixture was evaporated at temperature below 50° C. and the residue was partitioned between CHCl$_3$ and H$_2$O. The product was purified by column chromatography, stepwise 1%, 2% and 3% MeOH in CHCl$_3$. Chromatography provided product crystallized from DCM, 0.11 g, yield 70%, m.p. 160-162° C. MS ESI+ 421.1 (M+H)$^+$, ESI− 419.1 (M−H)$^-$. $^1$H (500 MHz; DMSO-d$_6$): 1.35-1.38 (m, 6H, —CH(C$\underline{H}_3$)$_2$); 3.21-3.27 (m, 4H, —C$\underline{H}$(CH$_3$)$_2$, —CH$_3$); 4.69-4.80 (m, 2H, NH—C$\underline{H}_2$—); 5.29-5.34 (m, 2H, —S—CH₂—); 7.31-7.33 (m, 1H, H$_{Ar}$); 7.45-7.52 (m, 2H, H$_{Ar}$); 7.83-7.86 (m, 1H, H$_{Ar}$); 7.88-7.93 (m, 1H, Ha.); 8.00-8.08 (m, 2H, H$_{Ar}$); 8.63-8.64 (m, 1H, H$_{Ar}$); 12.21 (bs, —NH—, form I); 13.79 (bs, —NH—, form II). $^{13}$C (125 MHz; DMSO-d$_6$): mixture of two tautomeric forms. 21.5; 21.7; 24.8; 26.2; 42.5; 43.2; 55.9; 73.3; 120.0 120.6; 122.3; 122.4; 126.3; 126.6; 127.6; 128.0; 137.1; 137.7; 139.4; 139.8; 148.7; 148.9; 149.4; 153.9; 155.6; 155.8; 159.2. Anal. (C$_{22}$H$_{24}$N$_6$OS) C, H, N.

5-(3-Methylamino-1-ethyl)thio-3-isopropyl-7-[4-(2-pyridyl)benzyl]amino-1(2)H-pyrazolo[4,3-d]pyrimidine (4.34

2-Bromo-N-methylethylamine hydrobromide (0.66 g, 3.0 mmol; prepared according to lit.: Amanda et al., Soft Matter, 2011, 7, 5627-5637) was added to a mixture of 3-isopropyl-7-[4-(2-pyridyl)benzyl]amino-1(2)H-pyrazolo[4,3-d]pyrimidine-5-thiol 3.1. (0.38 mg, 1.0 mmol) in DMF (8 mL) and NaHCO$_3$ (0.50 g). The reaction mixture was stirred at room temperature for 2 days. The reaction mixture was evaporated at temperature below 50° C. and the residue was partitioned between CHCl$_3$ and H$_2$O. The product was purified by column chromatography, stepwise 6%, 8% and 10% MeOH in CHCl$_3$ with trace of aq. NH$_4$OH. Chromatography provided (after evaporation under vacuum) amorphous colorless glass foam 0.07 g, yield 16%. MS ESI+ 434.1 (M+H)⁺, ESI− 432.1 (M−H)⁻. $^1$H (500 MHz, CDCl$_3$): δ 1.31 (d, J=7.0 Hz, 6H, —CH(CH$_3$)$_2$); 2.43 (s, 3H, —NH—CH$_3$); 3.01 (t, J=6.0 Hz, 2H, —CH$_2$—CH$_2$—); 3.23 (m, 3H, —CH(CH$_3$)$_2$+—CH$_2$—CH$_2$—); 4.66 (s, 2H, NH—CH$_2$—); 7.19-7.16 (m, 1H, H$_{Ar}$); 7.30 (d, J=8.3 Hz, 2H, H$_{Ar}$); 7.45 (bs, 1H, —NH); 7.57 (d, J=7.9 Hz, 1H, H$_{Ar}$); 7.68 (td, J=7.7, 1.6 Hz, 1H, H$_{Ar}$); 7.75 (d, J=8.1 Hz, 2H, H$_{Ar}$); 8.59 (d, J=4.6 Hz, 1H, H$_{Ar}$). $^{13}$C (125 MHz, CDCl$_3$): δ 21.50, 21.73, 26.22, 29.47, 29.67, 34.70, 44.01, 50.73, 120.76, 122.22, 127.03, 127.82, 128.03, 137.02, 138.18, 138.67, 139.07, 149.39, 150.50, 156.97, 161.25. Anal. (C$_{23}$H$_{27}$N$_7$S) C, H, N.

5-(2-sulfanylethyl)thio-3-isopropyl-7-[4-(2-pyridyl)benzyl]amino-1(2)H-pyrazolo[4,3-d]pyrimidine (4.35

A solution of 3-isopropyl-7-[4-(2-pyridyl)benzyl]amino-1(2)H-pyrazolo [4,3-d]pyrimidine-5-thiol 3.1. (0.38 g, 1.0 mmol) and thiirane (1.02 g) and 4 drops of triethylamine in DMF (14 mL) was heated at 60° C. for 6 hours in an autoclave. The crude product was obtained as a precipitate after cooling to room temperature and diluting with DEMI water (40 mL). The product was purified by column chromatography in succession: sequentially 3%, 4% and 5% MeOH in CHCl$_3$. Evaporation of the solvents in vacuo gave 0.196 g of product as an amorphous, colorless, glassy foam, in 45% yield. MS ESI+ 436.7 (M+H)⁺, ESI− 434.7 (M−H)⁻ a 871.0 (2M−H)⁻. NMR: $^1$H (500 MHz, CDCl$_3$): 1.39 (d, J=7.0 Hz, 6H, —CH—(CH$_3$)$_2$), 2.86 (t, J=7.5 Hz, 2H, —CH$_2$—), 3.29 (t, J=7.6 Hz, 2H, —CH$_2$—), 3.34 (sept., J=7.0 Hz, 1H, —CH(CH$_3$)$_2$), 4.69 (bd, J=4.0 Hz, 2H, NH—CH$_2$—), 6.56 (bs, 1H, —NH—), 7.25-7.23 (m, 3H, H$_{Ar}$), 7.66 (d, J=7.9 Hz, 1H, H$_{Ar}$), 7.74-7.80 (m, 3H, H$_{Ar}$), 8.64 (d, J=5.5 Hz, 1H, H$_{Ar}$). $^{13}$C (125 MHz, CDCl$_3$): 21.64, 24.88, 26.26, 35.21, 44.15, 121.09, 122.45, 127.21, 127.97, 137.29, 138.30, 138.82, 149.43, 157.07, 161.53. Anal. (C$_{22}$H$_{24}$N$_6$S$_2$) C, H, N.

5-(2-Hydroxy-1-ethyl)thio-3-isopropyl-7-[4-(imidazol-1-yl)benzyl]amino-1(2)H-pyrazolo[4,3-d]pyrimidine (4.50

To a stirred mixture of 3-isopropyl-7-[4-(imidazol-1-yl)benzyl]amino-1(2H)-pyrazolo[4,3-d]pyrimidine-5-thiol 3.3 and tetramethylammonium hydroxide (catal. amount, 40 mg) in MeOH (4 mL), oxirane (80 mg, 1.8 mmol, dissolved in 2 mL of MeOH) was added and the mixture was stirred at room temperature for 16 h. The product was first isolated as a precipitate upon addition of water. The product was purified by column chromatography: sequentially 2%, 3% and 4% MeOH in CHCl$_3$ to give 0.35 g of a colorless amorphous, solid foam in 85% yield. Crystallization from DCM yielded 0.30 g, i.e. 72%, m.p. 173-175° C., UV (nm): 244 λ$_{max}$, 315 λ$_{max}$. MS ESI+ 410.1 (M+H)⁺, ESI− 408.1 (M−H)⁻. NMR: Směs dvou tautomerů (2:1). $^1$H (500 MHz, DMSO-d$_6$) δ 1.31-1.41 (m, 6H, —CH(CH$_3$)$_2$); 3.13 (m, 2H, —CH$_2$—); 3.25 (m, 1H, —CH(CH$_3$)$_2$); 3.65-3.59 (m, 2H, —CH$_2$—); 4.66-4.74 (m, 2H, —CH$_2$—NH); 4.91 (t, J=5.5 Hz, 1H, —OH); 7.07-7.09 (m, 1H, H$_{Ar}$); 7.72-7.47 (m, 5H, H$_{Ar}$); 8.04 (t, J=5.3 Hz, —NH isomer A); 8.20-8.30 (m, 1H, H$_{Ar}$); 8.75 (t, J=6.0 Hz, —NH, isomer B); 12.17 (s, —NH, isomer A); 13.78 (s, —NH isomer B), $^{13}$C-NMR (125 MHz, DMSO-d$_6$) δ 21.6, 21.8, 24.9, 26.3, 33.0, 42.2, 42.8, 54.9, 60.5, 60.6, 118.0, 120.2, 120.4, 128.8, 129.1, 129.7, 129.8, 135.5, 135.6, 135.9, 137.4, 138.4, 140.0, 148.6, 148.8, 153.7, 160.7. Anal. (C$_2$H$_{23}$N$_{67}$OS) C, H, N.

5-(2-Amino-1-ethyl)thio-3-isopropyl-7-[4-(imidazol-1-yl)benzyl]amino-1(2)H-pyrazolo[4,3-d]pyrimidin (4.57

To a stirred mixture of 3-isopropyl-7-[4-(imidazol-1-yl)benzyl]amino-1(2H)-pyrazolo[4,3-d]pyrimidine-5-thiol 3.3 (1.0 g, 2.66 mmol) and 3.1 mL of 48% HBr in DMF (20 mL) was added aziridine (0.42 mL, 8 mmol) at room temperature. The reaction mixture was stirred at room temperature for 24 h, then neutralized with aqueous saturated Na$_2$CO$_3$, and the crude product was isolated as a precipitate. The product was purified by column chromatography successively with 3%, 5%, 7% and 10% MeOH in CHCl$_3$ with a small amount of aq. NH$_4$OH. Concentration in vacuo gave 0.60 g of an amorphous, colorless solid foam product, in 55% yield. MS ESI+ 409.2 (M+H)⁺, ESI− 407.2 (M−H)⁻. NMR: $^1$H (500 MHz, DMSO-d$_6$) δ 1.35 (d, J=6.7 Hz, 6H, —CH(CH$_3$)$_2$); 2.85 (t, J=6.7 Hz, 2H, —CH$_2$—CH$_2$—); 3.10 (t, J=6.6 Hz, 2H, —CH$_2$—CH$_2$—); 3.26 (sept., J=7.0 Hz, 1H, —CH(CH$_3$)$_2$); 4.77 (bs, 2H, NH—CH$_2$—); 7.08 (s, 1H, H$_{Ar}$), 7.50 (d, J=8.3 Hz, 2H, H$_{Ar}$), 7.61 (d, J=8.3 Hz, 2H, H$_{Ar}$), 7.70 (s, 1H, H$_{Ar}$), 8.22 (s, 1H, H$_{Ar}$), 8.44 (s, 1H, —NH). $^{13}$C (125 MHz, DMSO-d$_6$) δ 21.74, 25.87, 33.07, 41.12, 42.67, 48.60, 118.03, 120.36, 128.94, 129.83, 135.49, 135.82, 137.85, 160.41. Anal. (C$_{20}$H$_{24}$N$_8$S) C, H, N.

5-(2-Hydroxy-1-ethyl)thio-3-isopropyl-7-[4-(pyrazol-1-yl)benzyl]amino-1(2)H-pyrazolo[4,3-d]pyrimidin (4.80

To a stirred mixture of 3-isopropyl-7-[4-(pyrazol-1-yl)benzyl]amino-1(2H)-pyrazolo[4,3-d]pyrimidine-5-thiol 3.2 (80 mg, 1.8 mmol, dissolved in 2 mL of MeOH), a tetramethylammonium hydroxide (catal amount, 40 mg) in MeOH (4 mL), oxirane (0.37 g, 1 mmol) was added and the mixture was stirred at room temperature for 16 h. The product was first isolated as a precipitate upon addition of water. The product was purified by column chromatography in succession: sequentially 2%, 3% and 4% MeOH in CHCl$_3$ to give 0.35 g of a colorless amorphous, solid foam in 85% yield. UV (nm): 248 λ$_{max}$, 268 sh, 313 λ$_{max}$. MS ESI+ 410.1 (M+H)⁺, ESI− 408.1 (M−H)⁻. NMR: $^1$H (500 MHz; CDCl$_3$): $^1$H (500 MHz; CDCl$_3$): 1.22 (d, J=7.03 Hz, 6H, —CH(CH$_3$)$_2$); 3.18 (sept., J=7.03 Hz, 1H, —CH(CH$_3$)$_2$);

3.22 (dd, J=4.58 Hz, J=4.74 Hz, 2H, —S—CH$_2$—); 3.96 (dd, J=4.89 Hz, J=5.04 Hz, 2H, —CH$_2$—O); 4.62 (bs, 2H, —NH—CH$_2$—); 6.39 (dd, J=2.45 Hz, J=1.83 Hz, 1H, H$_{Ar}$); 7.17 (d, J=8.56 Hz, 2H, H$_{Ar}$); 7.35 (bs, 1H, —NH—); 7.39 (d, J=8.56 Hz, 2H, H$_{Ar}$); 7.63 (d, J=1.83 Hz, 1H, H$_{Ar}$); 7.79 (d, J=2.45 Hz, 1H, H$_{Ar}$). $^{13}$C (125 MHz; CDCl$_3$): 21.5; 26.0; 34.2; 43.8; 64.4; 107.7; 119.3; 127.2; 128.7; 136.0; 139.1; 141.1; 163.4. Anal. (C$_2$H$_{23}$N$_7$OS) C, H, N.

5-(2-Hydroxy-1-propyl)thio-3-isopropyl-7-[4-(pyrazol-1-yl)benzyl]amino-1(2H)-pyrazolo[4,3-d]pyrimidin (4.81

To a mixture of 3-isopropyl-7-[4-(pyrazol-1-yl)benzyl]amino-1(2H)-pyrazolo[4,3-d]pyrimidine-5-thiol 3.2 (0.37 g, 1 mmol), and tetramethylammonium hydroxide (cat., 40 mg) in MeOH (6 mL), methyl oxirane (130 mg, 1.8 mmol, dissolved in 2 mL MeOH) was added and stirred at room temperature for 6 h. The crude product was obtained by precipitation from the reaction mixture by water and was further purified by column chromatography on silica gel successively in a 1%, 2%, 3% MeOH in CHCl3 system. The product was crystallized from DCM/Et$_2$O to yield 0.25 g of product, in 59% yield, m.p. 126-131° C. MS ESI+ 424.1 (M+H)$^+$, ESI− 422.1 (M−H)$^−$. NMR: $^1$H (500 MHz; CDCl$_3$): 1.20 (d, J=7.03 Hz, 6H, —CH(CH$_3$)$_2$); 1.26 (d, J=6.11 Hz, 3H, —CH$_3$); 3.08 (dd, J=15.13 Hz, J=7.03 Hz, 1H, —CH$_\alpha$H$_\beta$—); 3.17 (sept., J=7.03 Hz, 1H, —CH(CH$_3$)$_2$); 3.27 (dd, J=14.82 Hz, J=2.45 Hz, 1H, —CH$_\alpha$H$_\beta$—); 4.20-4.23 (m, 1H, —CH—); 4.64 (bs, 2H, —NH—CH$_2$—); 6.40 (t, J=1.83 Hz, 1H, H$_{Ar}$); 7.19 (d, J=8.56 Hz, 2H, H$_{Ar}$); 7.40 (d, J=8.56 Hz, 2H, H$_{Ar}$); 7.65 (d, J=1.83 Hz, 1H, H$_{Ar}$); 7.80 (d, J=2.45 Hz, 1H, H$_{Ar}$). $^{13}$C (125 MHz; CDCl$_3$): 21.6; 21.7; 22.8; 26.2; 39.9; 43.9; 69.2; 107.8; 119.5; 127.3; 128.9; 136.2; 139.3; 141.2; 163.7. Anal. (C$_{21}$H$_{25}$N$_7$OS) C, H, N.

5-(2-Amino-1-ethyl)thio-3-isopropyl-7-[4-(pyrazol-1-yl)benzyl]amino-1(2H)-pyrazolo[4,3-d]pyrimidin (4.87

To a stirred mixture of 3-isopropyl-7-[4-(pyrazol-1-yl)benzyl]amino-1(2H)-pyrazolo[4,3-d]pyrimidine-5-thiol 3.2 (1.0 g, 2.66 mmol) and 3.1 mL of 48% HBr in DMF (20 mL), aziridine (0.42 mL, 8 mmol) was added at room temperature. The reaction mixture was stirred at room temperature for 24 h, then neutralized with aqueous saturated Na$_2$CO$_3$, and the crude product was isolated as a precipitate. The product was purified by column chromatography successively with 3%, 5%, 7% and 10% MeOH in CHCl$_3$ with a small amount of aq. NH$_4$OH. Concentration in vacuo gave 0.69 g of amorphous, colorless, solid foam product in 63% yield. MS ESI+ 409.2 (M+H)$^+$, ESI− 407.2 (M−H)$^−$. NMR: $^1$H (500 MHz; DMSO-d$_6$): 1.35 (d, J=6.7 Hz, —CH(CH$_3$)$_2$); 2.99 (t, J=6.7 Hz, 2H, —CH$_2$—), 3.19 (t, J=6.7 Hz, 2H, —CH$_2$—), 3.26 (sept., J=6.8 Hz, 1H, —CH(CH$_3$)$_2$); 4.73 (s, 2H, —NH—CH$_2$—); 6.51 (s, 1H, H$_{Ar}$); 7.48 (d, J=8.6 Hz, 2H, H$_{Ar}$); 7.71 (s, 1H, H$_{Ar}$); 7.79 (d, J=8.6 Hz, 2H, H$_{Ar}$); 8.45 (d, J=2.1 Hz, 1H, H$_{Ar}$); 8.70 (bs, 1H, —NH—). $^{13}$C (125 MHz; DMSO-d$_6$): 21.7; 25.9; 30.6; 40.5; 42.6; 107.7; 118.4; 127.6; 128.5; 128.6; 136.9; 138.6; 140.8; 159.9. Anal. (C$_2$H$_{24}$N$_8$S) C, H, N.

5-(2-Amino-2-methyl-1-propyl)thio-3-isopropyl-7-[4-(pyrazol-1-yl)benzyl]amino-1(2H)-pyrazolo[4,3-d]pyrimidin (4.90

To a stirred mixture of 3-isopropyl-7-[4-(pyrazol-1-yl)benzyl]amino-1(2H)-pyrazolo[4,3-d]pyrimidine-5-thiol 3.2 (0.71 g, 2.0 mmol) and 0.6 mL of 48% HBr in DMF (6 mL), 2,2-dimethylaziridine (0.31 mL, 4.2 mmol, synthesized according to Org. Synth 1955 Col. 3:148) was added dropwise at room temperature. The reaction mixture was stirred at room temperature for 24 h, then neutralized with aqueous saturated Na$_2$CO$_3$, and the crude product was isolated as a precipitate. The product was purified by column chromatography successively with 3%, 5%, 7% and 10% MeOH in CHCl$_3$ with a small amount of aq. NH$_4$OH. Concentration in vacuo gave 0.49 g of an amorphous, colorless solid foam product in 56% yield. MS ESI+ 437.2 (M+H)$^+$ 100%, ESI− 435.2 (M−H)$^−$. NMR: $^1$H (500 MHz; DMSO-d$_6$): 1.05 (bs, 6H, —C(CH$_3$)$_2$); 1.36 (d, J=7.03 Hz, 6H, —CH(CH$_3$)$_2$); 3.21 (s, 2H, —CH$_2$—); 3.26 (sept., J=7.03 Hz, 1H, —CH(CH$_3$)$_2$); 4.72 (bs, 2H, —NH—CH$_2$—); 6.51-6.52 (m, 1H, H$_{Ar}$); 7.48 (d, J=8.56 Hz, 2H, H$_{Ar}$); 7.71 (d, J=1.53 Hz, 1H, H$_{Ar}$); 7.80 (d, J=8.56 Hz, 2H, H); 8.30 (bs, 1H, —NH—CH$_2$—); 8.45 (d, J=2.14 Hz, 1H, H). $^{13}$C (125 MHz; DMSO-d$_6$): 21.7; 25.8; 28.9; 42.7; 44.0; 50.4; 107.7; 118.4; 127.6; 128.5; 136.9; 138.3; 138.7; 140.8; 145.4; 150.2; 160.9. Anal. (C$_{22}$H$_{28}$N$_8$S) C, H, N.

5-(2-Hydroxy-2-methyl-1-propyl)thio-3-isopropyl-7-[4-(pyrazol-1-yl)benzyl]amino-1(2H)-pyrazolo[4,3-d]pyrimidin (4.93

To a stirred mixture of 3-isopropyl-7-[4-(pyrazol-1-yl)benzyl]amino-1(2H)-pyrazolo[4,3-d]pyrimidine-5-thiol 3.2. (0.37 g, 1 mmol), and tetramethylammonium hydroxide (cat. amount, 40 mg) in MeOH (6 mL), 1,2-epoxy-2,2-dimethylpropane (0.12 mL, 1.3 mmol) was added and the mixture was stirred for 7 hours at room temperature. The crude product was obtained as a precipitate upon addition of water. The pure product was obtained by column chromatography in succession with 2%, 3% MeOH in CHCl$_3$. Evaporation of the solvents in vacuo afforded the product as an amorphous, colorless, solid foam, 0.24 g, yield 55%. MS ESI+ 438.1 (M+H)$^+$, ESI− 436.1 (M−H)$^−$. $^1$H (500 MHz; CDCl$_3$): 1.16 (bs, 6H, —CH(CH$_3$)$_2$); 1.36 (s, 6H, —C(CH$_3$)$_2$); 3.13 (sept., J=6.72 Hz, 1H, —CH(CH$_3$)$_2$); 3.22 (s, 2H, —CH$_2$—); 4.64 (bs, 2H, —NH—CH$_2$—); 6.40-6.41 (m, 1H, H$_{Ar}$); 7.18 (d, J=7.95 Hz, 2H, H$_{Ar}$); 7.40 (d, J=7.95 Hz, 2H, H$_{Ar}$); 7.66 (d, J=1.22 Hz, 1H, H$_{Ar}$); 7.82 (d, J=2.14 Hz, 1H, H$_{Ar}$). $^{13}$C (125 MHz; CDCl$_3$): 21.4; 26.1; 29.3; 43.6; 44.4; 72.0; 107.6; 119.3; 127.1; 128.7; 136.1; 139.1; 141.0; 163.8. Anal. (C$_{22}$H$_{27}$N$_7$OS) C, H, N.

5-(2,3-Dihydroxy-1-propyl)thio-3-isopropyl-7-[4-(pyrazol-1-yl)benzyl]amino-1(2H)-pyrazolo[4,3-d]pyrimidin (4.94

To a solution of 3-isopropyl-7-[4-(pyrazol-1-yl)benzyl]amino-1(2H)-pyrazolo[4,3-d]pyrimidine-5-thiol 3.2 (0.37 g, 1 mmol) in DMF (3 mL) and tetramethylammonium hydroxide (0.11 g), 3-chloro-1,2-propanediol (130 μL, 1.5 mmol) was added and the mixture was stirred at laboratory temperature for 24 h. The crude product was precipitated by addition of water and was then purified by column chromatography: sequentially 2%, 3%, 4% and 5% MeOH in CHCl$_3$. The amorphous, colorless, solid foam product of 0.21 g was obtained in 48% yield. MS ESI+ 440.1 (M+H)$^+$ 10%, 462.2 (M+Na)+100%, ESI− 438.2 (M−H)$^−$. NMR: Mixture of two isomers/tautomers 2/1: $^1$H (500 MHz, DMSO-d$_6$) δ 1.34 (d, J=7.03 Hz, 6H, —CH(C$\underline{H}_3$)$_2$, form A); 1.37 (d, J=7.03 Hz, 6H, —CH(C$\underline{H}_3$)$_2$, form B); 3.04-3.08 (m, 1H, —C$\underline{H}_\alpha$H$_\beta$—S); 3.22-3.32 (m, 2H, —C$\underline{H}$(CH$_3$)$_2$+—CH$_\alpha$$\underline{H}_\beta$—S); 3.71-3.73 (m, 1H, —CH—O);

4.59-4.62 (m, 1H, —CH$_2$—O$\underline{H}$); 4.68 (bd, J=5.50 Hz, 2H, —C$\underline{H}_2$—NH, form B); 4.74 (d, J=5.20 Hz, —C$\underline{H}_2$—NH, form A); 4.97 (d, J=5.2 Hz, 1H, CH—O$\underline{H}$, form A); 5.04 (d, J=4.2 Hz, 1H, CH—O$\underline{H}$, form B); 6.50-6.52 (m, 1H, H$_{Ar}$); 7.46 (d, J=8.2 Hz, 2H, H$_{Ar}$, form B); 7.51 (d, J=8.6 Hz, 2H, H$_{Ar}$, form A); 7.69 (bs, 1H, H$_{Ar}$, form B); 7.71 (bs, 1H, H$_{Ar}$, form A); 7.75 (d, J=8.2 Hz, 2H, H$_{Ar}$, form B); 7.82 (d, J=8.6 Hz, 2H, H$_{Ar}$, form A); 8.04 (t, J=5.2 Hz, —NH, form A); 8.41 (bs, 1H, H$_{Ar}$, form B); 8.44 (d, 1H, H$_{Ar}$, form A); 8.20-8.30 (m, 1H, H$_{Ar}$); 8.69 (app. bt, —NH, isomer B); 12.17 (bs, —NH, form A); 13.75 (bs, —NH form B). $^{13}$C-NMR (125 MHz, DMSO-d$_6$) δ 21.61, 21.73, 24.80, 26.25, 34.33, 42.29, 42.89, 64.73, 71.03, 71.21, 107.63, 107.75, 118.27, 118.48, 120.39, 127.56, 127.62, 128.55, 128.89, 130.40, 134.82, 136.53, 137.49, 138.50, 138.75, 138.87, 139.80, 140.71, 140.84, 148.56, 148.77, 153.70, 161.42, 161.55. Anal. (C$_{21}$H$_{25}$N$_7$O$_2$S) C, H, N.

5-(3-Amino-2-hydroxy-1-propyl)thio-3-isopropyl-7-[4-(pyrazol-1-yl)benzyl]amino-1(2)H-pyrazolo[4,3-d]pyrimidin (4.97

To a solution of 3-isopropyl-7-[4-(pyrazol-1-yl)benzyl]amino-1(2H)-pyrazolo[4,3-d]pyrimidine-5-thiol (0.37 g, 1 mmol) in MeOH (10 mL), K$_2$CO$_3$ (0.17 g) and 3-benzylideneamino-1-chloropropan-2-ol (0.22 g, 1.3 mmol; R/S synthesized from R/S epichlorhydrine according to literature: Proc Res. Develop., 2003, No. 7, 539) was added and the mixture was stirred for 24 hours at 40° C. The reaction mixture was acidified with conc. aq. HCl and stirred for 5 h at 45° C. Crude product was obtained after concentration in vacuo at 50° C., alkalified by addition of 1 g of Na$_2$CO$_3$ solution in 10 ml of water, and crystallized in the refrigerator from this aqueous solution. The product was purified by column chromatography on a 5%, 8% and 10% MeOH in CHCl$_3$ gradient with a small amount of aq. NH$_4$OH. Concentration in vacuo gave: 0.20 g of an amorphous, colorless solid foam product, in 45% yield. MS ESI+ 439.3 (M+H)$^+$ 100%, ESI− 437.2 (M−H)$^−$, NMR: $^1$H (500 MHz; DMSO-d$_6$): 1.34 (d, J=7.03 Hz, 6H, —CH(CH$_3$)$_2$); 2.57 (bs, 1H, —CH$_\alpha$H$_\beta$—NH$_2$); 2.76 (bs, 1H, —CH$_\alpha$H$_\beta$—NH$_2$); 3.09-3.14 (m, 1H, —CH$_\alpha$H$_\beta$—S—); 3.19-3.22 (m, 1H, —CH$_\alpha$H$_\beta$—S—); 3.25 (sept., J=7.03 Hz, 1H, —CH(CH$_3$)$_2$); 3.71 (bs, 1H, —CH—); 4.71 (bs, 2H, —NH—CH$_2$—); 6.51 (dd, J=2.45 Hz, J=1.83 Hz, 1H, H$_{Ar}$); 7.48 (d, J=8.56 Hz, 2H, H$_{Ar}$); 7.71 (d, J=1.57 Hz, 1H, H$_{Ar}$); 7.79 (d, J=8.56 Hz, 2H, H$_{Ar}$); 8.44 (d, J=2.14 Hz, 1H, H$_{Ar}$); 8.83 (bs, 1H, —NH—CH$_2$—). $^{13}$C (125 MHz; DMSO-d$_6$): 21.7; 25.9; 34.7; 42.6; 45.8; 70.5; 107.7; 118.4, 127.6; 128.7; 137.0; 138.3; 138.7; 140.8; 145.8; 150.2; 160.8. Anal. (C$_{21}$H$_{26}$N$_8$OS) C, H, N.

5-(2-Hydroxy-1-ethyl)thio-3-isopropyl-7-[4-(imidazol-4-yl)benzyl]amino-1(2)H-pyrazolo[4,3-d]pyrimidin (4.109

To a stirred mixture of 3-isopropyl-7-[4-(imidazol-4-yl)benzyl]amino-1(2H)-pyrazolo[4,3-d]pyrimidine-5-thiol 3.5. (0.37 g, 1 mmol) and tetramethylammonium hydroxide (catal amount, 40 mg) in MeOH (4 mL), oxirane (80 mg, 1.8 mmol, dissolved in 2 mL of MeOH) was added and the mixture was stirred at room temperature for 8 h. The product was first isolated as a precipitate upon addition of water. The product was purified by column chromatography: sequentially 2%, 4% and 8% MeOH in CHCl3 with a small amount of aq. NH$_4$OH to give 0.23 g of the product as a colorless amorphous solid foam, yield 56%. UV (nm): 259 (široký) λ$_{max}$, 312 λ$_{max}$. MS ESI+ 410.2 (M+H)$^+$, ESI− 408.2 (M−H)$^−$. NMR: $^1$H (500 MHz, DMSO-d$_6$) δ 1.35 (d, J=6.9 Hz, 6H, —CH(C$\underline{H}_3$)$_2$); 3.10-3.16 (m 2H, —C$\underline{H}_2$—CH$_2$—); 3.22-3.26 (m, 1H, —C$\underline{H}$(CH$_3$)$_2$); 3.64 (s, 2H, —CH$_2$—C$\underline{H}_2$—); 4.68 (bs, 2H, NH—CH$_2$—); 4.88 (bs, 1H, —OH); 7.37 (d, 2H, J=7.45 Hz, 2H, H$_{Ar}$); 7.53 (s, 1H, H$_{Ar}$); 7.67 (s, 1H, H$_{Ar}$); 7.74 (d, J=6.9 Hz, 2H, H$_{Ar}$); 7.94 (bs, 1H, —NH), 12.16 (bs, 2H, —NH). $^{13}$C (125 MHz, DMSO-d$_6$): δ 21.4, 21.6, 26.3, 33.0, 43.3, 60.5, 79.1, 120.4, 124.0, 124.3, 127.7, 128.0, 135.8, 136.1, 139.9, 148.6, 148.7, 160.7. Anal. (C$_{20}$H$_{23}$N$_7$OS) C, H, N.

5-(2-Hydroxy-1-ethyl)thio-3-isopropyl-7-[4-(pyrazin-2-yl)benzyl]amino-1(2)H-pyrazolo[4,3-d]pyrimidin (4.133

To a stirred mixture of 3-isopropyl-7-[4-(pyrazin-2-yl)benzyl]amino-1(2H)-pyrazolo[4,3-d]pyrimidine-5-thiol 3.4. (0.37 g, 1 mmol) and tetramethylammonium hydroxide (catal amount, 40 mg) in MeOH (4 mL), oxirane (80 mg, 1.8 mmol, dissolved in 2 mL of MeOH) was added and the mixture was stirred at room temperature for 16 h. The product was first isolated as a precipitate upon addition of water. The product was purified by column chromatography: sequentially 2%, 3% and 4% MeOH in CHCl$_3$ to give 0.23 g of the product as a colorless amorphous solid foam in 55% yield. The product crystallized from DCH/Et$_2$O, m.p. 140-142° C., UV (nm): 246 λ$_{max}$, 307 λ$_{max}$. MS ESI+ 422.2 (M+H)$^+$, ESI− 420.2 (M−H)$^−$. NMR: $^1$H (500 MHz, CDCl$_3$) δ 1.24 (d, J=6.7 Hz, 6H, —CH(C$\underline{H}_3$)$_2$); 3.25-3.19 (m, 3H, —C$\underline{H}$(CH$_3$)$_2$+—CH$_2$—CH$_2$—), 4.01 (t, J=4.9 Hz, 2H, —C$\underline{H}_2$—CH$_2$—), 4.74 (d, J=3.7 Hz, 2H, NH—C$\underline{H}_2$—); 7.32 (d, J=8.3 Hz, 2H, H$_{Ar}$); 7.37 (bs, 1H, —NH); 7.79 (d, J=8.3 Hz, 2H, H$_{Ar}$); 8.44 (d, J=2.4 Hz, 1H, H$_{Ar}$); 8.56 (m, 1H, H$_{Ar}$); 8.88 (d, J=1.2 Hz, 1H, H$_{Ar}$). $^{13}$C (125 MHz, CDCl$_3$) δ 21.53, 25.97, 34.33, 44.20, 64.54, 127.01, 128.38, 135.32, 137.08, 139.61, 141.90, 142.77, 144.14, 150.88, 152.18, 163.60. Anal. (C$_{21}$H$_{23}$N$_7$OS) C, H, N.

5-(2-Amino-1-ethyl)thio-3-isopropyl-7-[4-(pyrazin-2-yl)benzyl]amino-1(2)H-pyrazolo[4,3-d]pyrimidin (4.139

To a stirred mixture of 3-isopropyl-7-[4-(pyrazin-2-yl)benzyl]amino-1(2H)-pyrazolo[4,3-d]pyrimidine-5-thiol 3.4. (0.50 g, 1.33 mmol) and 1.6 mL of 48% HBr in DMF (10 mL), aziridine (0.22 mL, 4 mmol) was added at room temperature. The reaction mixture was stirred at room temperature for 24 h, then neutralized with aqueous saturated Na$_2$CO$_3$, and the crude product was isolated as a precipitate. The product was purified by column chromatography sequentially with 3%, 5%, 7% and 10% MeOH in CHCl$_3$ with a small amount of aq. NH$_4$OH. Concentration in vacuo afforded: 0.25 g of amorphous, colorless solid foam product, in 45% yield. MS ESI+ 421.2 (M+H)$^+$, ESI− 419.2 (M−H)$^−$. NMR: $^1$H (500 MHz, DMSO-d$_6$) δ 1.35 (d, J=6.9 Hz, 6H, —CH(C$\underline{H}_3$)$_2$); 2.93 (t, J=6.6 Hz, 2H, —C$\underline{H}_2$—CH$_2$—); 3.14 (t, J=6.6 Hz, 2H, —CH$_2$—C$\underline{H}_2$—); 3.27 (sept., J=7.2 Hz, 1H, —C$\underline{H}$(CH$_3$)$_2$); 4.77 (bs, 2H, NH—C$\underline{H}_2$—); 7.53 (d, J=8.0 Hz, 2H, H$_{Ar}$); 8.10 (d, J=8.0 Hz, 2H, H$_{Ar}$); 8.58 (d, J=2.3 Hz, 1H, H$_{Ar}$); 8.62 (bs, 1H, —NH); 8.69 (t, J=1.7 Hz, 1H, H$_{Ar}$); 9.22 (s, 1H, H$_{Ar}$). $^{13}$C (125 MHz, DMSO-d$_6$) δ 21.6, 21.7, 25.8, 31.7, 40.4, 42.9, 56.0, 123.6, 126.7, 128.0, 134.6, 138.4, 141.1, 141.9, 143.2, 144.2, 150.3, 151.2, 160.0. Anal. (C$_{21}$H$_{24}$N$_8$S) C, H, N.

TABLE 1

5-alkylthio-7-[(4-arylbenzyl)amino]-1(2)H-pyrazolo[4,3-d]pyrimidines prepared according to Example 1.

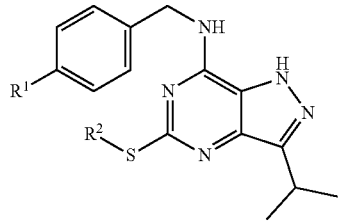

| No | SUBSTITUENT $R^2$ | SUBSTITUENT $R^1$ | CHN ANALYSIS C[%], H[%], N[%] | MS (ZMD)-ANALYSIS $[M - H]^-$ a) | $[M + H]^+$ b) |
|---|---|---|---|---|---|
| 4.1. | 2-hydroxyethyl | pyrid-2-yl | 62.73, 5.86, 19.78 | 419.2 | 421.2 |
| 4.2. | prop-2-en-1-yl | pyrid-2-yl | 66.30, 5.89, 20.08 | 4152 | 417.3 |
| 4.3. | 2-hydroxy-1-propyl | pyrid-2-yl | 63.55, 6.06, 19.24 | 433.2 | 435.2 |
| 4.3a. | 2(R)-hydroxy-1-propyl | pyrid-2-yl | 63.54, 6.08, 19.20 | 433.2 | 435.2 |
| 4.3b. | 2(S)-hydroxy-1-propyl | pyrid-2-yl | 63.51, 6.10, 19.17 | 433.2 | 435.2 |
| 4.4. | 3-hydroxy-2-butyl | pyrid-2-yl | 64.20, 6.36, 18.49 | 447.2 | 449.2 |
| 4.5. | 1-hydroxy-2-butyl | pyrid-2-yl | 64.19, 6.34, 18.53 | 447.2 | 449.2 |
| 4.6. | 2-carbamoyl-1-ethyl | pyrid-2-yl | 61.68, 5.63, 21.88 | 446.2 | 448.2 |
| 4.7. | carbamoylmethyl | pyrid-2-yl | 60.90, 5.44, 22.45 | 432.2 | 434.2 |
| 4.8. | 3-hydroxy-1-propyl | pyrid-2-yl | 63.55, 6.13, 19.33 | 433.2 | 435.2 |
| 4.9. | 2-amino-1-ethyl | pyrid-2-yl | 62.78, 6.30, 23.17 | 418.2 | 420.2 |
| 4.10. | 2-guanidino-1-ethyl | pyrid-2-yl | 59.83, 5.99, 27.25 | 460.2 | 462.3 |
| 4.11. | 2-ureido-1-ethyl | pyrid-2-yl | 59.70, 5.88, 24.24 | 461.2 | 463.3 |
| 4.12. | 2-acetylamino-1-ethyl | pyrid-2-yl | 62.44, 5.93, 21.24 | 460.2 | 462.2 |
| 4.13. | 2-amino-2-methyl-1-propyl | pyrid-2-yl | 64.11, 6.66, 21.70 | 446.2 | 448.2 |
| 4.14. | 2-hydroxycyclohex-1-yl | pyrid-2-yl | 65.76, 6.37, 17.70 | 473.2 | 475.3 |
| 4.15. | 2-hydroxy-1-butyl | pyrid-2-yl | 64.20, 6.34, 18.69 | 447.2 | 449.2 |
| 4.15a. | 2(R)-hydroxy-1-butyl | pyrid-2-yl | 64.15, 6.38, 18.60 | 447.2 | 449.2 |
| 4.15b. | 2(S)-hydroxy-1-butyl | pyrid-2-yl | 64.11, 6.36, 18.62 | 447.2 | 449.2 |
| 4.16. | 2-hydroxycyclopent-1-yl | pyrid-2-yl | 65.00, 6.15, 18.15 | 459.2 | 461.2 |
| 4.17. | 2-hydroxy-2-methyl-1-propyl | pyrid-2-yl | 64.26, 6.35, 18.68 | 447.2 | 449.2 |
| 4.18. | 2,3-dihydroxy-1-propyl | pyrid-2-yl | 61.30, 5.89, 18.63 | 449.2 | 451.2 |
| 4.18a. | 2(R),3-dihydroxy-1-propyl | pyrid-2-yl | 61,28, 5.85, 18.60 | 449.2 | 451.2 |
| 4.18b. | 2(S),3-dihydroxy-1-propyl | pyrid-2-yl | 61.28, 5.83, 18.60 | 449.2 | 451.2 |
| 4.19. | 2-(dimethylamino)ethyl | pyrid-2-yl | 64.30, 6.66, 21.75 | 446.2 | 448.2 |
| 4.20. | 3-(dimethylamino)prop-1-yl | pyrid-2-yl | 64.94, 6.86, 21.24 | 460.2 | 462.2 |
| 4.21. | 1-hydroxy-3-methyl-2-butyl | pyrid-2-yl | 64.88, 6.66, 18.01 | 461.2 | 463.3 |
| 4.22. | β-D-glucopyranosyl | pyrid-2-yl | 57.97, 5.59, 15.55 | 537.3 | 539.3 |
| 4.23. | 3-amino-2-hydroxy-1-propyl | pyrid-2-yl | 61.33, 6.16, 21.71 | 448.2 | 450.2 |
| 4.23a. | 3-amino-2(R)-hydroxy-1-propyl | pyrid-2-yl | 61.30, 6.24, 21.77 | 448.2 | 450.2 |
| 4.23b. | 3-amino-2(S)-hydroxy-1-propyl | pyrid-2-yl | 61.30, 6.30, 21.72 | 448.2 | 450.2 |
| 4.24. | 3-(4-morpholinyl)-2-hydroxy-1-propyl | pyrid-2-yl | 62.29, 6.40, 18.67 | 518.3 | 520.3 |
| 4.25. | 3-(1-piperazinyl)-2-hydroxy-1-propyl | pyrid-2-yl | 62.45, 6.81, 21.51 | 517.3 | 519.3 |
| 4.26. | 2-(1-imidazolyl)ethyl | pyrid-2-yl | 63.77, 5.77, 23.65 | 469.3 | 471.3 |
| 4.27. | 3-amino-1-propyl | pyrid-2-yl | 63.50, 6.57, 22.38 | 432.2 | 434.2 |
| 4.28. | (oxazolidin-2-on-5-yl)methyl | pyrid-2-yl | 60.61, 5.39, 20.60 | 474.3 | 476.3 |
| 4.29. | 2,3-diamino-1-propyl | pyrid-2-yl | 61.39, 6.50, 24.69 | 447.2 | 449.2 |
| 4.30. | 2-(methylthio)-1-ethyl | pyrid-2-yl | 61.28, 5.96, 18.55 | 449.2 | 451.2 |
| 4.31. | 2-aminocyclohexyl | pyrid-2-yl | 65.74, 6.81, 20.57 | 472.3 | 474.3 |
| 4.32. | 3,3,3-trifluoro-2-hydroxy-1-propyl | pyrid-2-yl | 56.50, 4.78, 17.11 | 487.3 | 489.3 |
| 4.33. | methoxymethyl | pyrid-2-yl | 62.77, 5.82, 19.80 | 419.2 | 421.2 |
| 4.34. | 2-(methylamino)-1-ethyl | pyrid-2-yl | 63.48, 6.39, 22.50 | 432.2 | 434.2 |
| 4.35. | 2-sulfanylethyl | pyrid-2-yl | 60.48, 5.51, 19.18 | 435.2 | 437.2 |
| 4.36 | ethyl | pyrid-2-yl | 65.30, 6.00, 20.71 | 403.2 | 405.2 |
| 4.37 | propyl | pyrid-2-yl | 59.89, 6.28, 20.00 | 417.2 | 419.2 |
| 4.38 | butyl | pyrid-2-yl | 66.60, 6.72, 19.31 | 431.2 | 433.2 |
| 4.39 | 2-hydroxypent-3-yl | pyrid-2-yl | 64.85, 6.66, 18.01 | 461.2 | 463.2 |
| 4.40 | 4-hydroxybut-2-yl | pyrid-2-yl | 64.22, 6.29, 18.65 | 447.2 | 449.2 |
| 4.41 | 4-(dimethylamino)butyl | pyrid-2-yl | 65.64, 7.20. 20.62 | 474.3 | 476.3 |
| 4.42 | 2-(diethylamino)ethyl | pyrid-2-yl | 65.61, 7.05, 20.52 | 474.3 | 476.3 |
| 4.43 | 3-(diethylamino)propyl | pyrid-2-yl | 66.01, 7.30, 20.00 | 488.3 | 490.3 |
| 4.44 | 3-aminocyclohexyl | pyrid-2-yl | 65.83, 6.50, 20.57 | 472.3 | 474.3 |
| 4.45 | 4-aminocyclohexyl | pyrid-2-yl | 65.82, 6.84, 20.50 | 472.3 | 474.3 |
| 4.46 | 4-aminobutyl | pyrid-2-yl | 64.19, 6.71, 21.76 | 446.2 | 448.2 |
| 4.47 | 5-aminopentyl | pyrid-2-yl | 64.94, 6.84, 21.21 | 460.2 | 462.3 |
| 4.48 | 3-hydroxy-3-methylbutyl | pyrid-2-yl | 64.90, 6.58, 18.14 | 461.2 | 463.3 |
| 4.49 | 2-amino-3-hydroxypropyl | pyrid-2-yl | 61.40, 6.16, 21.71 | 448.2 | 450.2 |
| 4.50 | 2-hydroxyethyl | imidazol-1-yl | 58.55, 5.68, 23.90 | 408.2 | 410.2 |

TABLE 1-continued 5-alkylthio-7-[(4-arylbenzyl)amino]-1(2)H-pyrazolo[4,3-d]pyrimidines prepared according to Example 1.

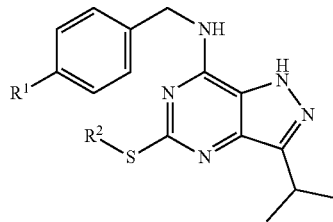

| No | SUBSTITUENT R² | SUBSTITUENT R¹ | CHN ANALYSIS C[%], H[%], N[%] | MS (ZMD)-ANALYSIS [M − H]⁻ a) | [M + H]⁺ b) |
|---|---|---|---|---|---|
| 4.51 | 2-hydroxy-1-propyl | imidazol-1-yl | 59.50, 6.19, 23.03 | 422.2 | 424.2 |
| 4.51a | 2(R)-hydroxy-1-propyl | imidazol-1-yl | 59.48, 6.21, 23.00 | 422.2 | 424.2 |
| 4.51b | 2(S)-hydroxy-1-propyl | imidazol-1-yl | 59.51, 6.09, 23.00 | 422.2 | 424.2 |
| 4.52 | 3-hydroxy-2-butyl | imidazol-1-yl | 60.30, 6.42, 22.35 | 436.2 | 438.2 |
| 4.53 | 1-hydroxy-2-butyl | imidazol-1-yl | 60.30, 6.32, 22.30 | 436.2 | 438.2 |
| 4.54 | 2-carbamoyl-1-ethyl | imidazol-1-yl | 57.76, 5.60, 25.57 | 435.2 | 437.2 |
| 4.55 | carbamoylmethyl | imidazol-1-yl | 56.81, 5.30, 26.42 | 421.2 | 423.2 |
| 4.56 | 3-hydroxy-1-propyl | imidazol-1-yl | 59.55, 5.99, 23.01 | 422.2 | 424.2 |
| 4.57 | 2-aminoethyl | imidazol-1-yl | 58.78, 6.07, 27.45 | 407.2 | 409.2 |
| 4.58 | 2-ureidoethyl | imidazol-1-yl | 55.76, 5.65, 27.83 | 450.2 | 452.2 |
| 4.59 | 2-acetylamino(ethyl) | imidazol-1-yl | 58.60, 5.93, 24.62 | 449.2 | 451.2 |
| 4.60 | 2-amino-2-methyl-1-propyl | imidazol-1-yl | 60.49, 6.69, 25.66 | 435.2 | 437.2 |
| 4.61 | 2-hydroxy-1-butyl | imidazol-1-yl | 60.30, 6.11, 22.22 | 436.2 | 438.2 |
| 4.61a | 2(R)-hydroxy-1-butyl | imidazol-1-yl | 60.28, 6.10, 22.18 | 436.2 | 438.2 |
| 4.61b | 2(S)-hydroxy-1-butyl | imidazol-1-yl | 60.31, 6.10, 22.20 | 436.2 | 438.2 |
| 4.62 | 2-hydroxycyclopent-1-yl | imidazol-1-yl | 61.40, 6.33, 21.70 | 448.2 | 450.2 |
| 4.63 | 2-hydroxy-2-methyl-1-prpyl | imidazol-1-yl | 60.33, 6.34, 22.30 | 436.2 | 438.2 |
| 4.64 | 2,3-dihydroxy1-propyl | imidazol-1-yl | 57.31, 5.74, 22.30 | 438.2 | 440.2 |
| 4.64a | 2(R),3-dihydroxy1-propyl | imidazol-1-yl | 57.29, 5.78, 22.27 | 438.2 | 440.2 |
| 4.64b | 2(S),3-dihydroxy1-propyl | imidazol-1-yl | 57.30, 5.70, 22.28 | 438.2 | 440.2 |
| 4.65 | 2-(dimethylamino)ethyl | imidazol-1-yl | 60.45, 6.67, 25.48 | 435.2 | 437.2 |
| 4.66 | 3-(dimethylamino)prop-1-yl | imidazol-1-yl | 61.21, 6.93, 24.76 | 449.2 | 451.2 |
| 4.67 | 3-amino-2-hydroxy-1-propyl | imidazol-1-yl | 57.51, 6.09, 25.45 | 437.2 | 439.2 |
| 4.67a | 3-amino-2(R)-hydroxy-1-propyl | imidazol-1-yl | 57.47, 6.18, 25.35 | 437.2 | 439.2 |
| 4.67b | 3-amino-2(S)-hydroxy-1-propyl | imidazol-1-yl | 57.45, 6.20, 25.34 | 437.2 | 439.2 |
| 4.68 | 2-(1-imidazolyl)ethyl | imidazol-1-yl | 60.06, 5.76, 27.29 | 458.2 | 460.2 |
| 4.69 | (oxazolidin-2-on-5-yl)methyl | imidazol-1-yl | 56.80, 5.42, 24.11 | 463.2 | 465.3 |
| 4.70 | 2-aminocyclohexyl | imidazol-1-yl | 62.14, 6.79, 24.01 | 461.2 | 463.2 |
| 4.71 | methoxymethyl | imidazol-1-yl | 58.64, 5.64, 23.77 | 408.2 | 410.2 |
| 4.72 | 2-(methylamino)ethyl | imidazol-1-yl | 59.60, 6.49, 26.41 | 421.2 | 423.2 |
| 4.73 | ethyl | imidazol-1-yl | 61.03, 5.80, 24.96 | 392.2 | 394.2 |
| 4.74 | 2-hydroxypent-3-yl | imidazol-1-yl | 61.14, 6.58, 21.61 | 450.2 | 452.2 |
| 4.75 | 4-hydroxybut-2-yl | imidazol-1-yl | 60.29, 6.52, 22.20 | 436.2 | 438.2 |
| 4.76 | 3-aminocyclohexyl | imidazol-1-yl | 62.22, 6.73, 24.00 | 461.2 | 463.2 |
| 4.77 | 4-aminocyclohexyl | imidazol-1-yl | 62.19, 6.75, 24.03 | 461.2 | 463.2 |
| 4.78 | 2-amino-3-hydroxypropyl | imidazol-1-yl | 57.48, 6.12, 25.37 | 437.2 | 439.2 |
| 4.80 | 2-hydroxyethyl | pyrazol-1-yl | 58.50, 5.69, 23.90 | 408.2 | 410.2 |
| 4.81 | 2-hydroxy-1-propyl | pyrazol-1-yl | 59.48, 6.08, 23.08 | 422.2 | 424.2 |
| 4.81a | 2(R)-hydroxy-1-propyl | pyrazol-1-yl | 59.48, 6.05, 23.05 | 422.2 | 424.2 |
| 4.81b | 2(S)-hydroxy-1-propyl | pyrazol-1-yl | 59.50, 6.02, 22.97 | 422.2 | 424.2 |
| 4.82 | 3-hydroxy-2-butyl | pyrazol-1-yl | 60.28, 6.48, 22.34 | 436.2 | 438.2 |
| 4.83 | 1-hydroxy-2-butyl | pyrazol-1-yl | 60.27, 6.34, 22.28 | 436.2 | 438.2 |
| 4.84 | 2-carbamoyl-1-ethyl | pyrazol-1-yl | 57.76, 5.62, 25.55 | 435.2 | 437.2 |
| 4.85 | carbamoylmethyl | pyrazol-1-yl | 56.80, 5.32, 26.40 | 421.2 | 423.2 |
| 4.86 | 3-hydroxy-1-propyl | pyrazol-1-yl | 59.50, 5.98, 23.00 | 422.2 | 424,2 |
| 4.87 | 2-amino-1-ethyl | pyrazol-1-yl | 58.76, 6.08, 27.45 | 407.2 | 409.2 |
| 4.88 | 2-ureido-1-ethyl | pyrazol-1-yl | 55.75, 5.69, 27.81 | 450.2 | 452.2 |
| 4.89 | 2-acetylamino(ethyl) | pyrazol-1-yl | 58.61, 5.95, 24.61 | 449.2 | 451.2 |
| 4.90 | 2-amino-2-methyl-1-propyl | pyrazol-1-yl | 60.48, 6.72, 25.66 | 435.2 | 437.2 |
| 4.91 | 2-hydroxy-1-butyl | pyrazol-1-yl | 60.31, 6.10, 22.24 | 436.2 | 438.2 |
| 4.91a | 2(R)-hydroxy-1-butyl | pyrazol-1-yl | 60.26, 6.11, 22.10 | 436.2 | 438.2 |
| 4.91b | 2(S)-hydroxy-1-butyl | pyrazol-1-yl | 60.30, 6.12, 22.20 | 436.2 | 438.2 |
| 4.92 | 2-hydroxycyclopent-1-yl | pyrazol-1-yl | 61.42, 6.35, 21.68 | 448.2 | 450.2 |
| 4.93 | 2-hydroxy-2-methyl-1-propyl | pyrazol-1-yl | 60.31, 6.36, 22.28 | 436.2 | 438.2 |
| 4.94 | 2,3-dihydroxy1-propyl | pyrazol-1-yl | 57.33, 5.76, 22.30 | 438.2 | 440.2 |
| 4.94a | 2(R),3-dihydroxy1-propyl | pyrazol-1-yl | 57.32, 5.77, 22.29 | 438.2 | 440.2 |
| 4.94b | 2(S),3-dihydroxy1-propyl | pyrazol-1-yl | 57.34, 5.72, 22.26 | 438.2 | 440.2 |
| 4.95 | 2-(dimethylamino)ethyl | pyrazol-1-yl | 60.43, 6.68, 25.45 | 435.2 | 437.2 |

TABLE 1-continued 5-alkylthio-7-[(4-arylbenzyl)amino]-1(2)H-pyrazolo[4,3-d]pyrimidines prepared according to Example 1.

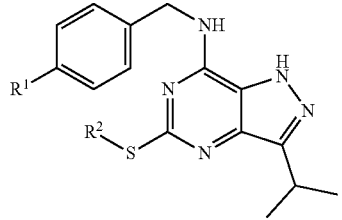

| No | SUBSTITUENT R² | SUBSTITUENT R¹ | CHN ANALYSIS C[%], H[%], N[%] | MS (ZMD)-ANALYSIS [M − H]⁻ a) | [M + H]⁺ b) |
|---|---|---|---|---|---|
| 4.96 | 3-(dimethylamino)prop-1-yl | pyrazol-1-yl | 61.22, 6.94, 24.74 | 449.2 | 451.2 |
| 4.97 | 3-amino-2-hydroxy-1-propyl | pyrazol-1-yl | 57.50, 6.19, 25.38 | 437.2 | 439.2 |
| 4.97a | 3-amino-2(R)-hydroxy-1-propyl | pyrazol-1-yl | 57.47, 6.20, 25.34 | 437.2 | 439.2 |
| 4.97b | 3-amino-2(S)-hydroxy-1-propyl | pyrazol-1-yl | 57.44, 6.22, 25.36 | 437.2 | 439.2 |
| 4.98 | 2-(1-imidazolyl)ethyl | pyrazol-1-yl | 60.08, 5.75, 27.28 | 458.2 | 460.2 |
| 4.99 | (oxazolidin-2-on-5-yl)methyl | pyrazol-1-yl | 56.76, 5.49, 24.11 | 463.2 | 465.3 |
| 4.100 | 2-aminocyclohexyl | pyrazol-1-yl | 62.18, 6.69, 24.04 | 461.2 | 463.2 |
| 4.101 | methoxymethyl | pyrazol-1-yl | 58.65, 5.69, 23.78 | 408.2 | 410.2 |
| 4.102 | 2-(methylamino)ethyl | pyrazol-1-yl | 59.58, 6.50, 26.41 | 421.2 | 423.2 |
| 4.103 | ethyl | pyrazol-1-yl | 61.00, 5.89, 24.90 | 392.2 | 394.2 |
| 4.104 | 2-hydroxypent-3-yl | pyrazol-1-yl | 61.12, 6.59, 21.56 | 450.2 | 452.2 |
| 4.105 | 4-hydroxybut-2-yl | pyrazol-1-yl | 60.30, 6.54, 22.19 | 436.2 | 438.2 |
| 4.106 | 3-aminocyclohexyl | pyrazol-1-yl | 62.20, 6.80, 24.01 | 461.2 | 463.2 |
| 4.107 | 4-aminocyclohexyl | pyrazol-1-yl | 62.21, 6.70, 24.05 | 461.2 | 463.2 |
| 4.108 | 2-amino-3-hydroxypropyl | pyrazol-1-yl | 57.44, 6.22, 25.39 | 437.2 | 439.2 |
| 4.109 | 2-hydroxyethyl | imidazol-4-yl | 58.51, 5.68, 23.88 | 408.2 | 410.2 |
| 4.110 | 2-hydroxy-1-propyl | imidazol-4-yl | 59.44, 6.11, 23.06 | 422.2 | 424.2 |
| 4.110a | 2(R)-hydroxy-1-propyl | imidazol-4-yl | 59.49, 6.02, 23.04 | 422.2 | 424.2 |
| 4.111 | 3-hydroxy-2-butyl | imidazol-4-yl | 60.19, 6.50, 22.34 | 436.2 | 438.2 |
| 4.112 | 2-carbamoyl-1-ethyl | imidazol-4-yl | 57.77, 5.63, 25.53 | 435.2 | 437.2 |
| 4.113 | carbamoylmethyl | imidazol-4-yl | 56.80, 5.30, 26.41 | 421.2 | 423.2 |
| 4.114 | 3-hydrxy-1-propyl | imidazol-4-yl | 59.49, 5.99, 23.06 | 422.2 | 424.2 |
| 4.115 | 2-amino-1-ethyl | imidazol-4-yl | 58.75, 6.09, 27.46 | 407.2 | 409.2 |
| 4.116 | 2-ureido-1-ethyl | imidazol-4-yl | 55.73, 5.71, 27.80 | 450.2 | 452.2 |
| 4.117 | 2-acetylamino(ethyl) | imidazol-4-yl | 58.60, 5.92, 24.63 | 449.2 | 451.2 |
| 4.118 | 2-amino-2-methyl-1-propyl | imidazol-4-yl | 60.35, 6.70, 25.60 | 435.2 | 437.2 |
| 4.119 | 2-hydroxycyclopent-1-yl | imidazol-4-yl | 61.41, 6.30, 21.70 | 448.2 | 450.2 |
| 4.120 | 2-hydroxy-2-methyl-1-propyl | imidazol-4-yl | 60.30, 6.39, 22.29 | 436.2 | 438.2 |
| 4.121 | 2,3-dihydroxy1-propyl | imidazol-4-yl | 57.30, 5.79, 22.25 | 438.2 | 440.2 |
| 4.121a | 2(R),3-dihydroxy1-propyl | imidazol-4-yl | 57.32, 5.72, 22.28 | 438.2 | 440.2 |
| 4.121b | 2(S),3-dihydroxy1-propyl | imidazol-4-yl | 57.31, 5.76, 22.20 | 438.2 | 440.2 |
| 4.122 | 2-(dimethylamino)ethyl | imidazol-4-yl | 60.38, 6.69, 25.42 | 435.2 | 437.2 |
| 4.123 | 3-(dimethylamino)prop-1-yl | imidazol-4-yl | 61.218 6.98, 24.70 | 449.2 | 451.2 |
| 4.124 | 3-amino-2-hydroxy-1-propyl | imidazol-4-yl | 57.45, 6.21, 25.36 | 437.2 | 439.2 |
| 4.124a | 3-amino-2(R)-hydroxy-1-propyl | imidazol-4-yl | 57.46, 6.18, 25.35 | 437.2 | 439.2 |
| 4.125 | 2-(1-imidazolyl)ethyl | imidazol-4-yl | 60.11, 5.65, 27.30 | 458.2 | 460.2 |
| 4.126 | (oxazolidin-2-on-5-yl)methyl | imidazol-4-yl | 56.77, 5.50, 24.11 | 463.2 | 465.3 |
| 4.127 | 2-aminocyclohexyl | imidazol-4-yl | 62.15, 6.70, 24.05 | 461.2 | 463.2 |
| 4.128 | methoxymethyl | imidazol-4-yl | 58.60, 5.70, 23.75 | 408.2 | 410.2 |
| 4.129 | 2-(methylamino)ethyl | imidazol-4-yl | 59.57, 6.43, 26.40 | 421.2 | 423.2 |
| 4.130 | 3-aminocyclohexyl | imidazol-4-yl | 62.22, 6.81, 24.06 | 461.2 | 463.2 |
| 4.131 | 4-aminocyclohexyl | imidazol-4-yl | 62.20, 6.72, 24.03 | 461.2 | 463.2 |
| 4.132 | 2-amino-3-hydroxypropyl | imidazol-4-yl | 57.50, 6.03, 25.40 | 437.2 | 439.2 |
| 4.133 | 2-hydroxy-1-ethyl | pyrazin-2-yl | 59.78, 5.60, 23.19 | 420.2 | 422.2 |
| 4.134 | 2-hydroxy-1-propyl | pyrazin-2-yl | 60.64, 5.85, 22.41 | 434.2 | 436.2 |
| 4.134a | 2(R)-hydroxy-1-propyl | pyrazin-2-yl | 60.62, 5.87, 22.40 | 434.2 | 436.2 |
| 4.135 | 3-hydroxy-2-butyl | pyrazin-2-yl | 61.31, 6.15, 21.70 | 448.2 | 450.2 |
| 4.136 | 2-carbamoyl-1-ethyl | pyrazin-2-yl | 58.84, 5.45, 24.81 | 447.2 | 449.2 |
| 4.137 | carbamoylmethyl | pyrazin-2-yl | 57.90, 5.20, 25.70 | 433.2 | 435.2 |
| 4.138 | 3-hydrxy-1-propyl | pyrazin-2-yl | 60.60, 5.80, 22.40 | 424.2 | 436.2 |
| 4.139 | 2-amino-1-ethyl | pyrazin-2-yl | 59.91, 5.76, 26.55 | 419.2 | 421.2 |
| 4.140 | 2-ureido-1-ethyl | pyrazin-2-yl | 56.84, 5.54, 27.11 | 462.2 | 464.3 |
| 4.141 | 2-acetylamino(ethyl) | pyrazin-2-yl | 59.65, 5.65, 24.15 | 461.3 | 463.3 |
| 4.142 | 2-amino-2-methyl-1-propyl | pyrazin-2-yl | 61.52, 6.31, 24.90 | 447.2 | 449.2 |
| 4.143 | 2-hydroxycyclopent-1-yl | pyrazin-2-yl | 62.33, 5.95, 21.11 | 460.2 | 462.2 |
| 4.144 | 2-hydroxy-2-methyl-1-propyl | pyrazin-2-yl | 61.38, 6.08, 21.70 | 448.2 | 450.2 |
| 4.145 | 2,3-dihydroxy1-propyl | pyrazin-2-yl | 58.49, 5.59, 21.62 | 450.2 | 452.2 |

TABLE 1-continued 5-alkylthio-7-[(4-arylbenzyl)amino]-1(2)H-pyrazolo[4,3-d]pyrimidines prepared according to Example 1.

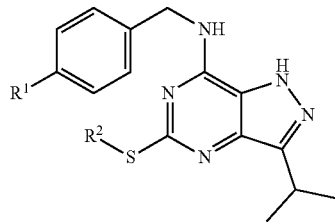

| No | SUBSTITUENT R² | SUBSTITUENT R¹ | CHN ANALYSIS C[%], H[%], N[%] | MS (ZMD)-ANALYSIS [M − H]⁻ a) | [M + H]⁺ b) |
|---|---|---|---|---|---|
| 4.145a | 2(R),3-dihydroxy1-propyl | pyrazin-2-yl | 58.46, 5.52, 21.66 | 450.2 | 452.2 |
| 4.145b | 2(S),3-dihydroxy1-propyl | pyrazin-2-yl | 58.44, 5.63, 21.65 | 450.2 | 452.2 |
| 4.146 | 2-(dimethylamino)ethyl | pyrazin-2-yl | 61.42, 6.26, 24.79 | 447.2 | 449.2 |
| 4.147 | 3-(dimethylamino)prop-1-yl | pyrazin-2-yl | 62.22, 6.50, 24.10 | 461.2 | 463.2 |
| 4.148 | 3-amino-2-hydroxy-1-propyl | pyrazin-2-yl | 58.60, 5.75, 24.66 | 449.2 | 451.2 |
| 4.148a | 3-amino-2(R)-hydroxy-1-propyl | pyrazin-2-yl | 58.59, 5.70, 24.68 | 449.2 | 451.2 |
| 4.149 | 2-(1-imidazolyl)ethyl | pyrazin-2-yl | 61.03 5.38, 26.63 | 470.3 | 472.3 |
| 4.150 | (oxazolidin-2-on-5-yl)methyl | pyrazin-2-yl | 57.91, 5.10, 23.40 | 475.3 | 477.3 |
| 4.151 | methoxymethyl | pyrazin-2-yl | 59.82, 5.50, 23.19 | 420.2 | 422.2 |
| 4.152 | 2-(methylamino)ethyl | pyrazin-2-yl | 60.68, 6.10, 25.56 | 433.2 | 435.2 |
| 4.153 | 3-aminocyclohexyl | pyrazin-2-yl | 63.17, 6.30, 23.49 | 473.2 | 475.2 |
| 4.154 | 4-aminocyclohexyl | pyrazin-2-yl | 63.20, 6.37, 23.55 | 473.2 | 475.2 |
| 4.155 | 2-amino-3-hydroxypropyl | pyrazin-2-yl | 58.54, 5.82, 24.80 | 449.2 | 451.2 |
| 4.156 | 2-hydroxy-1-ethyl | furan-2-yl | 61.52, 5.64, 17.05 | 408.2 | 410.2 |
| 4.157 | 2-hydroxy-1-propyl | furan-2-yl | 62.30, 5.97, 16.34 | 422.2 | 424.2 |
| 4.158 | 3-hydroxy-2-butyl | furan-2-yl | 63.02, 6.21, 15.86 | 436.2 | 438.2 |
| 4.159 | 2-amino-1-ethyl | furan-2-yl | 61.68, 5.99, 20.37 | 407.2 | 409.2 |
| 4.160 | 2-ureido-1-ethyl | furan-2-yl | 58.45, 5.57, 21.64 | 450.2 | 452.2 |
| 4.161 | 2-acetylamino(ethyl) | furan-2-yl | 61.29, 5.80, 18.55 | 449.2 | 451.2 |
| 4.162 | 2-hydroxycyclopent-1-yl | furan-2-yl | 64.08, 6.03, 15.41 | 448.2 | 450.2 |
| 4.163 | 2,3-dihydroxy1-propyl | furan-2-yl | 60.10, 5.84, 15.81 | 438.2 | 440.2 |
| 4.164 | 2-(dimethylamino)ethyl | furan-2-yl | 63.28, 6.49, 19.10 | 435.2 | 437.2 |
| 4.165 | 3-amino-2-hydroxy-1-propyl | furan-2-yl | 60.16, 5.99, 19.03 | 437.2 | 439.2 |
| 4.166 | (oxazolidin-2-on-5-yl)methyl | furan-2-yl | 58.60, 4.91, 18.52 | 449.2 | 451.2 |
| 4.167 | 2-(methylamino)ethyl | furan-2-yl | 62.50, 6.30, 19.77 | 421.2 | 423.2 |
| 4.168 | 2-hydroxy-1-ethyl | thiofen-2-yl | 59.07, 5.40, 16.31 | 424.2 | 426.2 |
| 4.169 | 2-hydroxy-1-propyl | thiofen-2-yl | 60.05, 5.72, 15.87 | 438.2 | 440.2 |
| 4.170 | 3-hydroxy-2-butyl | thiofen-2-yl | 60.80, 6.01, 15.28 | 452.2 | 454.2 |
| 4.171 | 2-amino-1-ethyl | thiofen-2-yl | 59.34, 5.59, 19.59 | 423.2 | 425.2 |
| 4.172 | 2-ureido-1-ethyl | thiofen-2-yl | 56.42, 5.40, 20.88 | 466.2 | 468.2 |
| 4.173 | 2-acetylamino(ethyl) | thiofen-2-yl | 59.11, 5.64, 17.91 | 465.2 | 467.2 |
| 4.174 | 2-hydroxycyclopent-1-yl | thiofen-2-yl | 61.83, 5.82, 15.00 | 464.2 | 466.3 |
| 4.175 | 2,3-dihydroxy1-propyl | thiofen-2-yl | 57.96, 5.63, 15.27 | 454.2 | 456.2 |
| 4.176 | 2-(dimethylamino)ethyl | thiofen-2-yl | 60.88, 6.26, 18.50 | 451.2 | 453.2 |
| 4.177 | 3-amino-2-hydroxy-1-propyl | thiofen-2-yl | 58.01, 5.75, 18.42 | 453.2 | 455.2 |
| 4.178 | (oxazolidin-2-on-5-yl)methyl | thiofen-2-yl | 56.60, 4.70, 17.92 | 465.2 | 467.3 |
| 4.179 | 2-(methylamino)ethyl | thiofen-2-yl | 60.17, 6.01, 19. 06 | 437.2 | 439.2 |
| 4.180 | 2-hydroxy-1-ethyl | oxazol-2-yl | 58.43, 5.42, 20.40 | 409.2 | 411.2 |
| 4.181 | 2-hydroxy-1-propyl | oxazol-2-yl | 59.36, 5.67, 19.54 | 423.2 | 425.2 |
| 4.182 | 3-hydroxy-2-butyl | oxazol-2-yl | 60.19, 5.91, 19.12 | 437.2 | 439.2 |
| 4.183 | 2-amino-1-ethyl | oxazol-2-yl | 58.58, 5.61, 23.82 | 408.2 | 410.2 |
| 4.184 | 2-ureido-1-ethyl | oxazol-2-yl | 55.68, 5.38, 24.47 | 451.2 | 453.2 |
| 4.185 | 2-acetylamino(ethyl) | oxazol-2-yl | 58.32, 5.60, 21.62 | 450.2 | 452.2 |
| 4.186 | 2-hydroxycyclopent-1-yl | oxazol-2-yl | 61.25, 5.85, 18.51 | 449.2 | 451.2 |
| 4.187 | 2,3-dihydroxy1-propyl | oxazol-2-yl | 57.13, 5.47, 18.88 | 439.2 | 441.2 |
| 4.188 | 2-(dimethylamino)ethyl | oxazol-2-yl | 60.23, 6.23, 22.24 | 436.2 | 438.2 |
| 4.189 | 3-amino-2-hydroxy-1-propyl | oxazol-2-yl | 57.31, 5.70, 22.15 | 438.2 | 440.2 |
| 4.190 | (oxazolidin-2-on-5-yl)methyl | oxazol-2-yl | 55.80, 4.60, 21.60 | 450.2 | 452.2 |
| 4.191 | 2-(methylamino)ethyl | oxazol-2-yl | 59.53, 5.77, 23.06 | 422.2 | 424.2 |
| 4.192 | 2-hydroxy-1-ethyl | triazol-2-yl | 55.48, 5.42, 27.01 | 409.2 | 411.2 |
| 4.193 | 2-hydroxy-1-propyl | triazol-2-yl | 56.51, 5.72, 26.29 | 423.2 | 425.2 |
| 4.194 | 3-hydroxy-2-butyl | triazol-2-yl | 57.48, 5.90, 25.32 | 437.2 | 439.2 |
| 4.195 | 2-amino-1-ethyl | triazol-2-yl | 55.65, 5.62, 30.70 | 408.2 | 410.2 |
| 4.196 | 2-ureido-1-ethyl | triazol-2-yl | 52.95, 5.30, 30.66 | 451.2 | 453.2 |
| 4.197 | 2-acetylamino(ethyl) | triazol-2-yl | 55.77, 5.56, 27.81 | 450.2 | 452.2 |
| 4.198 | 2-hydroxycyclopent-1-yl | triazol-2-yl | 58.58, 5.77, 24.83 | 449.2 | 451.2 |
| 4.199 | 2,3-dihydroxy1-propyl | triazol-2-yl | 54.43, 5.55, 25.41 | 439.2 | 441.2 |
| 4.200 | 2-(dimethylamino)ethyl | triazol-2-yl | 57.54, 6.22, 28.70 | 436.2 | 438.2 |

TABLE 1-continued 5-alkylthio-7-[(4-arylbenzyl)amino]-1(2)H-pyrazolo[4,3-d]pyrimidines prepared according to Example 1.

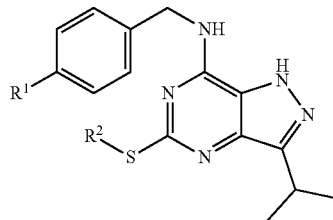

| No | SUBSTITUENT R$^2$ | SUBSTITUENT R$^1$ | CHN ANALYSIS C[%], H[%], N[%] | MS (ZMD)-ANALYSIS [M − H]$^-$ a) | [M + H]$^+$ b) |
|---|---|---|---|---|---|
| 4.201 | 3-amino-2-hydroxy-1-propyl | triazol-2-yl | 54.49, 5.70, 28.58 | 438.2 | 440.2 |
| 4.202 | (oxazolidin-2-on-5-yl)methyl | triazol-2-yl | 53.17, 4.70, 27.77 | 450.2 | 452.2 |
| 4.203 | 2-(methylamino)ethyl | triazol-2-yl | 56.64, 5.95, 29.53 | 422.2 | 424.2 | a) solution: MeOH p.a. + HCOOH
b) solution: MeOH p.a. + H$_2$O + NH$_3$

Example 2 Anti-Lymphoma Activity of Novel Compounds In Vitro

Cytotoxicity of the compounds is the major property determining their anti-lymphoma efficacy in vitro. One of the parameters used, as the basis for cytotoxicity assays, is the metabolic activity of viable cells. For example 2, a microtiter assay, which uses (3-(4,5-dimethylthiazol-2-yl)-2,5-diphenyltetrazolium bromide (MTT), is widely used to quantitate cell proliferation and cytotoxicity. This assay is widely used in drug screening programs and in chemosensitivity testing. Because only metabolically active living cells reduce MTT to correspond purple formazan dye, these assays detect viable cells exclusively. The quantity of reduced MTT corresponds to the number of vital cells in the culture.

The compounds were assayed using the following lymphoma cell lines: HT (diffuse large B-cell lymphoma, subtype—germinal center B-cell), OCI-LY2 (diffuse large B-cell lymphoma, subtype—germinal center B-cell), MINO (mantle cell lymphoma). All cell lines were grown in RPMI medium supplemented with fetal bovine serum and glutamine and maintained at 37° C. in a humidified atmosphere with 5% CO$_2$. For cytotoxicity assays, 5000-10000 cells were seeded into each well of 96 well plate, allowed to stabilize for at least 8 h and then tested compounds were added at various concentrations ranging from 100 to 0.01 μM in triplicates. After three days, MTT solution (5 mg/ml; Sigma, St. Louis, USA) was added to cells and medium was replaced with DMSO after five hours. The absorbance was measured at 620 nm by employing a microplate reader. MTT assays were repeated 3 times for each drug application and untreated cells were used as reference. The GI$_{50}$ values, drug concentrations lethal to 50% of the cells, were calculated from the obtained dose response curves.

TABLE 2

In vitro anti-lymphoma activity of novel compounds.

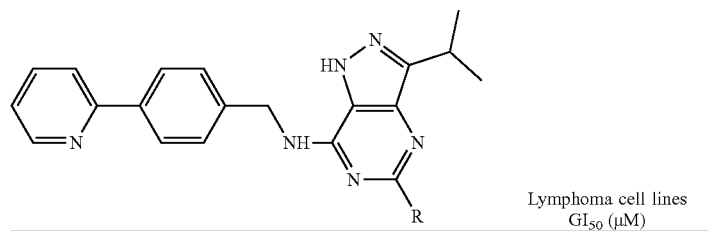

| Compound No. | substituent R(=R$^2$—S—) | Lymphoma cell lines GI$_{50}$ (μM) | | |
|---|---|---|---|---|
| | | HT | OCI-LY2 | MINO |
| 4.1 | 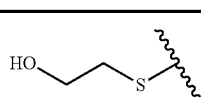 | 0.048 | 0.050 | 0.040 |
| 4.2 | 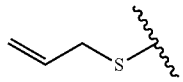 [SMILES: *SCC=C] | 1.005 | 0.858 | 0.923 |

TABLE 2-continued

In vitro anti-lymphoma activity of novel compounds.

| Compound No. | substituent R(=R²—S—) | Lymphoma cell lines GI₅₀ (μM) | | |
|---|---|---|---|---|
| | | HT | OCI-LY2 | MINO |
| 4.3 | HO-CH(CH₃)-CH₂-S- | 0.062 | 0.152 | 0.081 |
| 4.5 | HOCH₂-CH(C₂H₅)-S- | 0.255 | 0.181 | 0.119 |
| 4.6 | H₂N-C(=O)-CH₂CH₂-S- | 0.120 | 0.084 | 0.081 |
| 4.7 | H₂N-C(=O)-CH₂-S- | 0.192 | 0.163 | 0.197 |
| 4.8 | HO-CH₂CH₂CH₂-S- | 0.109 | 0.102 | 0.089 |
| 4.9 | H₂N-CH₂CH₂-S- | 0.040 | 0.046 | 0.029 |
| 4.10 | H₂N-C(=NH)-NH-CH₂CH₂-S- | 0.39 | 0.812 | 0.39 |
| 4.11 | H₂N-C(=O)-NH-CH₂CH₂-S- | 0.240 | 0.198 | 0.136 |
| 4.12 | CH₃-C(=O)-NH-CH₂CH₂-S- | 0.071 | 0.054 | 0.042 |
| 4.13 | H₂N-C(CH₃)₂-CH₂-S- | 0.085 | 0.100 | 0.064 |

TABLE 2-continued
In vitro anti-lymphoma activity of novel compounds.
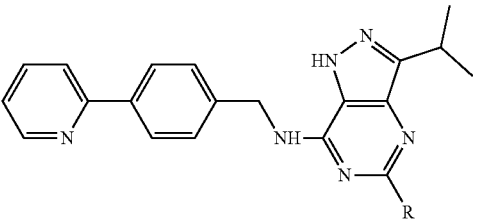
| Compound No. | substituent R(=R²—S—) | Lymphoma cell lines GI$_{50}$ (μM) | | |
|---|---|---|---|---|
| | | HT | OCI-LY2 | MINO |
| 4.14 | 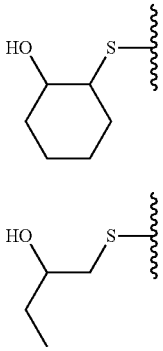 | 0.636 | 0.680 | 0.530 |
| 4.15 | 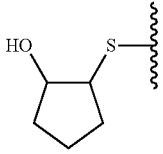 [SMILES: *SC1CCCC1O] | 0.273 | 0.280 | 0.427 |
| 4.16 | 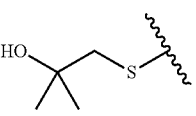 | 0.567 | 0.373 | 0.450 |
| 4.17 | 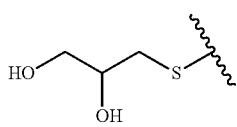 [SMILES: *SCC(O)CO] | 0.507 | 0.610 | 0.477 |
| 4.18 | 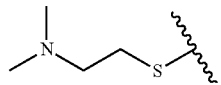 [SMILES: *SCCN(C)C] | 0.021 | 0.022 | 0.010 |
| 4.19 | 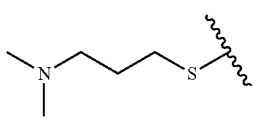 [SMILES: *SCCCN(C)C] | 0.054 | 0.061 | 0.093 |
| 4.20 | 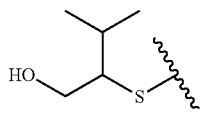 | 0.105 | 0.109 | 0.076 |
| 4.21 | 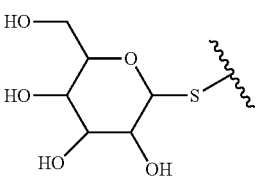 [SMILES: *SC1OC(CO)C(O)C(O)C1O] | 0.980 | 1.001 | 1.307 |
| 4.22 |  | 8.073 | 25.205 | 21.609 |

TABLE 2-continued

In vitro anti-lymphoma activity of novel compounds.

| Compound No. | substituent R(=R²—S—) | Lymphoma cell lines GI$_{50}$ (μM) | | |
|---|---|---|---|---|
| | | HT | OCI-LY2 | MINO |
| 4.23 | H₂N–CH₂–CH(OH)–CH₂–S– | 0.055 | 0.055 | 0.064 |
| 4.23a | H₂N–CH₂–CH(OH)–CH₂–S– (chiral) | 0.063 | 0.099 | 0.051 |
| 4.24 | morpholine-CH₂–CH(OH)–CH₂–S– | 0.200 | 0.200 | 0.243 |
| 4.25 | piperazine-CH₂–CH(OH)–CH₂–S– | 0.332 | 0.435 | 0.767 |
| 4.26 | imidazole-CH₂–CH₂–S– | 0.155 | 0.145 | 0.135 |
| 4.27 | H₂N–CH₂–CH₂–CH₂–S– | 0.120 | 0.151 | 0.156 |
| 4.28 | oxazolidinone-CH₂–S– | 0.080 | 0.053 | 0.069 |
| 4.29 | H₂N–CH₂–CH(NH₂)–CH₂–S– | 0.480 | 0.780 | 0.770 |
| 4.30 | CH₃–S–CH₂–CH₂–S– | 0.975 | 0.668 | 0.773 |

TABLE 2-continued

In vitro anti-lymphoma activity of novel compounds.

[Structure: pyridine-phenyl-CH2-NH-pyrazolo[4,3-d]pyrimidine with isopropyl and R(=R²—S—) substituent]

| Compound No. | substituent R(=R²—S—) | Lymphoma cell lines GI$_{50}$ (µM) | | |
|---|---|---|---|---|
| | | HT | OCI-LY2 | MINO |
| 4.31 | [H$_2$N-cyclohexyl-S-] | 0.139 | 0.136 | 0.157 |
| 4.32 | [HO-CH(CF$_3$)-CH$_2$-S-] | 0.690 | 0.585 | 0.641 |
| 4.33 | [CH$_3$O-CH$_2$-S-] | 0.340 | 0.285 | 0.243 |
| 4.34 | [CH$_3$NH-CH$_2$CH$_2$-S-] | 0.056 | 0.092 | 0.040 |

Example 3 CDK Inhibitory Activities of Novel 5-alkylthio-7-[(4-arylbenzyl)amino]-1(2)H-pyrazolo[4,3-d]pyrimidines CDK2/Cyclin E and CDK1/Cyclin B kinases were produced in Sf9 insect cells via baculoviral infection and purified on a Ni-NTA column (Qiagen). CDK4/Cyclin D1, CDK5/p35NCK, CDK7/Cyclin H/MAT1 and CDK9/Cyclin T1 were purchased from ProQinase GmbH. The kinases were assayed with 1 mg/mL histone H1 (for CDK1/2/5) or (YSPTSPS)2 KK peptide (for CDK7/CDK9) or RPPTL-SPIPHIPR peptide (for CDK4) in the presence of 15/15/15/0.15/1.5/1.5 mMATP (for CDK1/2/4/5/7/9), 0.05 mCi [γ-33P]ATP and of the test compound in a final volume of 10 mL, all in a reaction buffer (60 mM HEPES, NaOH, pH 7.5, 3 mM MgCl$_2$, 3 mM MnCl$_2$, 3 mM Na-orthovanadate, 1.2 mM DTT, 2.5 mg/50 ml PEG$_{20,000}$). The reactions were stopped by adding 5 mL of 3% aq. H$_3$PO$_4$. Aliquots were spotted onto P-81 phosphocellulose (Whatman), washed 3 times with 0.5% aq. H$_3$PO$_4$ and finally air-dried. Kinase inhibition was quantified using a FLA-7000 digital image analyzer (Fujifilm). The concentration of the test compounds required to decrease the CDK activity by 50% was determined from dose response curves and designated as IC$_{50}$.

TABLE 3

CDK2 kinase inhibitory activity of selected compounds expressed as IC$_{50}$.

[Structure: pyridine-phenyl-CH2-NH-pyrazolo[4,3-d]pyrimidine with isopropyl and R substituent]

| Compound number | substituent R(=R²—S—) | Enzyme inhibition IC$_{50}$ (µM) CDK2/E |
|---|---|---|
| 4.1 | [HO-CH$_2$CH$_2$-S-] | 0.003 |
| 4.2 | [CH$_2$=CH-CH$_2$-S-] | 0.100 |

TABLE 3-continued

CDK2 kinase inhibitory activity of selected compounds expressed as IC$_{50}$.

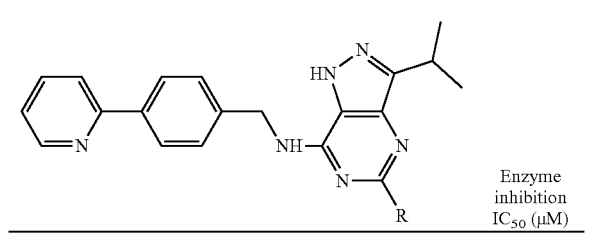
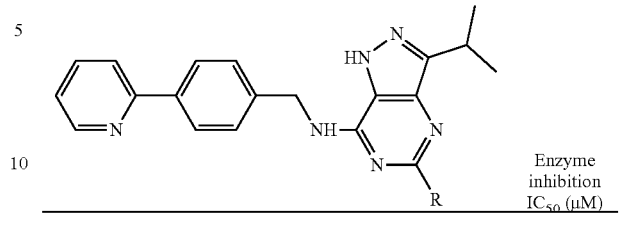

Enzyme inhibition IC$_{50}$ (μM)

| Compound number | substituent R(=R$^2$—S—) | CDK2/E |
|---|---|---|
| 4.3 | HO–CH(CH$_3$)–CH$_2$–S– | 0.012 |
| 4.5 | HO–CH$_2$–CH(CH$_2$CH$_3$)–S– | 0.15 |
| 4.6 | H$_2$N–C(=O)–CH$_2$CH$_2$–S– | 0.019 |
| 4.7 | H$_2$N–C(=O)–CH$_2$–S– | 0.027 |
| 4.8 | HO–CH$_2$CH$_2$CH$_2$–S– | 0.021 |
| 4.9 | H$_2$N–CH$_2$CH$_2$–S– | 0.004 |
| 4.10 | H$_2$N–C(=NH)–NH–CH$_2$CH$_2$–S– | 0.030 |
| 4.11 | H$_2$N–C(=O)–NH–CH$_2$CH$_2$–S– | 0.018 |
| 4.12 | CH$_3$–C(=O)–NH–CH$_2$CH$_2$–S– | 0.041 |
| 4.13 | H$_2$N–C(CH$_3$)$_2$–CH$_2$–S– | 0.020 |
| 4.14 | 2-hydroxycyclohexyl-S– | 0.134 |
| 4.15 | HO–CH$_2$–CH(CH$_2$CH$_3$)–S– (2-hydroxybutyl) | 0.039 |
| 4.16 | 2-hydroxycyclopentyl-S– | 0.052 |
| 4.17 | HO–C(CH$_3$)$_2$–CH$_2$–S– | 0.030 |
| 4.18 | HO–CH$_2$–CH(OH)–CH$_2$–S– | 0.010 |
| 4.19 | (CH$_3$)$_2$N–CH$_2$CH$_2$–S– | 0.077 |
| 4.20 | (CH$_3$)$_2$N–CH$_2$CH$_2$CH$_2$–S– | 0.099 |
| 4.21 | HO–CH$_2$–CH(CH(CH$_3$)$_2$)–S– | 0.077 |
| 4.22 | thio-glucopyranosyl | 0.363 |

TABLE 3-continued

CDK2 kinase inhibitory activity of selected compounds expressed as IC$_{50}$.

| Compound number | substituent R(=R$^2$—S—) | Enzyme inhibition IC$_{50}$ (μM) CDK2/E |
|---|---|---|
| 4.23 | H$_2$N–CH$_2$–CH(OH)–CH$_2$–S– | 0.031 |
| 4.23a | H$_2$N–CH$_2$–CH(OH)–CH$_2$–S– (chiral) | 0.011 |
| 4.24 | morpholino–CH$_2$–CH(OH)–CH$_2$–S– | 0.156 |
| 4.25 | piperazinyl–CH$_2$–CH(OH)–CH$_2$–S– | 0.171 |
| 4.26 | imidazol-1-yl–CH$_2$CH$_2$–S– | 0.032 |
| 4.27 | H$_2$N–CH$_2$CH$_2$CH$_2$–S– | 0.022 |
| 4.28 | oxazolidinone-CH$_2$-S– | 0.019 |
| 4.34 | CH$_3$NH–CH$_2$CH$_2$–S– | 0.013 |
| 4.29 | H$_2$N–CH$_2$–CH(NH$_2$)–CH$_2$–S– | 0.012 |
| 4.30 | CH$_3$S–CH$_2$CH$_2$–S– | 0.138 |
| 4.31 | 2-aminocyclohexyl-S– | 0.052 |
| 4.32 | HO–CH(CF$_3$)–CH$_2$–S– | 0.132 |
| 4.33 | CH$_3$O–CH$_2$–S– | 0.059 |
| 4.35 | HS–CH$_2$CH$_2$–S– | 0.32 |

TABLE 4

Inhibition of CDK2/E complex by selected novel derivatives. The inhibitory aktivity expressed as IC$_{50}$.

| Comp No | Substituent R2 | Substituent R1 | CDK2/E inhibition IC$_{50}$ (μM) |
|---|---|---|---|
| 4.50 | 2-hydroxyethyl | imidazol-1-yl | 0.010 |
| 4.57 | 2-aminoethyl | imidazol-1-yl | 0.005 |
| 4.80 | 2-hydroxyethyl | pyrazol-1-yl | 0.003 |
| 4.81 | 2-hydroxy-1-propyl | pyrazol-1-yl | 0.037 |
| 4.90 | 2-amino-2-methyl-1-propyl | pyrazol-1-yl | 0.011 |
| 4.91 | 2-hydroxy-1-butyl | pyrazol-1-yl | 0.025 |
| 4.93 | 2-hydroxy-2-methyl-1-propyl | pyrazol-1-yl | 0.008 |
| 4.94 | 2,3-dihydroxy1-propyl | pyrazol-1-yl | 0.006 |
| 4.95 | 2-(dimethylamino)ethyl | pyrazol-1-yl | 0.043 |
| 4.96 | 3-(dimethylamino)prop-1-yl | pyrazol-1-yl | 0.060 |

TABLE 4-continued

Inhibition of CDK2/E complex by selected novel derivatives. The inhibitory aktivity expressed as IC$_{50}$.

| Comp No | Substituent R2 | Substituent R1 | CDK2/E inhibition IC$_{50}$ (μM) |
|---|---|---|---|
| 4.97 | 3-amino-2-hydroxy-1-propyl | pyrazol-1-yl | 0.006 |
| 4.109 | 2-hydroxyethyl | imidazol-4-yl | 0.005 |
| 4.133 | 2-hydroxy-1-ethyl | pyrazine-2-yl | 0.006 |
| 4.139 | 2-amino-1-ethyl | pyrazine-2-yl | 0.004 |

TABLE 5

Kinase inhibitory aktivity of compound 4.9 on a broad CDK panel. Compared to a reference compound known from prior art—CR8 ((2S)-2-[[9-propan-2-yl-6-[(4-pyridine-2-ylphenyl)methylamino]purin-2-yl]amino]butan-1-ol).

| Kinases | IC$_{50}$ (μM)* | |
|---|---|---|
| | Comp. 4.9 | CR8 |
| CDK1 | 0.090 ± 0.012 | 0.787 ± 0.100 |
| CDK2 | 0.005 ± 0.001 | 0.062 ± 0.026 |
| CDK4 | 0.603 ± 0.318 | 26.09 |
| CDK5 | 0.015 ± 0.003 | 0.225 ± 0.013 |
| CDK7 | 0.124 ± 0.007 | 1.769 ± 0.013 |
| CDK9 | 0.025 ± 0.002 | 0.272 ± 0.038 |

*tested at least in duplicates

Example 4 Novel Compounds Alter Cell Cycle Profile in Treated Lymphoma Cells Sub-confluent cells were treated with test compounds at different concentrations for 24 h. The cultures were pulse-labeled with 10 mM 5-bromo-2'-deoxyuridine (BrdU) for 30 min at 37° C. prior to harvesting. The cells were then washed in PBS, fixed with 70% ethanol, and denatured in 2M HCl. Following neutralization, the cells were stained with anti-BrdU fluorescein-labeled antibodies, washed, stained with propidium iodide and analyzed by flow cytometry using a 488 nm laser.

As shown below, nanomolar concentration of 4.9 potently reduced population of actively-replicating cells (BrdU positive) in MINO and UPF1H cell lines and accumulated cells in G1 and G2/M phases. We also observed a dose-dependent increase in sub-G1/apoptotic cells.

Example 5 Novel Compounds Activate Caspases 3 and 7 in Lymphoma Cells

Measurement of proapoptotic properties of new compounds was based on quantification of enzymatic activities of caspases-3/7. The cells were homogenized in an extraction buffer (10 mM KCl, 5 mM HEPES, 1 mM EDTA, 1 mM EGTA, 0.2% CHAPS, inhibitors of proteases, pH 7.4) on ice for 20 min. The homogenates were clarified by centrifugation at 10 000×g for 30 min at 4° C., and then the proteins were quantified and diluted to equal concentrations. Lysates were then incubated for 6 h with 100 mM Ac-DEVD-AMC as a substrate of caspases 3 and 7 in the assay buffer (25 mM PIPES, 2 mM EGTA, 2 mM MgCl$_2$, 5 mM DTT, pH 7.3). The fluorescence of the product was measured using a Fluoroskan Ascent microplate reader (Labsystems) at 355/460 nm (excitation/emission).

A fluorimetry-based caspase-3/7 activity assay in MINO and UPF1H cells revealed strong proapoptotic activity of the compound 4.9 compared with control, untreated cells, and showed potent dose-dependent activation of the caspases in nanomolar concentrations after 24 h treatment.

Example 6 Novel Compounds Activate Apoptosis in Treated Lymphoma Cells

Effect of novel compounds on apoptosis was confirmed by immunoblotting analysis of selected apoptotic proteins. For immunoblotting, cell were harvested, washed three times with ice-cold PBS and lysed in a buffer (50 mM Tris, pH 7.4, 250 mM NaCl, 5 mM EDTA, 50 mM NaF, 1 mM Na$_3$VO$_4$, 1% Nonidet P40) containing mixture of protease and phosphatase inhibitors (Sigma-Aldrich). 20 μg of total proteins were separated by SDS-polyacrylamide gel electrophoresis (SDS-PAGE) and transferred onto nitrocellulose membranes. Membranes were blocked in 5% milk and 0.1% Tween 20 in PBS and probed overnight with specific antibodies.

Specific antibodies were purchased from Sigma Aldrich (anti-Bcl-2), Santa Cruz Biotechnology (anti-Mcl-1, clone S-19; anti-PARP, clone F-2; anti-myc), Cell Signaling (anti-caspase-7; anti-caspase-3, clone 3G2; anti-XIAP, anti-Bcl-xl). All primary antibodies were diluted in PBS containing 5% powdered milk; 0.1% Tween 20. Peroxidase conjugated rabbit anti-mouse immunoglobulin or porcine anti-rabbit immunoglobulin antisera (Cell Signaling) were used as the secondary antibodies and visualised with ECL reagents (GE-Healthcare Life Sciences).

Figure 4:
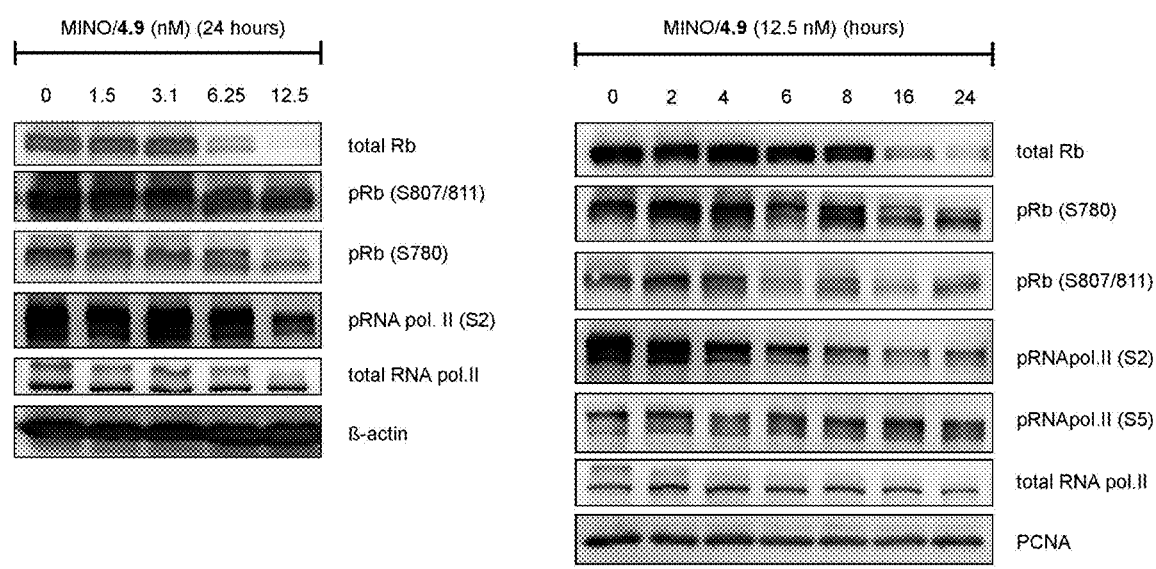
FIG. 4 shows the immunoblotting analysis of important cell cycle regulators in MINO cells treated by various concentrations of compound 4.9 for 24 h (left panel) or by 12.5 nM 4.9 in different time points (right panel). Actin and PCNA levels are included as a control for equal loading.

The results of an immunoblotting analysis of several proteins involved in apoptotic cell death are shown in the FIG. 4. An appearance of the caspase-3-cleaved PARP-1 fragment at 89 kDa after cell exposure to compound 4.9 was observed in treated MINO cells and was markedly associated with a diminution of its full-length form. The activation of mitochondrial apoptosis was evident also from determination of the level of anti-apoptotic protein Mcl-1 and XIAP that showed a dose-dependent decrease. On the other hand, another anti-apoptotic proteins, Bcl-2 and Bcl-xl did not show a decrease, probably due to their cellular stability.

Example 7 Novel 5-alkylthio-7-[(4-arylbenzyl)amino]-1(2)H-pyrazolo[4,3-d]pyrimidines Inhibit Phosphorylation of CDKs Substrates and Inhibit Cellular Transcription by Reduction of Phosphorylation of RNA Polymerase II We monitored levels of phosphorylation retinoblastoma protein, which is known substrate of interphase CDKs and phosphorylation of RNA polymerase II, which is a substrate of CDK7 and CDK9, in cells treated with compound 4.9. Immunoblotting analysis was performed as described in previous Example using appropriate antibodies from Bethyl Laboratories, USA (anti-phospho RNA polymerase II S2 and S5), Millipore (anti-RNA polymerase II, clone ARNA-3), Santa Cruz Biotechnology (anti-β-actin, clone C4) and Cell Signaling (anti-Rb, clone 4H1; anti-pRb antibodies phosphorylated at S780 and S807/811).

Immunoblotting analysis revealed a rapid decrease in phosphorylation at serines 2 and 5 of RNA polymerase II in MINO cell lines in dose and time-dependent manner, confirming cellular inhibition of transcriptional kinases as well as decrease in the phosphorylation of retinoblastoma protein confirming cellular inhibition of interphase CDKs. Significant decrease in the phophorylations was observed in cells treated by 4.9 in concentration of 12.5 nM. Moreover, cellular transcription inhibition has been confirmed by the reduced level of anti-apoptotic protein Mcl-1 (see above), which belongs to the group of short half-life proteins.

Example 8 Antilymphoma Activity of Novel 5-alkylthio-7-[(4-arylbenzyl)amino]-1(2)H-pyrazolo[4,3-d]pyrimidines in vivo In vivo studies were approved by the institutional Animal Care and Use Committee. Immunodeficient NOD.Cg-Prkdcscid I12rgtm1Wj1/SzJ mice (Jackson Laboratory) were maintained in individually ventilated cages. The mantle cell lymphoma MINO cells were injected s.c. (7 mil/mouse) into the 8- to 12-week-old female mice. Therapy with daily i.v. administration of 4.9 resuspended in PBS (or PBS alone) was initiated on day 5. Regression of tumor volume was measured every day and compared with a control group to characterize drug efficacy. In the next experiment the comparison of mice survival after i.p. administrations of 4.9 at different doses to untreated control was studied. Finally, tumor-bearing mice were injected with 4.9 at different doses (5 and 10 mg/kg) and after 24 hours the mice were euthanized, tumors were removed and investigated for the protein expression by immunoblotting analysis. Immunoblotting analysis was performed as described in previous Example with using appropriate antibodies from Bethyl Laboratories, USA (anti-phospho RNA polymerase II S2 and S5), Millipore (anti-RNA polymerase II, clone ARNA-3), Santa Cruz Biotechnology (anti-Mcl-1, clone S-19; anti-PARP, clone F-2) and Cell Signaling (anti-Rb, clone $4H_1$; anti-pRb antibodies; anti-caspase-7; anti-caspase-3, clone 3G2; anti-caspase-7; anti-XIAP, anti-Bcl-xl, anti-Bid, anti-Bax) or Sigma Aldrich (anti-Bcl-2; anti-tubulin).

Figure 5A:
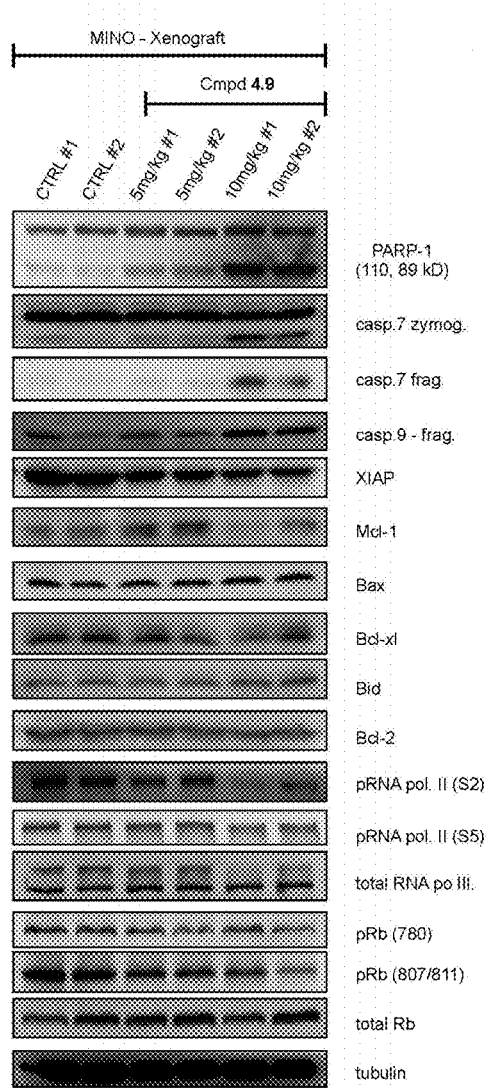
FIG. 5A shows inhibitory effect of pyrazolo[4,3-d]pyrimidine 4.9 on growth of lymphoma xenografts derived from MINO cells. Tumor-bearing mice were intravenously injected with 4.9 at indicated doses, after 24 hours mice were euthanized, tumors removed and cell suspensions were investigated for the expression of the following proteins by immunoblotting analysis.
Figure 5B:
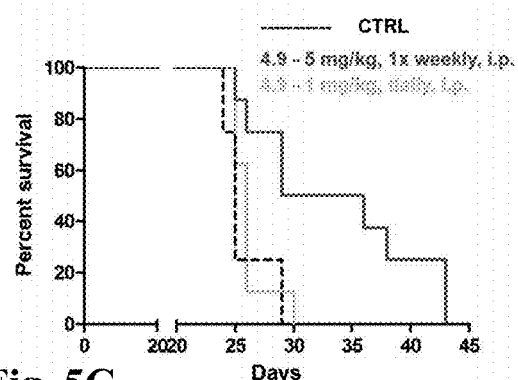
FIG. 5B shows a comparison of overall survival of mice treated with different doses of 4.9 (compared to vehicle-only treated controls).
Figure 5C:
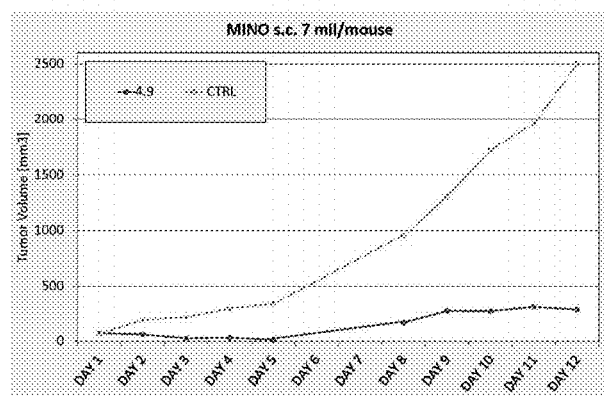
FIG. 5C shows growth curves of vehicle- or 4.9-treated murine tumors after i.v. dosing (10 mg/kg).

As shown in the last FIG. 5, compound 4.9 (i.v. dosing) significantly suppressed tumor growth after 15 days compared to control mice. Comparing i.p. administrations showed us that the optimum dosing schedule in lymphoma xenografts is 1× weekly with dosing 5 mg/kg of 4.9 that significantly prolonged survival of tumor-bearing mice. In the last experiment pharmacodynamic impact of 4.9 on the grown lymphomas was analysed 24 hours after i.v. administration of 4.9 (5 and 10 mg/kg). The results demonstrate that 10 mg/kg dosing is able to activate apoptosis (as documented mainly by monitoring of cleaved PARP and caspase's fragments) and reduce Rb phosphorylation at several phosphosites as indicative for CDK inhibition. We also observed transcriptional inhibition (decrease in the phosphorylation of RNA polymerase II) that clearly affected the expression level of short half-live antiapoptotic protein Mcl-1.

Example 9 Dry Capsules 5000 capsules, each of which contains 0.25 g of one of the compounds of the formula I mentioned in the preceding or following Examples as active ingredient, are prepared as follows:

Composition

| Active ingredient | 1250 g |
| Talc | 180 g |
| Wheat starch | 120 g |
| Magnesium stearate | 80 g |
| Lactose | 20 g |

Preparation Process:

The powdered substances mentioned are pressed through a sieve of mesh width 0.6 mm. Portions of 0.33 g of the mixture are transferred to gelatine capsules with the aid of a capsule-filling machine.

Example 10 Soft Capsules 5000 soft gelatine capsules, each of which contains 0.05 g of one of the compounds of the formula I mentioned in the preceding or following Examples as active ingredient, are prepared as follows:

Composition

| Active ingredient | 250 g |
| Lauroglycol | 2 litres |

Preparation Process:

The powdered active ingredient is suspended in Lauroglykol® (propylene glycol laurate, Gattefossé S.A., Saint Priest, France) and ground in a wet-pulveriser to a particle size of about 1 to 3 µm. Portions of in each case 0.419 g of the mixture are then transferred to soft gelatine capsules by means of a capsule-filling machine.

Example 11 Soft Capsules 5000 soft gelatine capsules, each of which contains 0.05 g of one of the compounds of the formula I mentioned in the preceding or following Examples as active ingredient, are prepared as follows:

Composition

| Active ingredient | 250 g |
| PEG 400 | 1 litre |
| Tween 80 | 1 litre |

Preparation Process:

The powdered active ingredient is suspended in PEG 400 (polyethylene glycol of Mr between 380 and about 420, Sigma, Fluka, Aldrich, USA) and Tween® 80 (polyoxyethylene sorbitan monolaurate, Atlas Chem. Inc., Inc., USA, supplied by Sigma, Fluka, Aldrich, USA) and ground in a wet-pulveriser to a particle size of about 1 to 3 mm. Portions of in each case 0.43 g of the mixture are then transferred to soft gelatine capsules by means of a capsule-filling machine.

The invention claimed is:

1. 5-Alkylthio-7-[(4-arylbenzyl)amino]-1(2)H-pyrazolo[4,3-d]pyrimidines of general formula I

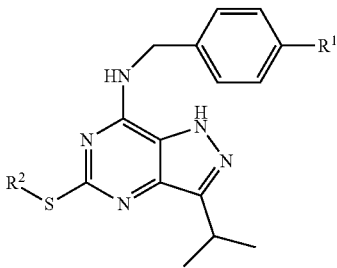

wherein,
R1 is heteroaryl having five to six ring atoms, wherein the ring atoms include at least one heteroatom selected from O, S, N and the other ring atoms are carbon atoms; wherein the heteroaryl can be optionally substituted with one or more substituents independently selected from Cl, F, $CF_3$, $NH_2$, OH, $NO_2$, $OCH_3$, $OCF_3$;

R2 is selected from the group consisting of
  $C_2$-$C_6$ linear or branched alkyl, optionally substituted by one or more substituents selected from the group containing hydroxy, amino, carbamoyl, =O, guanidino, ureido, trifluoromethyl, sulphanyl, methylsulphanyl, dimethylamino, diethylamino, methylamino, ethylamino, C1-C2-acylamino;
  $C_2$-$C_6$ linear or branched alkenyl, optionally substituted by one or more substituents selected from the group containing hydroxy, amino, carbamoyl, =O, guanidino, ureido, trifluoromethyl, sulphanyl, methylsulphanyl, dimethylamino, diethylamino, methylamino, ethylamino, C1-C2-acylamino;
  $C_3$-$C_6$ cycloalkyl, wherein the cycloalkyl contains 3 to 6 carbon atoms and is substituted by one or more substituents selected from the group containing hydroxy, amino, carbamoyl, =O, guanidino, ureido, trifluoromethyl, sulphanyl, methylsulphanyl, dimethylamino, diethylamino, methylamino, ethylamino, C1-C2-acylamino;
  linear or branched heteroalkyl containing 2 to 6 atoms of which at least one is a heteroatom selected from O, S, N and the other are carbon atoms; wherein the heteroalkyl group can be optionally substituted by one or more substituents independently selected from the group containing hydroxy, amino, carbamoyl, =O, guanidino, ureido, trifluoromethyl, sulphanyl, methylsulphanyl, dimethylamino, diethylamino, methylamino, ethylamino, C1-C2-acylamino;
  cycloheteroalkyl containing 3 to 6 atoms of which at least one is a heteroatom selected from O, S, N and the other are carbon atoms; wherein the cycloheteroalkyl group can be optionally substituted by one or more substituents independently selected from the group containing hydroxy, amino, carbamoyl, =O, guanidino, ureido, trifluoromethyl, sulphanyl, methylsulphanyl, dimethylamino, diethylamino, methylamino, ethylamino, C1-C2-acylamino, C1-C4 alkyl;
  cycloheteroalkyl-methyl, cycloheteroalkyl-ethyl or cycloheteroalkyl-propyl, wherein the cycloheteroalkyl group is as described above;
and pharmaceutically acceptable salts thereof, in particular salts with alkali metals, ammonium or amines, or addition salts with acids.

2. 5-Alkylthio-7-[(4-arylbenzyl)amino]-1(2)H-pyrazolo[4,3-d]pyrimidines of general formula I according to claim 1, wherein $R^1$ is selected from the group comprising pyridin-2-yl, pyridin-3-yl, pyridin-4-yl, pyrimidin-2-yl, pyrimidin-4-yl, pyrimidin-5-yl, pyrazin-2-yl, pyridazin-3-yl, pyridazin-4-yl, pyrrol-1-yl, pyrrol-2-yl, pyrrol-3-yl, pyrazol-1-yl, pyrazol-3-yl, pyrazol-4-yl, imidazol-1-yl, imidazol-2-yl, imidazol-4-yl, furan-2-yl, furan-3-yl, thien-2-yl, thien-3-yl, oxazol-2-yl, thiazol-2-yl, tetrazol-5-yl; these groups are unsubstituted or substituted with one or more substituents independently selected from the group consisting of Cl, F, $CF_3$, $NH_2$, OH, $NO_2$, $OCH_3$, $OCF_3$.

3. 5-Alkylthio-7-[(4-arylbenzyl)amino]-1(2)H-pyrazolo[4,3-d]pyrimidines of the general formula I according to claim 1, wherein $R^2$ is a $C_2$-$C_6$ linear or $C_2$-$C_5$ branched alkyl substituted with one or two hydroxy groups; more preferably, $R^2$ is selected from the group consisting of: 2-hydroxyethyl, 2-(RS, R or S)-hydroxypropyl, 3-hydroxypropyl, 2-hydroxybutyl, 1-hydroxybut-2-yl, 2-hydroxybut-2-yl, 1-hydroxy-3-methylbut-2-yl, 4-hydroxybut-2-(RS, R, or S)-yl, 2-hydroxy-2-methylpropyl, 3-hydroxy-3-methylbut-2-yl, (RS, R or S)-2,3-dihydroxypropyl, 1-hydroxy-3-methylbut-2-yl, and (3RS)-2-hydroxypent-3-yl.

4. 5-Alkylthio-7-[(4-arylbenzyl)amino]-1(2)H-pyrazolo[4,3-d]pyrimidines of the general formula I according to claim 1, wherein $R^2$ is $C_2$-$C_6$ linear or branched alkyl substituted with one or two amino groups, optionally the amino group is further substituted.

5. 5-Alkylthio-7-[(4-arylbenzyl)amino]-1(2)H-pyrazolo[4,3-d]pyrimidines of the general formula I according to claim 1, wherein $R^2$ is
  $C_2$-$C_6$ linear or branched alkyl substituted with a carbamoyl group; preferably selected from (carbamoyl)methyl, 2-carbamoyl)ethyl and 3-(carbamoyl)propyl; or
  linear or branched heteroalkyl containing O or S heteroatom; preferably selected from methoxymethyl, ethoxymethyl and 2-(methylthio)ethyl; or
  $C_2$-$C_3$ linear alkyl substituted with one or two sulfanyl groups, or with a combination of sulfanyl and hydroxy groups; preferably selected from the group consisting of 2-sulfanylethyl, 3-hydroxy-2-sulfanylpropyl and 2-hydroxy-3-sulfanylpropyl.

6. 5-Alkylthio-7-[(4-arylbenzyl)amino]-1(2)H-pyrazolo[4,3-d]pyrimidines of the general formula I according to claim 1, wherein $R^2$ is $C_2$-$C_6$ linear or branched alkyl which is simultaneously substituted by amino and hydroxy groups; preferably selected from the group consisting of 3-amino-2-hydroxypropyl, (R)-3-amino-2-hydroxypropyl, (S)-3-amino-2-hydroxypropyl, 2-amino-3-hydroxypropyl, (R)-2-amino-3-hydroxypropyl, and (S)-2-amino-3-hydroxypropyl.

7. 5-Alkylthio-7-[(4-arylbenzyl)amino]-1(2)H-pyrazolo[4,3-d]pyrimidines of the general formula I according to claim 1, wherein $R^2$ is
  $C_3$-$C_6$ cycloalkyl selected from the group containing cyclopropyl, cyclobutyl, cyclopentyl and cyclohexyl; or
  $C_3$-$C_6$ cycloalkyl substituted with amino or hydroxy; the substituent is preferably selected from the group consisting of: trans-4-aminocyclohexyl, cis-4-aminocyclohexyl, cis, trans-4-aminocyclohexyl, cis-2-aminocyclohexyl, trans-2-aminocyclohexyl, cis, trans-2-aminocyclohexyl, 3-aminocyclohexyl, trans-4-hydroxycyclohexyl, cis-4-hydroxycyclohexyl, cis, trans-4-hydroxycyclohexyl, cis-2-hydroxycyclohexyl, trans-2-hydroxycyclohexyl, cis,trans-2-hydroxycyclohexyl, 3-hydroxycyclohexyl.

8. 5-Alkylthio-7-[(4-arylbenzyl)amino]-1(2)H-pyrazolo[4,3-d]pyrimidines of the general formula I according to claim 1, wherein $R^2$ is cycloheteroalkyl, cycloheteroalkyl-methyl, cycloheteroalkyl-ethyl or cycloheteroalkyl-propyl containing at least one nitrogen atom or at least one oxygen atom or both nitrogen and oxygen heteroatoms; preferably selected from the group consisting of: N-morpholinyl, N-pyrrolidinyl, N-pyrazolidinyl, N-imidazolidinyl, N-piperazinyl, N-piperidinyl, N-thiomorpholinyl, 4-methylpiperazin-1-yl, 4-(2-hydroxyethyl)piperazin-1-yl, (aziridin-1-yl)ethyl, (azetidin-1-yl)ethyl, (azolidin-1-yl)ethyl, (piperidin-1-yl)ethyl, (aziridin-1-yl)propyl, (azetidin-1-yl)propyl, (azolidin-1-yl)propyl, (piperidin-1-yl)propyl and 2-oxazolidon-5-yl.

9. A method of treatment of blood hyperproliferative diseases, the method comprising the step of administering 5-Alkylthio-7-[(4-arylbenzyl)amino]-1(2)H-pyrazolo[4,3-d]pyrimidine of the general formula I according to claim 1 to a subject in need thereof.

10. A method of treatment of non-Hodgkin lymphoma, the method comprising the step of administering at least one 5-alkylthio-7-[(4-arylbenzyl)amino]-1(2)H-pyrazolo[4,3-d]pyrimidine of the general formula I according to claim 1 to a subject in need thereof.

11. A method of treatment of non-Hodgkin lymphoma using inhibition of kinases, the method comprising the step of administering 5-Alkylthio-7-[(4-arylbenzyl)amino]-1(2)H-pyrazolo[4,3-d]pyrimidine of the general formula I according to claim 1 to a subject in need thereof.

12. A pharmaceutical composition, characterized in that it comprises at least one 5-alkylthio-7-[(4-arylbenzyl)amino]-1(2)H-pyrazolo[4,3-d]pyrimidines of the general formula I according to claim 1, and at least one pharmaceutically acceptable carrier.

13. 5-Alkylthio-7-[(4-arylbenzyl)amino]-1(2)H-pyrazolo[4,3-d]pyrimidines of the general formula I according to claim 4, wherein $R^2$ is selected from the group consisting of: 2-aminoethyl, 3-aminopropyl, 4-aminobutyl, 5-aminopentyl, 6-aminohexyl, 2,3-diaminopropyl, (R)-2,3-diaminopropyl, (S)-2,3-diaminopropyl, 2-guanidinoethyl, 2-ureidoethyl, 2-(acetylamino)ethyl, (dimethylamino)methyl, 2-(dimethylamino)ethyl, 3-(dimethylamino)propyl, 3-(dimethylamino)butyl, (diethylamino)methyl, 2-(diethylamino)ethyl, 3-(diethylamino)propyl and 4-(diethylamino)butyl.

* * * * *